US008431655B2

(12) United States Patent
Dershem

(10) Patent No.: US 8,431,655 B2
(45) Date of Patent: Apr. 30, 2013

(54) CURATIVES FOR EPOXY COMPOSITIONS

(75) Inventor: Stephen M Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 195 days.

(21) Appl. No.: 12/815,896

(22) Filed: Jun. 15, 2010

(65) Prior Publication Data

US 2010/0249276 A1    Sep. 30, 2010

Related U.S. Application Data

(63) Continuation-in-part of application No. 12/595,505, filed as application No. PCT/US2008/059804 on Apr. 9, 2008.

(60) Provisional application No. 61/186,894, filed on Jun. 15, 2009, provisional application No. 60/922,412, filed on Apr. 9, 2007, provisional application No. 60/930,166, filed on May 15, 2007.

(51) Int. Cl.
C08L 63/00 (2006.01)
C07C 69/00 (2006.01)
C07C 69/02 (2006.01)

(52) U.S. Cl.
USPC ............ 525/533; 528/170; 528/405; 560/4; 560/130; 560/231

(58) Field of Classification Search ................. 525/533; 528/170, 405; 548/414, 500, 520; 560/4, 560/130, 231
See application file for complete search history.

(56) References Cited

U.S. PATENT DOCUMENTS

| | | | |
|---|---|---|---|
| 2,528,417 A | 10/1950 | Bradley |
| 3,201,497 A | 8/1965 | Heino |
| 3,409,589 A | 11/1968 | Kine |
| 3,574,191 A | 4/1971 | Sorrentino |
| 3,691,000 A | 9/1972 | Kalnin |
| 3,739,041 A | 6/1973 | Schmid et al. |
| 4,215,161 A | 7/1980 | Seibold |
| 4,282,390 A | 8/1981 | Mcgarry et al. |
| 4,395,462 A | 7/1983 | Polmanteer |
| 4,486,373 A | 12/1984 | Kurauchi |
| 4,705,716 A | 11/1987 | Tang |
| 4,968,738 A | 11/1990 | Dershem |
| 5,026,794 A | 6/1991 | Ho et al. |
| 5,045,127 A | 9/1991 | Dershem et al. |
| 5,064,480 A | 11/1991 | Dershem et al. |
| 5,232,962 A | 8/1993 | Dershem et al. |
| 5,250,629 A | 10/1993 | Tani et al. |
| 5,306,333 A | 4/1994 | Dershem et al. |
| 5,358,992 A | 10/1994 | Dershem et al. |
| 5,403,389 A | 4/1995 | Dershem |
| 5,418,290 A | 5/1995 | Machida et al. |
| 5,447,988 A | 9/1995 | Dershem et al. |
| 5,489,641 A | 2/1996 | Dershem |
| 5,646,241 A | 7/1997 | Dershem et al. |
| 5,714,086 A | 2/1998 | Osuna et al. |
| 5,717,034 A | 2/1998 | Dershem et al. |
| 5,717,054 A | 2/1998 | Schultz |
| 5,718,941 A | 2/1998 | Dershem et al. |
| 5,753,748 A | 5/1998 | Dershem et al. |
| 5,861,111 A | 1/1999 | Dershem et al. |
| 5,969,036 A | 10/1999 | Dershem |
| 5,973,166 A | 10/1999 | Mizori et al. |
| 5,990,210 A | 11/1999 | Wideman et al. |
| 6,013,704 A | 1/2000 | Hayoz |
| 6,034,194 A | 3/2000 | Dershem |
| 6,034,195 A | 3/2000 | Dershem |
| 6,121,358 A | 9/2000 | Dershem et al. |
| 6,187,886 B1 | 2/2001 | Husson, Jr. et al. |
| 6,211,320 B1 | 4/2001 | Dershem et al. |
| 6,369,183 B1 | 4/2002 | Cook et al. |
| 6,383,653 B1 | 5/2002 | Vaidya |
| 6,423,780 B1 | 7/2002 | Dershem et al. |
| 6,429,281 B1 | 8/2002 | Dershem et al. |
| 6,482,899 B2 | 11/2002 | Ohashi et al. |
| 6,521,731 B2 | 2/2003 | Dershem et al. |
| 6,610,808 B2 | 8/2003 | De et al. |
| 6,620,946 B2 | 9/2003 | Dershem et al. |
| 6,743,852 B2 | 6/2004 | Dershem et al. |
| 6,750,301 B1 | 6/2004 | Bonneau et al. |
| 6,790,597 B2 | 9/2004 | Dershem |
| 6,825,245 B2 | 11/2004 | Dershem |

(Continued)

FOREIGN PATENT DOCUMENTS

| | | |
|---|---|---|
| EP | 1834969 | 9/2007 |
| JP | 02199127 A2 | 8/1990 |

(Continued)

OTHER PUBLICATIONS

International Search Report for PCT/US08/59804 Aug. 28, 2008.
Iizawa et al., "Regioselective reaction of oxiranes with S-Phenyl Thioesters catalyzed by quaternary onium salts or crown ether-metal salt compleses", *Bull Chem Soc Jpn*:62:597-8;1989.
Mimura et al., "Characteristics of epoxy resin cured with in situ polymerized curing agen", *Polymer* 43;7559-7566; 2002.
Nakamura et al., "Epoxy Resins (Curing Reactions)", *Polymeric Materials Encyclopedia (Salamone ed; CRC Press*, Boca Raton, FL) 2238-46, 1996.
Nakamura et al., "Thermal analysis of epoxy curing using polyfunctional active esters as curing agents", *Thermochimica Acta 183*:269-277, 1991.
STN structure search report by STIC of USPTO for related U.S. Appl. No. 12/595,505 containing Abstract of Journal of Chemical Society (1957),2729-31 at pp. 31-32, Nov. 2011.

*Primary Examiner* — Tae H Yoon
(74) *Attorney, Agent, or Firm* — The Law Office of Jane K. Babib, Professional Corporation; Jane K. Babin

(57) ABSTRACT

The invention provides epoxy and oxetane compositions including the novel acyloxy and N-acyl curing agents described herein. Use of invention curing agents result in cured adhesive compositions with remarkably increased adhesion and reduced hydrophilicity when compared to resins cured with other types of curing agents. Furthermore, the curatives of this invention do not interfere with free-radical cure and are thus suited for use in hybrid cure thermoset compositions.

12 Claims, 1 Drawing Sheet

U.S. PATENT DOCUMENTS

| | | |
|---|---|---|
| 6,831,132 B2 | 12/2004 | Liu et al. |
| 6,852,814 B2 | 2/2005 | Dershem et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 6,977,057 B2 | 12/2005 | Reitz et al. |
| 7,102,015 B2 | 9/2006 | Dershem et al. |
| 7,119,160 B2 | 10/2006 | Kodama et al. |
| 7,157,587 B2 | 1/2007 | Mizori et al. |
| 7,176,044 B2 | 2/2007 | Forray et al. |
| 7,199,249 B2 | 4/2007 | Liu et al. |
| 7,208,566 B2 | 4/2007 | Mizori et al. |
| 7,230,055 B2 | 6/2007 | Musa |
| 7,285,613 B2 | 10/2007 | Dershem et al. |
| 7,309,724 B2 | 12/2007 | Dershem et al. |
| 7,517,925 B2 | 4/2009 | Dershem et al. |
| 7,582,078 B2 | 9/2009 | Chen et al. |
| 7,678,879 B2 | 3/2010 | Dershem |
| 7,777,064 B2 | 8/2010 | Mizori |
| 7,786,234 B2 | 8/2010 | Dershem et al. |
| 7,786,248 B2 | 8/2010 | Dershem |
| 7,795,362 B2 | 9/2010 | Dershem |
| 7,868,113 B2 | 1/2011 | Dershem |
| 7,875,688 B2 | 1/2011 | Dershem et al. |
| 7,884,174 B2 | 2/2011 | Mizori et al. |
| 7,928,153 B2 | 4/2011 | Dershem |
| 8,008,419 B2 | 8/2011 | Dershem |
| 8,013,104 B2 | 9/2011 | Dershem |
| 8,039,663 B2 | 10/2011 | Dershem |
| 8,043,534 B2 | 10/2011 | Dershem |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0087999 A1 | 5/2003 | Dershem et al. |
| 2003/0096123 A1 | 5/2003 | Yeager |
| 2003/0109666 A1 | 6/2003 | Dershem et al. |
| 2003/0120077 A1 | 6/2003 | Galbo et al. |
| 2003/0125551 A1 | 7/2003 | Dershem et al. |
| 2003/0178138 A1 | 9/2003 | Taukagoshi |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0099331 A1 | 5/2004 | Buckner |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0107542 A1 | 5/2005 | Liu et al. |
| 2005/0119362 A1 | 6/2005 | Ishikawa |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009578 A1 | 1/2006 | Dershem |
| 2006/0025542 A1 | 2/2006 | Musa |
| 2006/0063014 A1 | 3/2006 | Forray |
| 2006/0069232 A1 | 3/2006 | Dershem |
| 2006/0089447 A1 | 4/2006 | Robertson et al. |
| 2006/0142517 A1 | 6/2006 | Dershem |
| 2006/0171981 A1 | 8/2006 | Richard et al. |
| 2007/0042173 A1 | 2/2007 | Nagaoka et al. |
| 2007/0117925 A1 | 5/2007 | Strickler et al. |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |
| 2010/0113643 A1 | 5/2010 | Dershem |
| 2010/0144977 A1 | 6/2010 | Dershem |
| 2011/0017400 A1 | 1/2011 | Dershem |
| 2011/0152466 A1 | 6/2011 | Dershem |

FOREIGN PATENT DOCUMENTS

| | | |
|---|---|---|
| JP | 04093318 A2 | 3/1992 |
| JP | H10-505599 | 6/1998 |
| JP | 10287715 | 10/1998 |
| WO | 9607691 | 3/1996 |
| WO | 2004099331 A2 | 11/2004 |
| WO | 2004099331 A3 | 11/2004 |
| WO | WO-2005121190 | 12/2005 |
| WO | WO-2007100329 | 9/2007 |
| WO | 2008077141 A1 | 6/2008 |
| WO | WO-2008077141 | 6/2008 |
| WO | 2008092168 A2 | 7/2008 |
| WO | WO-2008124797 | 10/2008 |
| WO | WO-2008130894 | 10/2008 |
| WO | 2009117729 A2 | 9/2009 |
| WO | 2009117729 A3 | 9/2009 |
| WO | 2008092168 A3 | 12/2009 |
| WO | 2010019832 A3 | 2/2010 |
| WO | WO-2010019832 | 2/2010 | though many inventive examples are diphenols acylated with two different anhydrides.

CURATIVES FOR EPOXY COMPOSITIONS

CROSS REFERENCE TO RELATED APPLICATIONS

This application claims the benefit of priority under 35 USC §119(e) of U.S. Provisional Application Ser. No. 61/186,894, filed, Jun. 15, 2009, and is a Continuation-in-Part of U.S. patent application Ser. No. 12/595,505, filed Oct. 9, 2009, which is in turn a U.S. National Phase under 35 U.S.C. §371 of PCT/US08/59804, filed Apr. 9, 2008, which in turn claims the benefit of priority to U.S. Provisional Application Ser. Nos. 60/922,412, filed Apr. 9, 2007 and 60/835,684, filed Aug. 4, 2006 the entire disclosures of which are incorporated herein by reference.

FIELD OF THE INVENTION

The present invention relates to thermosetting compositions, methods of preparation and uses therefor. In particular, the present invention relates to thermosetting compounds and compositions containing epoxy and oxetane resins, and acetoxy, acyloxy, and N-acyl curatives therefor.

BACKGROUND

The properties of cured epoxy resins are often influenced by the curing agent that is added to the formulation. Accordingly, much research effort has been directed towards developing curing agents that can enhance the properties of the cured resin. Phenols, anhydrides, thiols and amines have generally been used as curing agents in epoxy resins. While useful, these curing agents are not without certain drawbacks. Thus, a continuing need exists for new epoxy curing agents.

SUMMARY OF THE INVENTION

The present invention provides curative compounds that impart outstanding properties for epoxy and oxetane cure. More specifically, acetoxy, acyloxy, and N-acyl curatives are described, as well as epoxy and oxetane resin compositions that include these curatives. The resulting thermosets can have reduced hydrophilicity, decreased viscosity, increased thermal resistance, and increased hydrolytic stability. In contrast to phenolic curatives, the acetoxy, acyloxy, and N-acyl curatives described herein do not substantially interfere with free-radical cure chemistry. This feature expands opportunities for hybrid cures, i.e. those that combine ring opening addition cures of epoxies and/or oxetanes with any of the free-radically curable monomers.

When an N-acyl compound of the invention is used as a curative, an N-acylated imide co-cure with an epoxy resins resulting in polyimides, which are considered to be one of the highest performance resins with respect to thermal resistance. Certain compounds of this invention, therefore, provide a means of converting epoxy monomers into polyimide resins.

One desirable feature of the N-acyl curatives described herein that is their high level of reactivity. They can, for example, be used to cure aliphatic and cycloaliphatic epoxies Anhydrides have previously been the only class of curatives available for the aliphatic and cycloaliphatic epoxies. The N-acyl compounds of this invention can be used to provide thermosets with superior hydrolytic and thermal resistance compared to adhesives, coatings, encapsulants, or matrix resins that utilize anhydride curatives. Furthermore, the N-acyl curatives of this invention, unlike anhydrides, do not react with moisture at room temperature. This can be an important consideration for shelf-life and product performance in humid environments.

The compounds of the invention are useful for single lay-up, two stage cures. In certain of these embodiments, a di-functional epoxy or oxetane monomer may be cured with a di-functional acyloxy compound to form a thermoplastic intermediate. The initially formed polymer may then be cross-linked to a final thermoset in a second step. This chemistry is, therefore, the ideal platform for b-stageable adhesives.

The compounds of the invention are also useful in a variety of other applications. Invention compounds can be used in automotive, marine, and aerospace coatings and adhesives. The properties of certain invention compounds make these compounds suitable for use in dental matrix resins and adhesives. Invention compounds can also be used as components of matrix resins and composites used in sports equipment, automotive bodies, and boat construction, such as those incorporating carbon fiber and/or fiberglass reinforcements. The compounds of the present invention also have attractive properties for use in adhesives for diverse industrial applications, such as thread-lock materials and building materials. They are also well suited for use in electronic mold compounds and underfill.

In general, epoxies are known for their excellent adhesion, chemical and heat resistance, good to excellent mechanical properties and very good electrical insulating properties, but many of these properties can be modified. For example, although epoxies are typically electrically insulating, epoxies filled with silver or other metals can be electrically conductive.

The curatives of this invention can be used, for example, with aliphatic, cycloaliphatic, glycidyl ether, glycidyl ester, and glycidyl amine epoxies, as well as with combinations thereof. Furthermore, these compounds may be used as curatives for oxetane monomers. In many instances the compounds of this invention may be used as the sole curatives for epoxy or oxetane monomers. The curatives of this invention, for example, do not interfere with free radical co-cures and are therefore are useful as the sole curatives in hybrid cure systems that also contain free radical monomers. However, for epoxy- or oxetane-based resin compositions that do not contain free radical monomers it may be desirable to combine the compounds of this invention with other curatives, such as phenols, anhydrides, thiols, etc.

The curatives of this invention may be either liquids or solids. It is desirable, however, for many applications that they are in liquid form, or at least completely soluble in other reactive components in the formulation. Lower melting compounds are generally more compatible with other formulation components. Epoxy curatives that either liquid at room temperature or low melting are, therefore, desirable. It has been found that mixed acyloxy functionality can be used advantageously to depress the melting points of these curatives. The use of more than one acyloxy functional group in the synthesis of phenyl ester curatives results in a mixture of compounds. Thus, the reaction of a diphenol with one-half equivalent each of acetic anhydride and propionic anhydride would result in a 1:2:1 product distribution of the acetate-acetate: acetate-propionate:propionate:propionate ester compounds. This mixed phenyl ester product will have a lower melting point than could be obtained from the use of a single acylating agent. The benefit of this approach, however, is not limited to only diphenol starting materials or the combination that include just two acylating agents.

Accordingly, the present invention provides curatives for epoxy or oxetane resins having the structure of Formula I or Formula II:

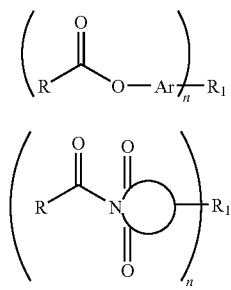

wherein each of R and $R_1$ is, independently, a substituted or an unsubstituted aliphatic, heteroaliphatic, aromatic, heteroaromatic, siloxane, acrylate, methacrylate, maleimido, cinnamyl moiety; Ar is a substituted or an unsubstituted aryl or heteroaryl having from 6 to about 20 carbon atoms; and n is an integer having the value between 1 and about 11. In certain embodiments, each of R and $R_1$ is, independently, a substituted or an unsubstituted alkyl, cycloalkyl, alkenyl, aryl, or heterocyclic moiety. In other embodiments, Ar is a substituted or an unsubstituted $C_6$ to about $C_{11}$ aryl or heteroaryl. In certain aspects of the invention, n is an integer having the value between 1 and about 11, for example, having the value between 2 and 11, between 3 and 11, between 4 and 11, or between 5 and 11. In certain other aspects of the invention, n is an integer having the value between 1 and about 6, for example, having the value between 2 and 6, between 3 and 6, between 4 and 6, or between 5 and 6. In certain embodiments, the curatives of the present invention are liquids at room temperature.

In some aspects of the invention each R and $R_1$ is the same. In other embodiments $R_1$ is different than at least on R. For example, $R_1$ can be different than the R at the terminus of the compound (terminal R group) or $R_1$ can be different an internal R.

Some specific examples of curatives provided by the present invention include, but are not limited to, any of the following compounds:

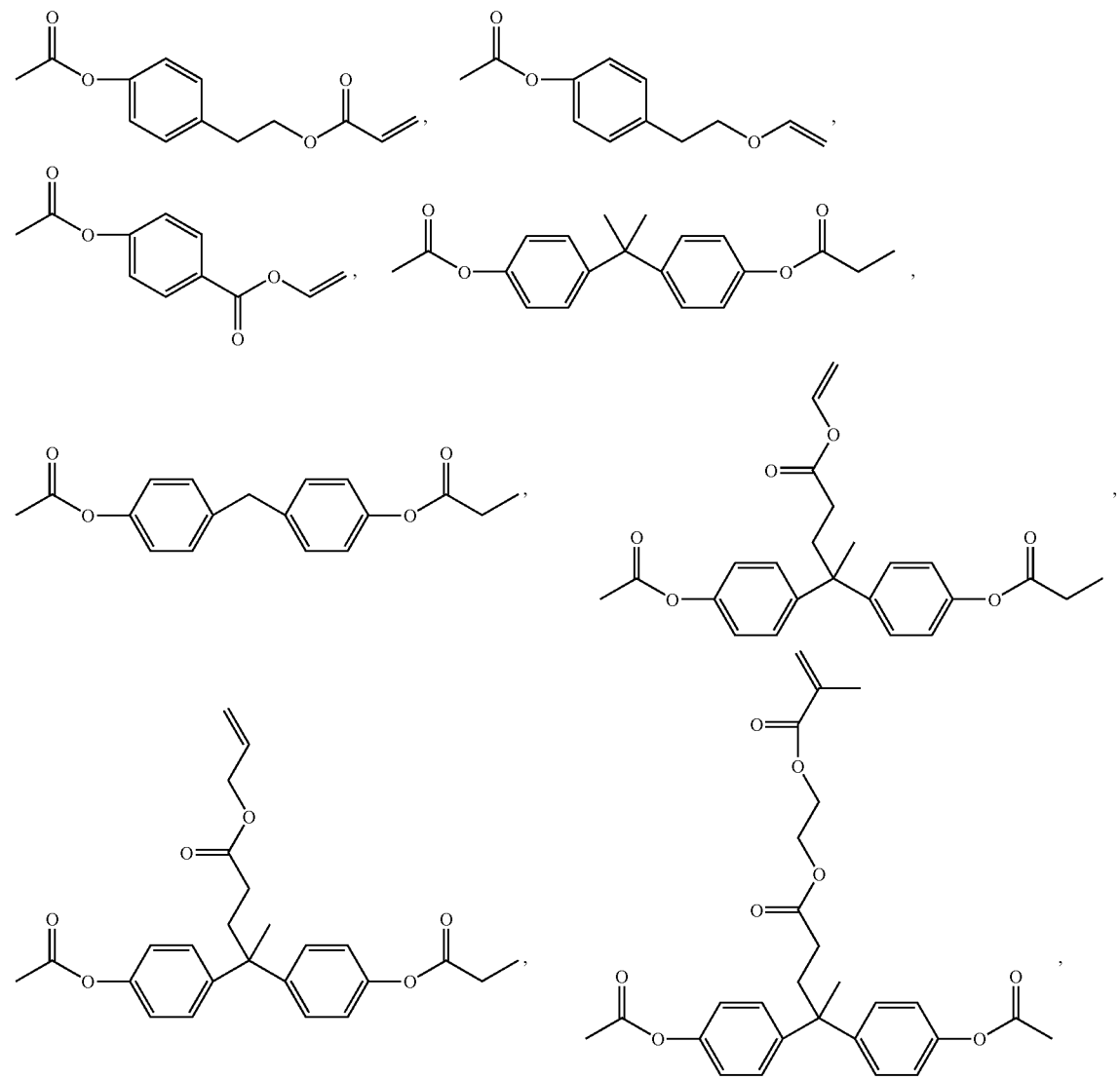

-continued
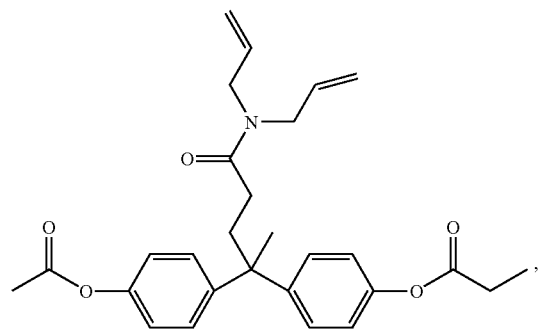
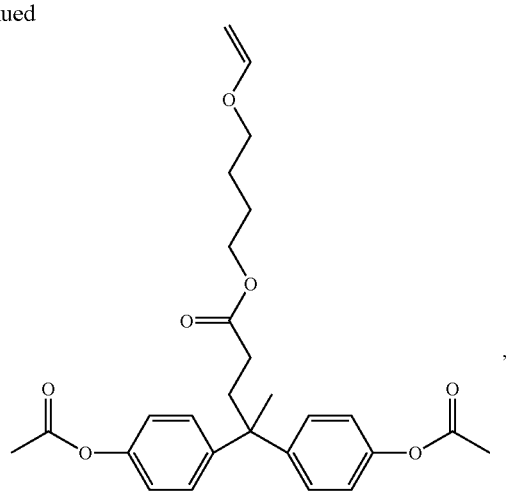
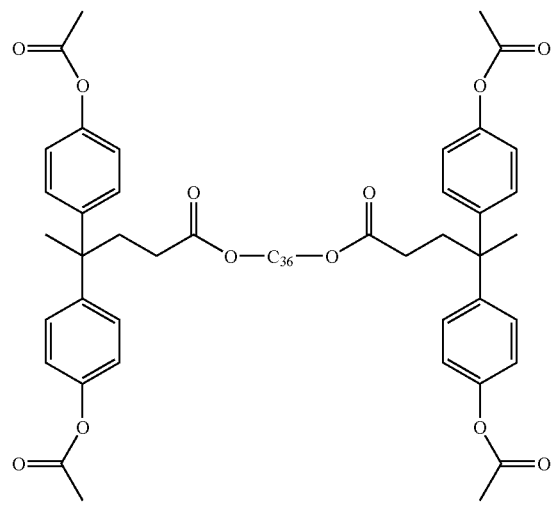
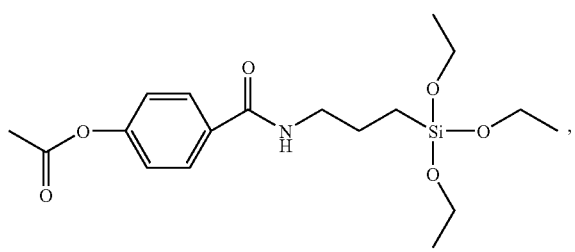
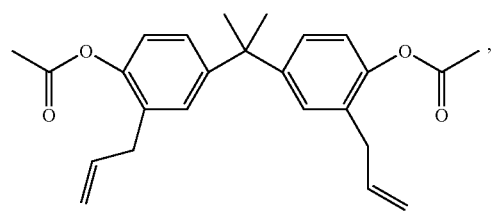
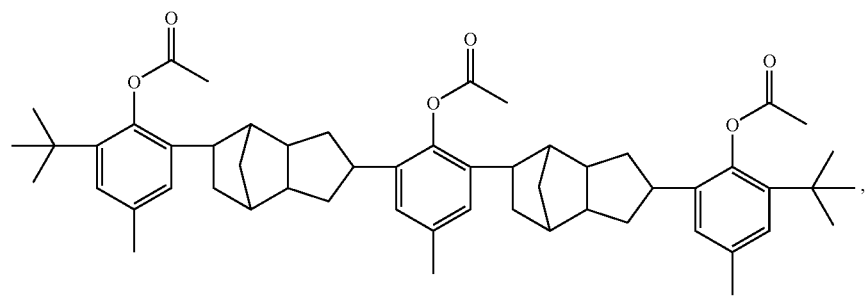

-continued
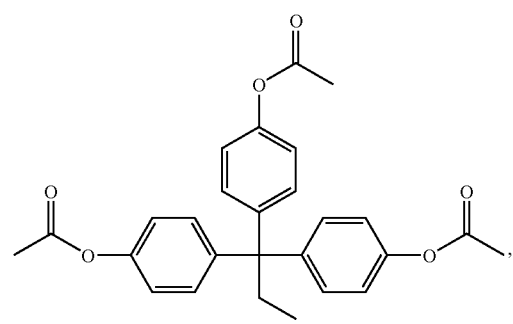
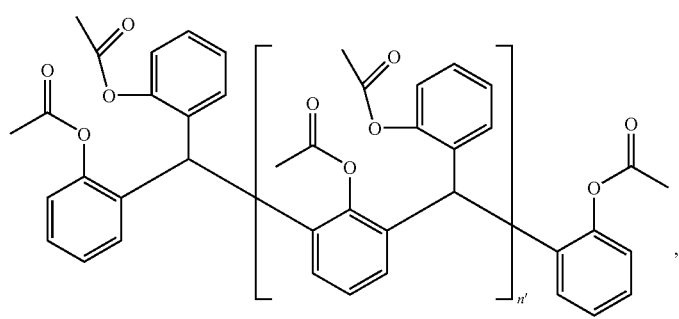
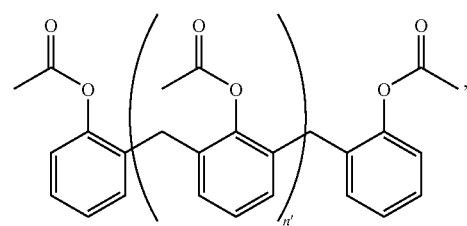
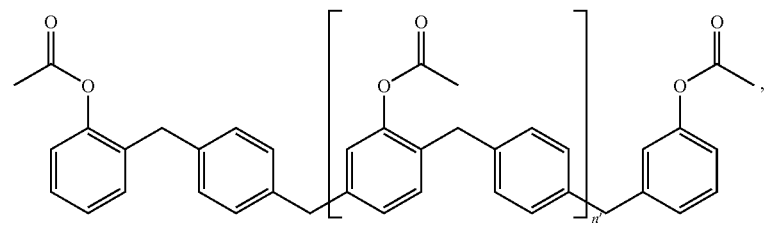
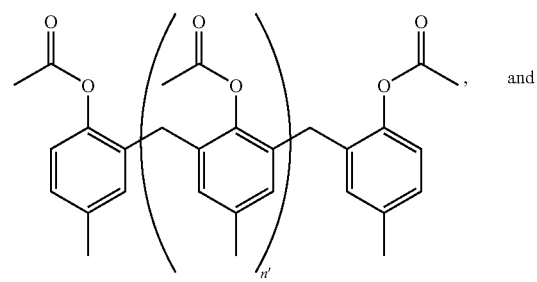, and
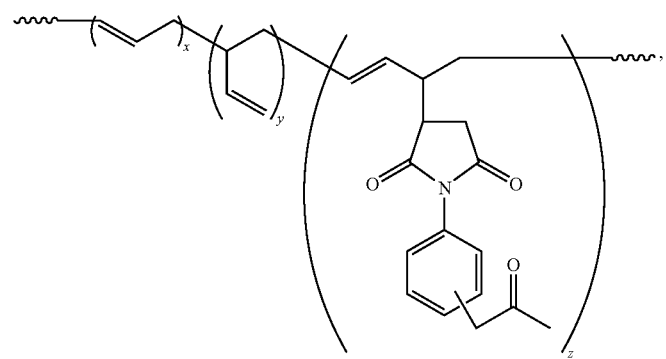

wherein each of n', x, y and z is an integer, independently having the following values: n' between 0 and 10, each of x and y between 4 and about 50, and z between 2 and about 40.

The present invention also provides poly-N-acyl curatives, including:

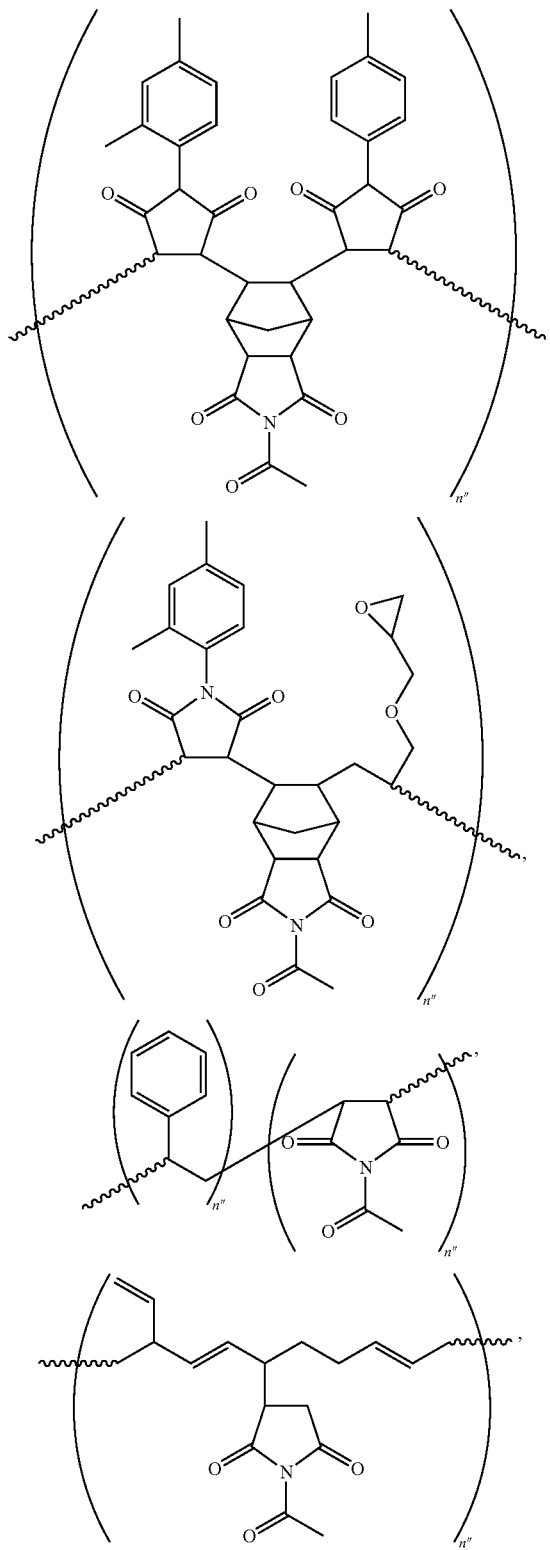

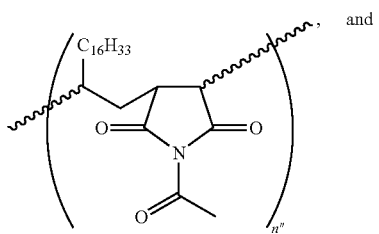

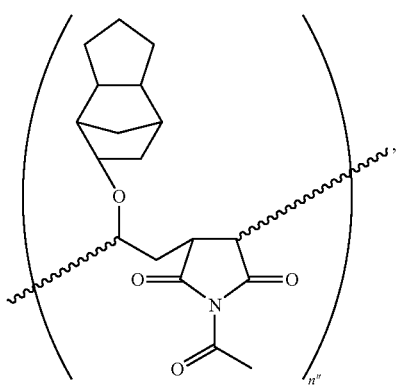

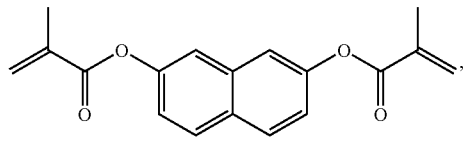

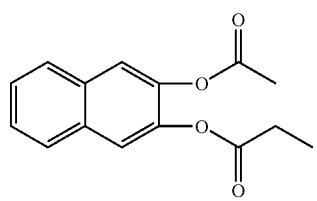

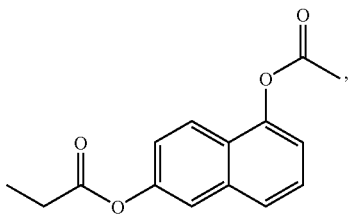

wherein each of n'' and n''' is an integer independently having the value between 1 and about 10.

In addition, curatives according to the embodiments of the invention also include, but not limited to, the following compounds:

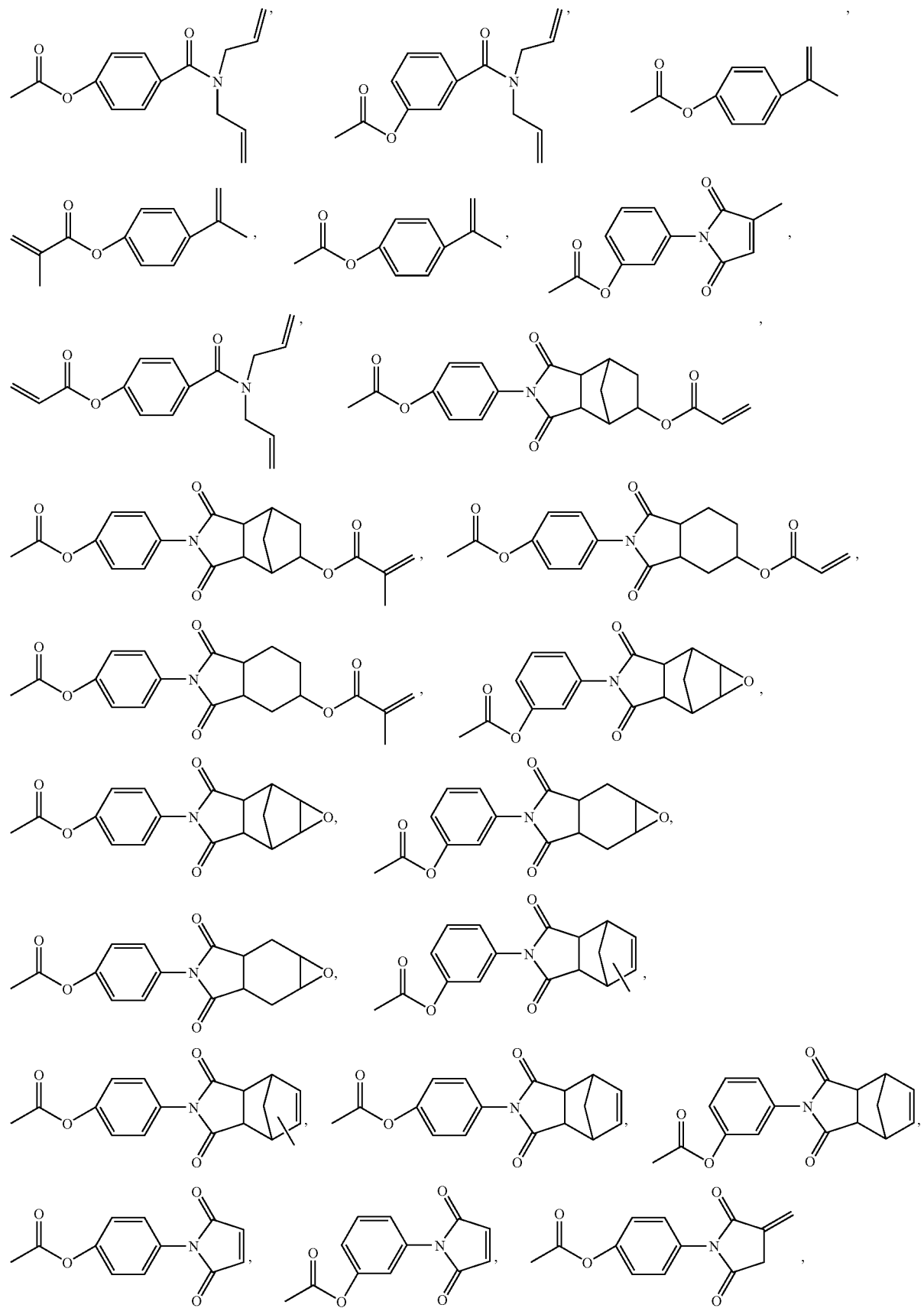

-continued
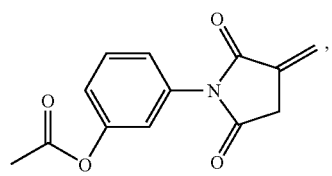 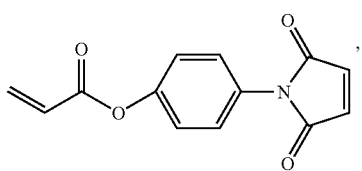 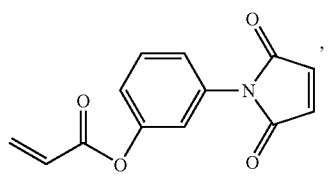
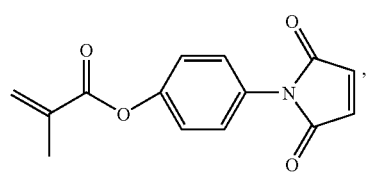 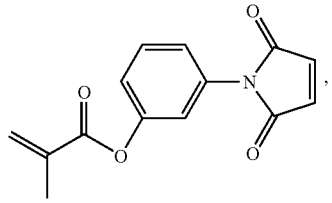 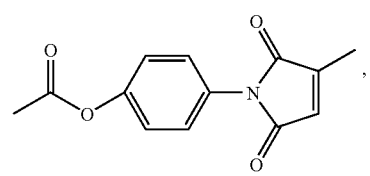
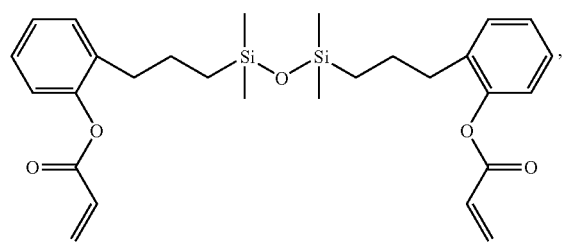
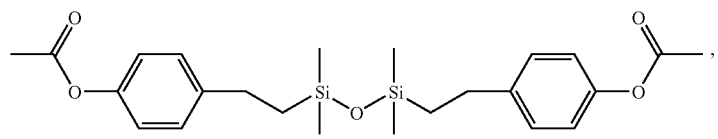
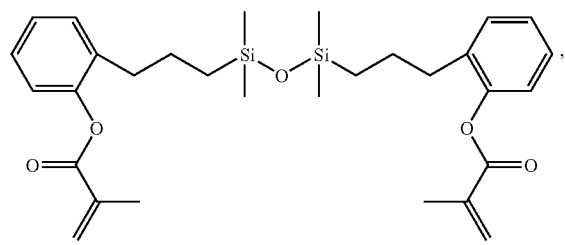 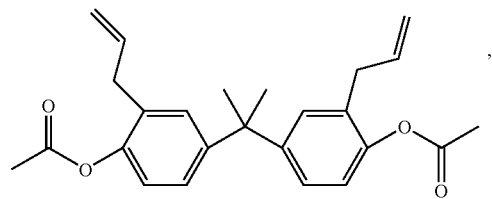
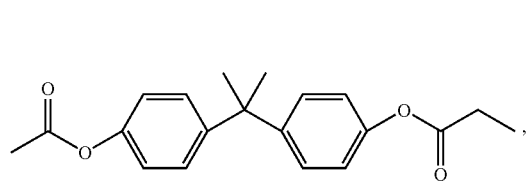 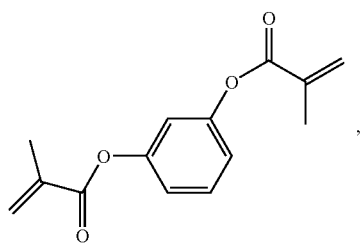
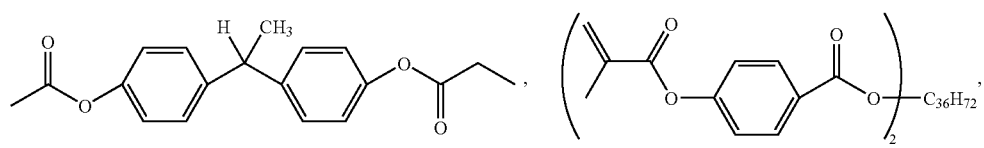 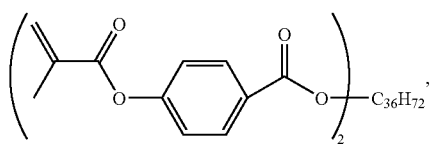
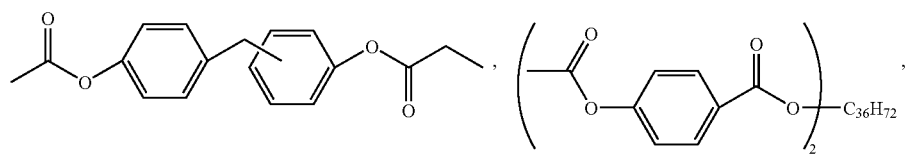 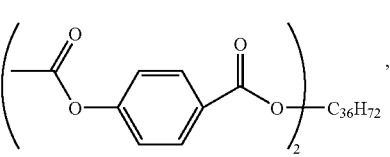

-continued
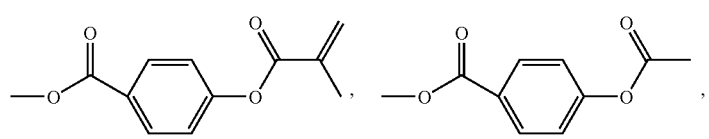
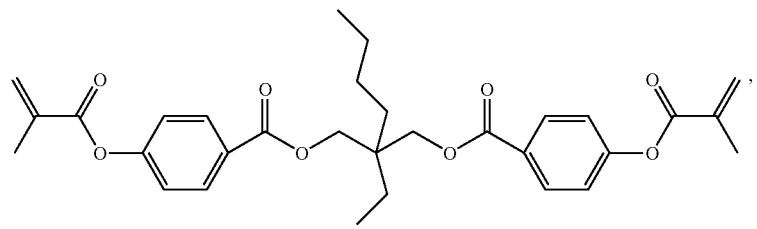
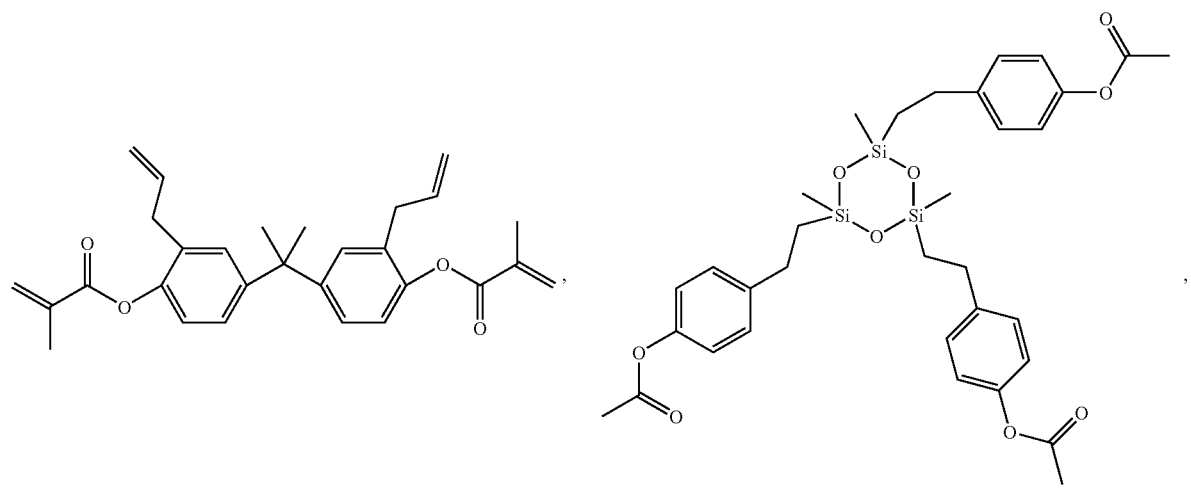
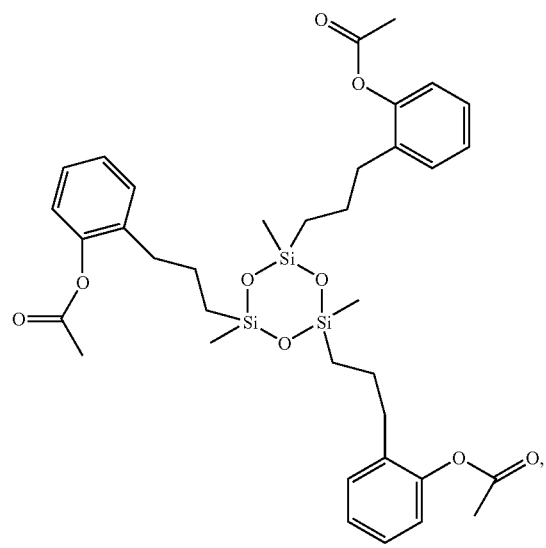

-continued
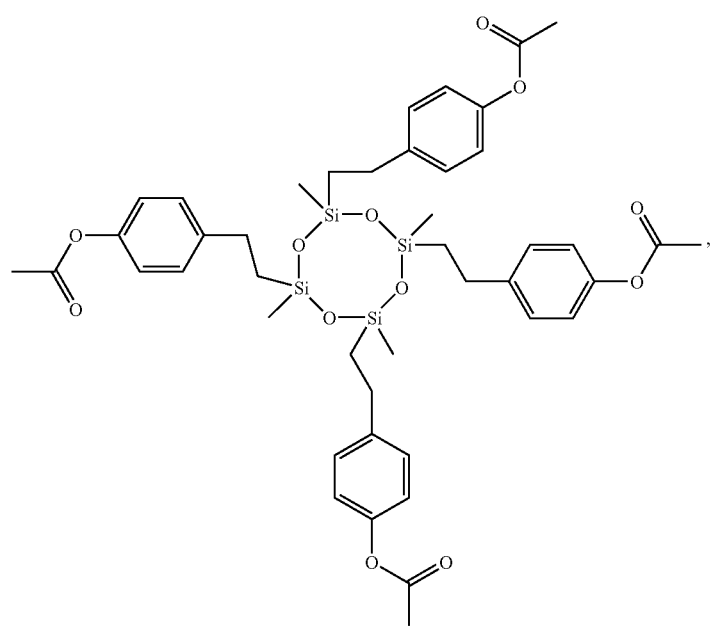
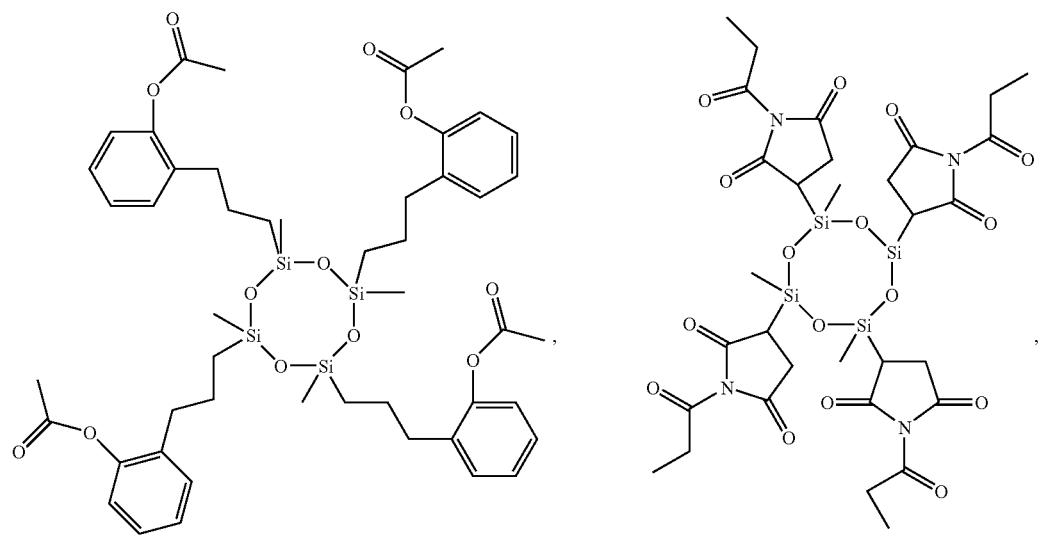

-continued
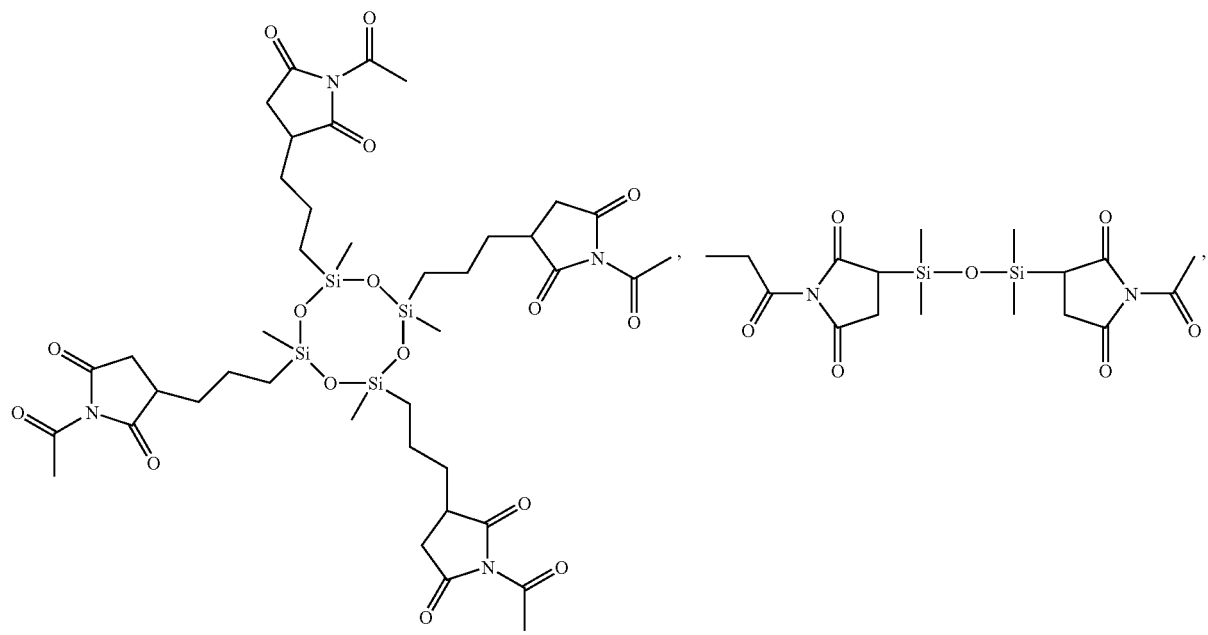
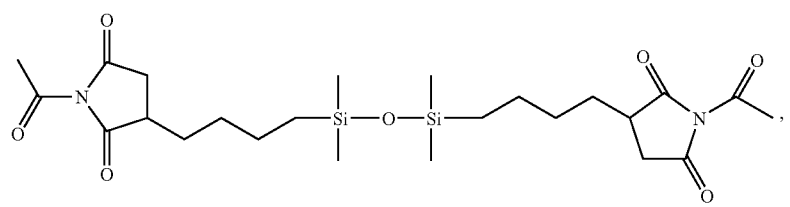
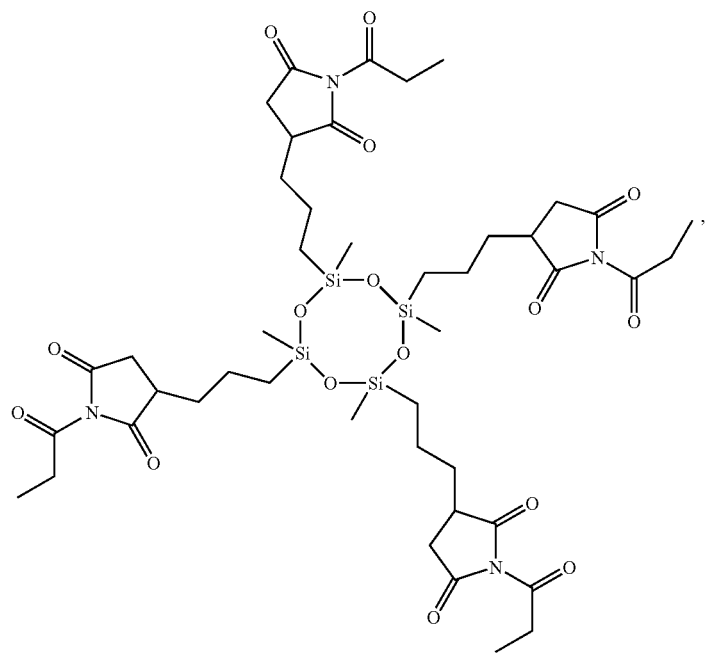

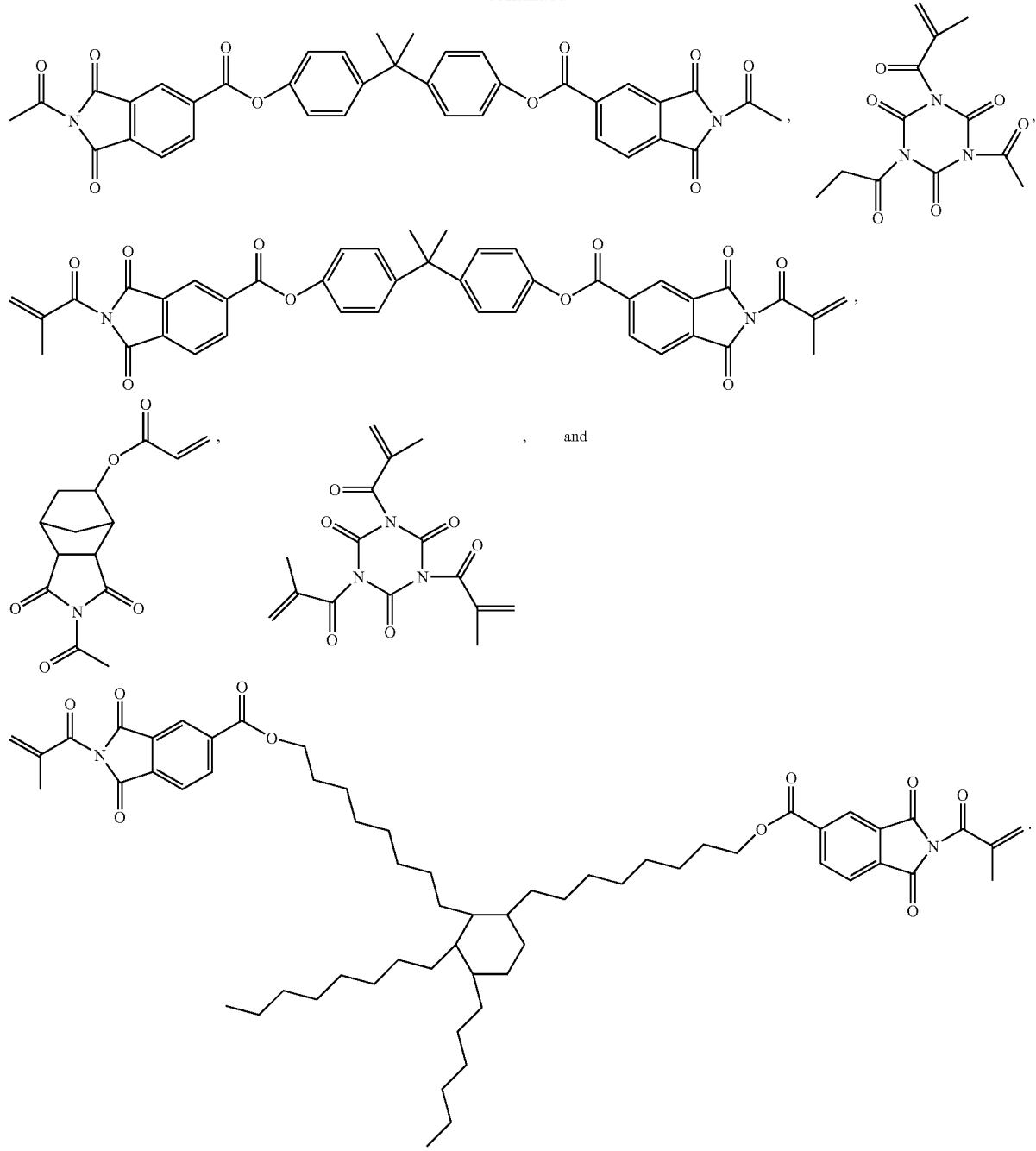

The present invention also provides compositions that include an epoxy or oxetane resin and one or more of the curatives described above. In certain embodiments, the epoxy includes at least one of a glycidyl ether epoxy, a cycloaliphatic epoxy, and an aliphatic epoxy. The glycidyl ether epoxy can be, for example, a glycidyl ether of a phenol, an amine, an alcohol, or an isocyanurate; a trisglycidyl ether of a phenolic compound; a glycidyl ether of a cresol formaldehyde condensate; a glycidyl ether of a phenol formaldehyde condensate; a glycidyl ether of a cresol dicyclopentadiene addition compound; a glycidyl ether of a phenol dicyclopentadiene addition compound; a glycidyl ether of a fused ring polyaromatic phenol; a diglycidyl ether; a glycidyl ether of an aliphatic alcohol; a glycidyl ether of a polyglycol; a glycidyl derivative of an aromatic amine; an ester linked epoxy; a phenyl glycidyl ether; a cresyl glycidyl ether; a nonylphenyl glycidyl ether; a p-tert-butylphenyl glycidyl ether; a diglycidyl ether or a trisglycidyl ether of bisphenol A, bisphenol F, ethylidinebisphenol, dihydroxydiphenyl ether, N,N'-disalicylal-ethylenediamine, triglycidyl-p-aminophenol, N,N,N',N'-tetraglycidyl-4,4'-diphenylmethane, triglycidyl isocyanurate, bis(4-hydroxyphenyl)sulfone, bis(hydroxyphenyl)sulfide, 1,1-bis(hydroxyphenyl)cyclohexane, 9,19-bis(4-hydroxyphenyl)fluorene, 1,1,1-tris(hydroxyphenyl)ethane, trihydroxytritylmethane, 4,4'-(1-alpha-methylbenzylidene)bisphenol, 4,4'-(1,2 ethylene)diphenol, stilbesterol, 4,4'-dihydroxybenzophenone, resorcinol, catechol, or tetrahydroxydiphenyl sulfide; a glycidyl ether of a dihydroxy naphthalene, 2,2'-dihydroxy-6,6'-dinaphthyl disulfide, or 1,8,9-trihydroxyanthracene; a diglycidyl ether of 1,4 butanediol; a diglycidyl ether of diethylene glycol; a diglycidyl ether of neopentyl glycol; a diglycidyl ether of cyclohexane dimethanol; a diglycidyl ether of tricyclodecane dimethanol; a trimethyolethane triglycidyl ether; a glycidyl ether; a trimethyol propane triglycidyl ether; Heloxy 84™; Heloxy 32™; a polyglycidyl ether of castor oil; polyoxypropylene diglycidyl ether; Heloxy 71™; and/or glycidyl methacrylate.

In certain embodiments, the cycloaliphatic epoxy ether can include a cyclohexene oxide; a 3-vinylcyclohexene oxide; a vinylcyclohexene dioxide; a dicylcopentadiene dioxide; a tricyclopentadiene dioxide; a tetracyclopentadiene dioxide; a norbornadiene dioxide; a bis(2,3-epoxycyclopentyl)ether; a limonene dioxide; 3',4'-epoxycyclohexamethyl-3,4-epoxycyclohexanecarboxylate; a 3,4-epoxycyclohexyloxirane; a 2(3',4'-epoxycyclohexyl)-5,1"-spiro-3",4"-epoxycyclohexane-1,3-dioxane; and/or a bis(3,4-epoxycyclohexamethyl) adipate.

In other embodiments, the aliphatic epoxy can include an epoxidized polybutadiene; an epoxidized polyisoprene; an epoxidized poly(1,3-butadiene-acrylonitrile); an epoxized soybean oil; an epoxidized castor oil; a dimethylpentane dioxide; a divinylbenzene dioxide; a butadiene dioxide; and/or a 1,7-octadiene dioxide.

The compositions of the invention include compositions useful as adhesives, coatings, matrix resins and composite resins. In certain embodiments, the composition is a die attach paste adhesive that includes a filler. In other embodiments, the composition is an encapsulant such as electronic mold compound or underfill that includes a filler. In other embodiments, the composition is an industrial or marine coating or adhesive that includes a filler, an extender and/or a pigment.

Also contemplated by the invention are compositions including industrial, marine, automotive, airline, aerospace, sporting goods, medical and dental matrix resins. In yet other aspects of the invention, the compositions can be composite resins that include for example, carbon fiber, fiberglass and/or silica.

Certain compositions of the invention, such as adhesives, can also include additional compounds such as acrylates, methacrylates, maleimides, vinyl ethers, vinyl esters, styrenic compounds, allyl functional compounds, phenols, anhydrides, benzoxazines, and oxazolines.

The present invention also provides assemblies that include a first article adhered to a second article by a cured aliquot of the adhesive composition described above. Also provided are articles of manufacture coated with a cured layer of one of the compositions described above, such as a watercraft, automobile or airplane parts. In other embodiments of the invention, articles of manufactures can be comprised of a cured amount of a composition described herein, such as an encapsulant, industrial, marine, automotive, airline, aerospace, sporting goods, medical or dental article. Such articles of manufacture can also include fillers, extenders, pigments and/or reinforcing materials along with the compositions disclosed herein.

Method for attaching a first article to a second article are also provided by the invention, including the steps of applying an adhesive composition as disclosed above to the first article, the second article, or both the first article and the second article; then contacting the first article and second article, such that the first article and the second article are separated only by the adhesive composition, which results in the formation of an assembly. Upon curing of the adhesive composition, the first article is adhesively attached to the second. In certain embodiments, the adhesive composition includes a free-radical curable monomer and curing is by a hybrid thermosetting and free-radical cure.

The present invention also provides methods for adhesively attaching a semiconductor die to a substrate including the steps of applying the adhesive composition of the invention to the substrate, the semiconductor die, or the substrate and the semiconductor die; contacting the substrate and the die, such that the substrate and the die are separated only by the adhesive composition, to form an assembly; and then curing the adhesive composition, which results in adhesively attaching the semiconductor die to the substrate. In certain embodiments, the adhesive composition includes a free-radical curable monomer and curing is by a hybrid thermosetting and free-radical cure.

The present invention also contemplates use of the acyl curatives described above in methods for increasing the adhesion, decreasing the viscosity, decreasing the modulus, reducing weight loss, and decreasing the hydrophilicity of an epoxy or oxetane resin, by combining an acyl curative of invention with the epoxy or oxetane resin.

DETAILED DESCRIPTION

Figure 1:
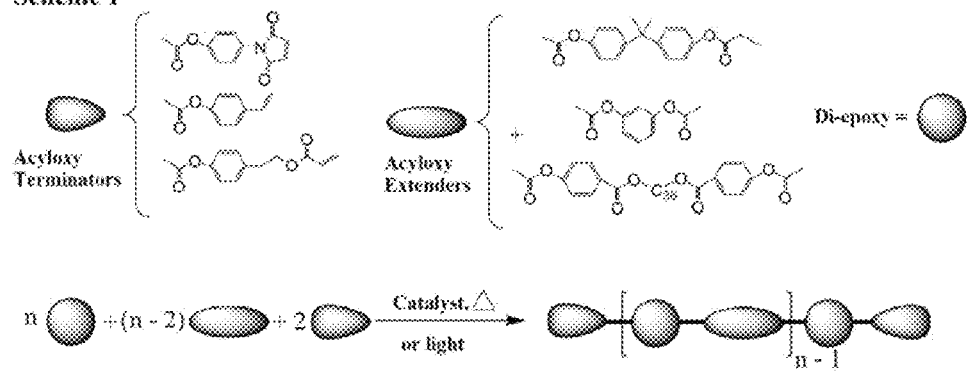
FIG. 1 shows a scheme for the first step of a b-staging procedure represented by a chain extension and termination sequence.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

The invention provides novel acetoxy, acyloxy, and N-acyl curing agents useful in a variety of epoxy adhesive formulations. As used herein, "acyloxy" refers compounds having at least one moiety of the following general structure:

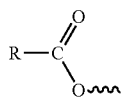

"Acetoxy", according to the present invention, refers to compounds having at least one moiety of the following general structure:

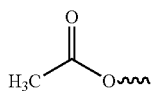

"N-acyl", according to the present invention, refers to compounds having at least one moiety of the following general structure:

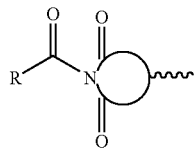

According to one embodiment of the invention, epoxy curing agents having the structure of Formulae I and II, below, are provided:

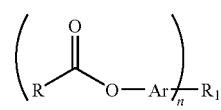
I

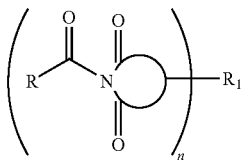
II wherein each of R and $R_1$ is, independently, a substituted or an unsubstituted aliphatic, heteroaliphatic, aromatic, heteroaromatic, siloxane, maleimido, or cinnamyl moiety; Ar is a substituted or an unsubstituted aryl or heteroaryl moiety having between 6 and about 20 carbon atoms; and n is an integer having the value between 1 and about 11, such as between 1 and 6, for example, between 2 and 6.

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated.

In certain aspects of the invention, each of R and $R_1$ is, independently, a substituted or an unsubstituted alkyl, cycloalkyl, alkenyl, aryl, or heterocyclic moiety. According to some embodiments, at least one of R and $R_1$ is a $C_1$ to about $C_{20}$ substituted or unsubstituted alkyl, cycloalkyl, alkenyl, or aryl moiety. In other aspects, R and $R_1$ are each independently substituted or unsubstituted siloxane or maleimide.

In yet other embodiments, Ar is a substituted or an unsubstituted $C_6$ to about $C_{11}$ aryl or heteroaryl. In still further embodiments, Ar is phenyl, benzyl, tolyl, or xylyl.

In some embodiments, the value of n is between 2 and about 10, or between 4 and about 8. While in still further embodiments, the value of n is between 1 and 6.

As used herein, "alkyl" refers to straight or branched chain hydrocarbyl groups having between 1 and about 500 carbon atoms.

"Substituted alkyl" refers to alkyl moieties bearing substituents including, but not limited to, an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —C(O)—, —C(O)O—, —S—, —S(O)$_2$—, —OC(O)O—, —NR—C(O)—, —NR—C(O)—NR—, —OC(O)—NR—, wherein R is H, a lower alkyl, an acyl, an oxyacyl, carboxyl, carbamate, sulfonyl, sulfonamide, and sulfuryl.

As used herein, "alkenyl" refers to straight or branched chain hydrocarbyl groups having at least one carbon-carbon double bond, and having between 2 and about 500 carbon atoms, and "substituted alkenyl" refers to alkenyl groups further bearing one or more substituents as set forth above.

As used herein, "cycloalkyl" refers to cyclic ring-containing groups typically containing between 3 and about 20 carbon atoms, and "substituted cycloalkyl" refers to cycloalkyl groups further bearing one or more substituents as set forth above.

As used herein, "aryl" refers to aromatic groups having between 6 and about 20 carbon atoms. "Substituted aryl" refers to aryl groups further bearing one or more substituents as set forth above. "Heteroaryl" refers to aryl groups having one or more heteroatoms (e.g., N, O, and S) as part of the ring structure.

As used herein, "heterocyclic" refers to cyclic (i.e., ring-containing) groups containing one or more heteroatoms (e.g., N, O, and S) as part of the ring structure, and having in between 3 and about 14 carbon atoms and "substituted heterocyclic" refers to heterocyclic groups further bearing one or more substituents as set forth above. The term heterocyclic is also intended to refer to heteroaromatic moieties.

As used herein, "siloxane" refers to any compound containing a Si—O moiety. In certain embodiments, siloxanes of the invention include 2 or more repeating units of Si—O.

As used herein, the term "maleimido" refers to a compound bearing at least one moiety having the structure:

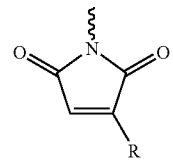

wherein R is H or lower alkyl.

"Imide" as used herein, refers to a functional group having two carbonyl groups bound to a primary amine or ammonia. The general formula of an imide of the invention is:

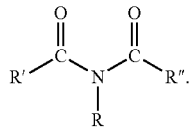

"Maleimide," as used herein, refers to an N-substituted maleimide having the formula as shown below:

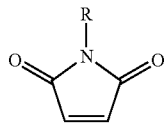

wherein R group may be an aromatic, heteroaromatic, aliphatic, or polymeric moiety.

"Polyimides" are polymers of imide-containing monomers. Polyimides typically have one of two forms: linear or cyclic. Non-limiting examples of linear and cyclic (e.g. an aromatic heterocyclic polyimide) polyimides are shown below for illustrative purposes.

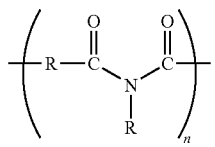

Linear Polyimide

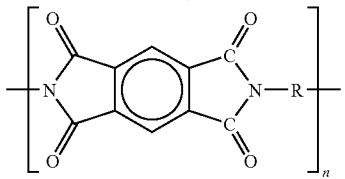

Aromatic Heterocyclic Polyimide

As used herein, the term "acrylate" refers to a compound bearing at least one moiety having the structure:

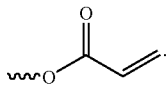

As used herein, the term "acrylamide" refers to a compound bearing at least one moiety having the structure:

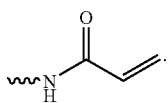

As used herein, the term "methacrylate" refers to a compound bearing at least one moiety having the structure:

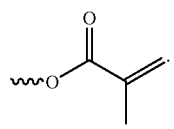

As used herein, the term "methacrylamide" refers to a compound bearing at least one moiety having the structure:

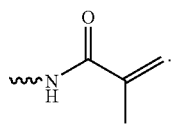

As used herein "epoxy" refers to a thermosetting epoxide polymer that cures by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

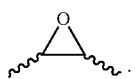

As used herein, the term "oxetane" refers to a compound bearing at least one moiety having the structure:

"Thermoplastic," as used herein, refers to the ability of a compound, composition or other material (e.g. a plastic) to melt to a liquid when heated, and freeze to solid, often brittle and glassy, state when cooled sufficiently.

"Thermoset," as used herein, refers to the ability of a compound, composition or other material to irreversibly "cure" to a stronger, harder form. Thermoset materials are typically polymers that may be cured, for example, through heat (e.g. above 200° C., or in the presence of appropriate catalysts at lower temperatures), via a chemical reaction (e.g. epoxy), or through irradiation (e.g. U.V. irradiation).

Thermoset materials, such as thermoset polymers or resins, are typically liquid or malleable forms prior to curing, and therefore may be molded or shaped into their final form, and/or used as adhesives. Curing transforms the thermoset resin into an infusible solid or rubber by a cross-linking process. Thus, energy and/or catalysts are added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

A "die" as used herein, refers to a small block of semiconducting material, on which a functional circuit is fabricated.

The acyl-containing moiety of curatives described herein can be varied considerably in the practice of the invention. Exemplary acyloxy (—OC(O)R) moieties are set forth below:

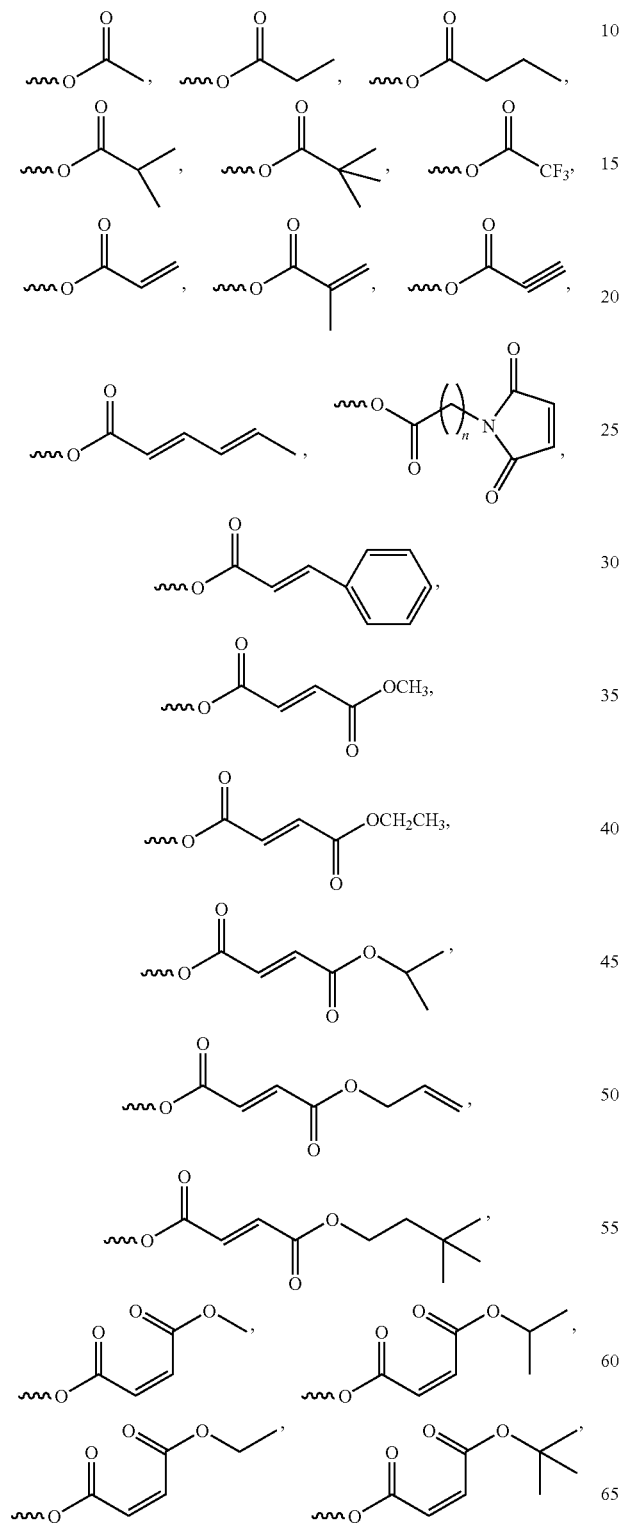

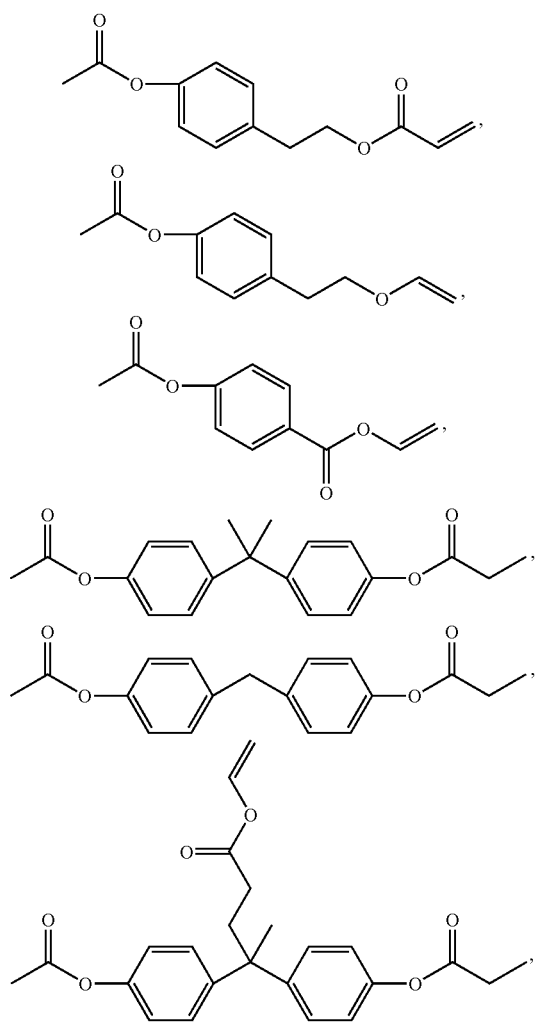

wherein n is an integer having the value between 1 and 11. Exemplary invention curing agents include:

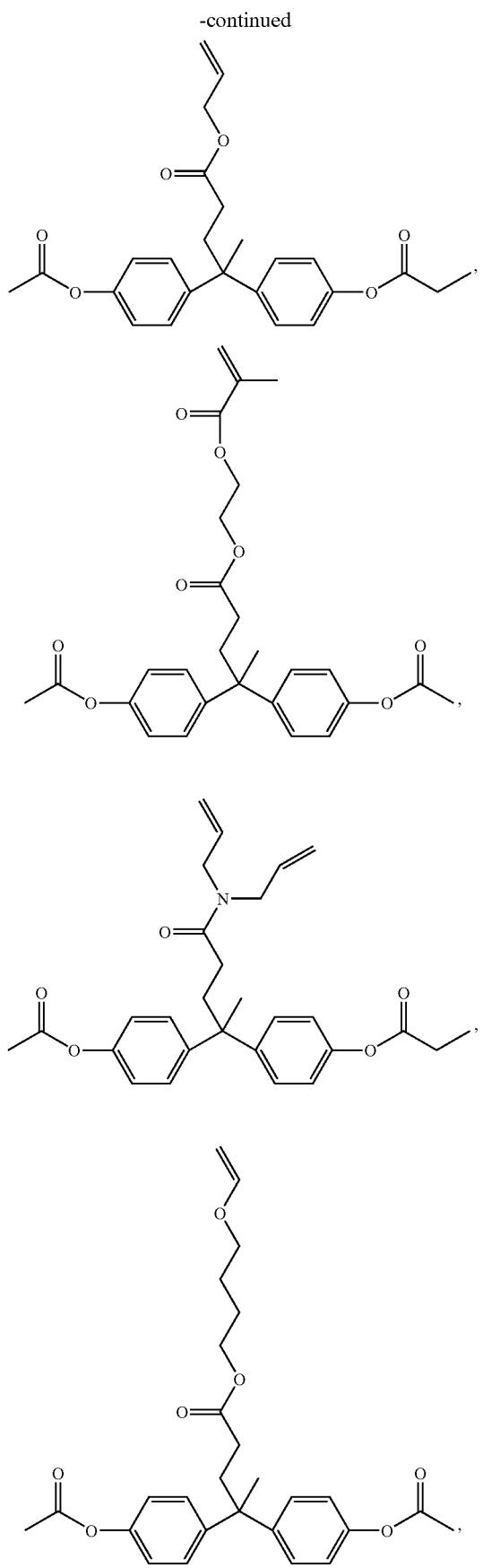

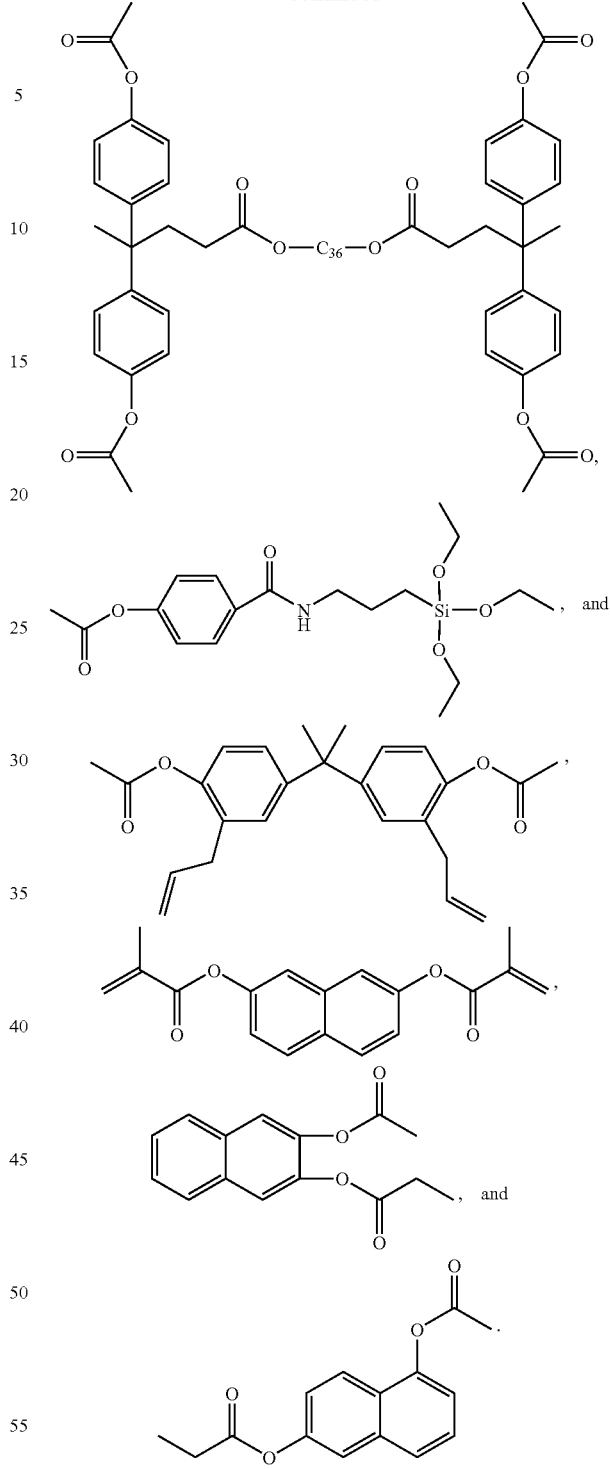

Dual functional acyloxy compounds of the present invention can be used to create new end-functionalized, monomers and oligomers through chain extension. Thus, according to one embodiment of the invention, a difunctional epoxy and a bisacyloxy compound can be reacted to form a linear oligomer. The oligomers can be chain terminated with a monoacyloxy compound that also bears an independently polymerizable functional group. Where the end group is an acrylate, methacrylate, maleimide, citraconimide, diallylamide, vinyl ester, styrenyl, or other free radically polymerizable moiety, the oligomers can then be converted to a cross-linked thermoset in a second step. This dual stage cure is especially attractive for applications were it is desirable to apply an adhesive in liquid form, cure the material to a non-tacky thermoplastic state, and then cure this b-staged adhesive in a final heating step to bond two or more parts together.

Figure 2:
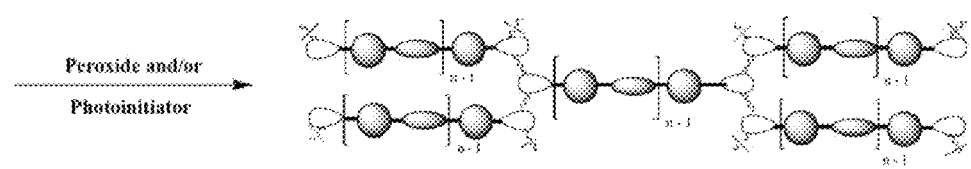
FIG. 2 shows a scheme for the final step in a b-staging procedure, which involves a thermal cure to cross-link b-staged functional oligomers.

This dual stage cure method of the invention is particularly attractive for silicon wafer back coatings. The original mix of difunctional epoxies, difunctional acyloxy compounds, and suitably substituted mono-acyloxy compounds (along with coupling agents, catalysts, and optionally fillers) can be spin coated onto the back of a silicon wafer. The coating can then be b-staged with heat or light. The b-staging step can be represented by the chain extension and termination sequence shown in Scheme 1 (FIG. 1). The coated wafers can then be diced to yield individual microelectronic components, which may be thermally attached directly to a substrate, and/or stacked together. The thermal "tacking step" re-liquifies the oligomeric coating and provides a thermoplastic bond between the parts. The final bonding step involves a thermal (or in some cases light-based) cure to cross-link the b-staged functional oligomers as shown in Scheme 2 (FIG. 2). This method of assembly is desirable because it is easier to manufacture (especially for stacked die) than a traditional liquid adhesive assembly, and is less expensive and wasteful compared to film-based adhesive technology.

Poly-acyloxy curatives are also contemplated for use in the practice of the invention. These are especially suited for pre-applied and/or film applications. Indeed, any novolak can be converted to a poly-acyloxy compound, and therefore a vast array of poly-acyloxy curatives are contemplated, including but not limited to those shown below.

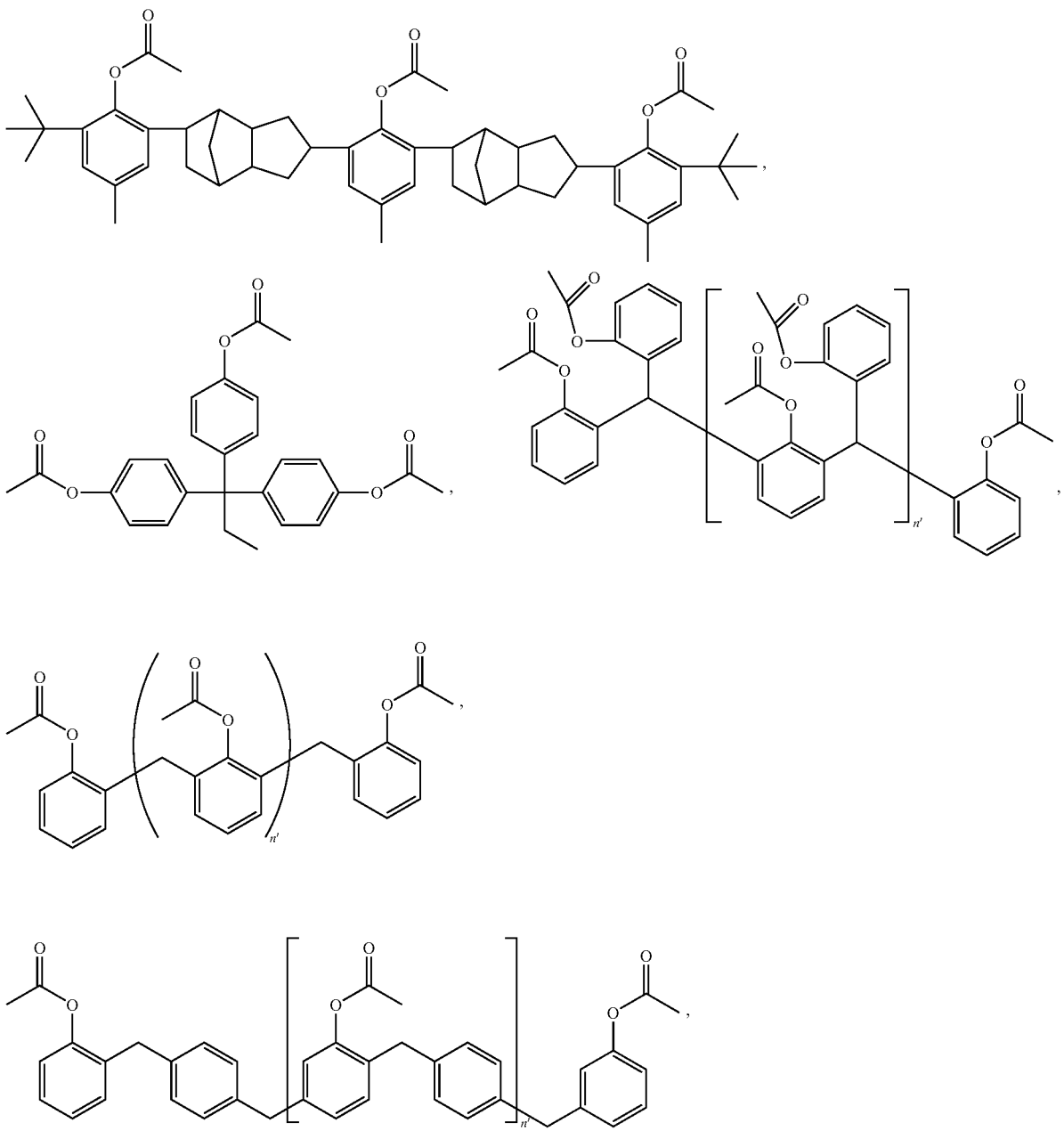

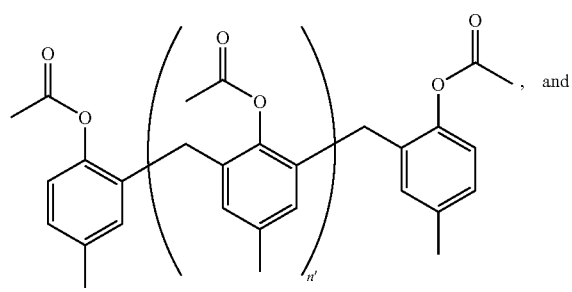, and
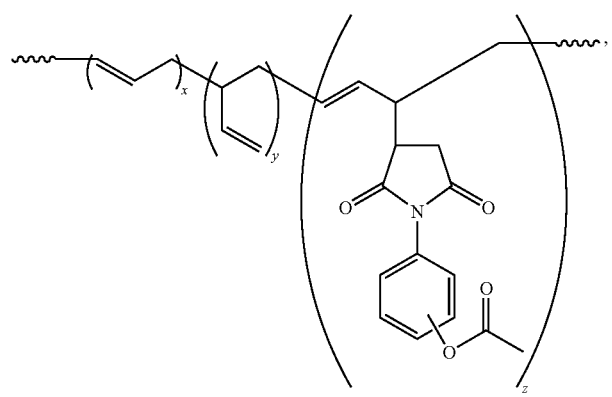,
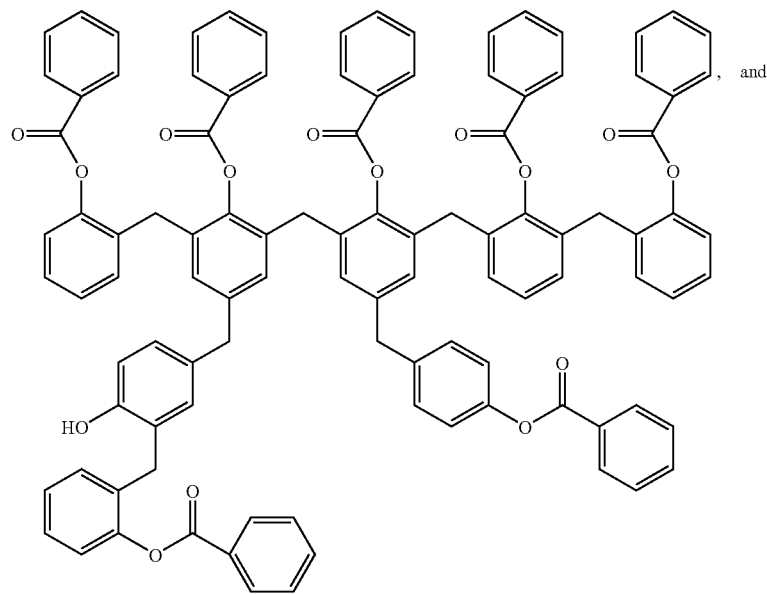, and

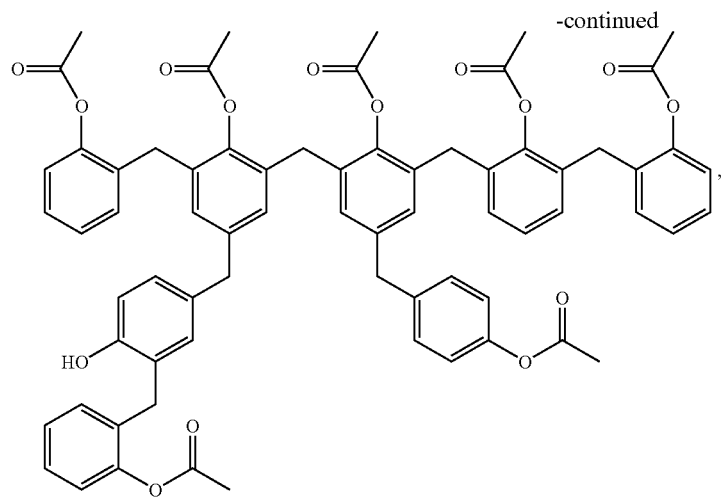
wherein each of n', x, y and z is an integer, independently having the following values: n' between 0 and 10, each of x and y between 4 and about 50, and z between 2 and about 40.
Referring now to Formula II, above, the substituent R can be varied considerably in the practice of the invention. Exemplary N-acyl moieties include but are not limited to:
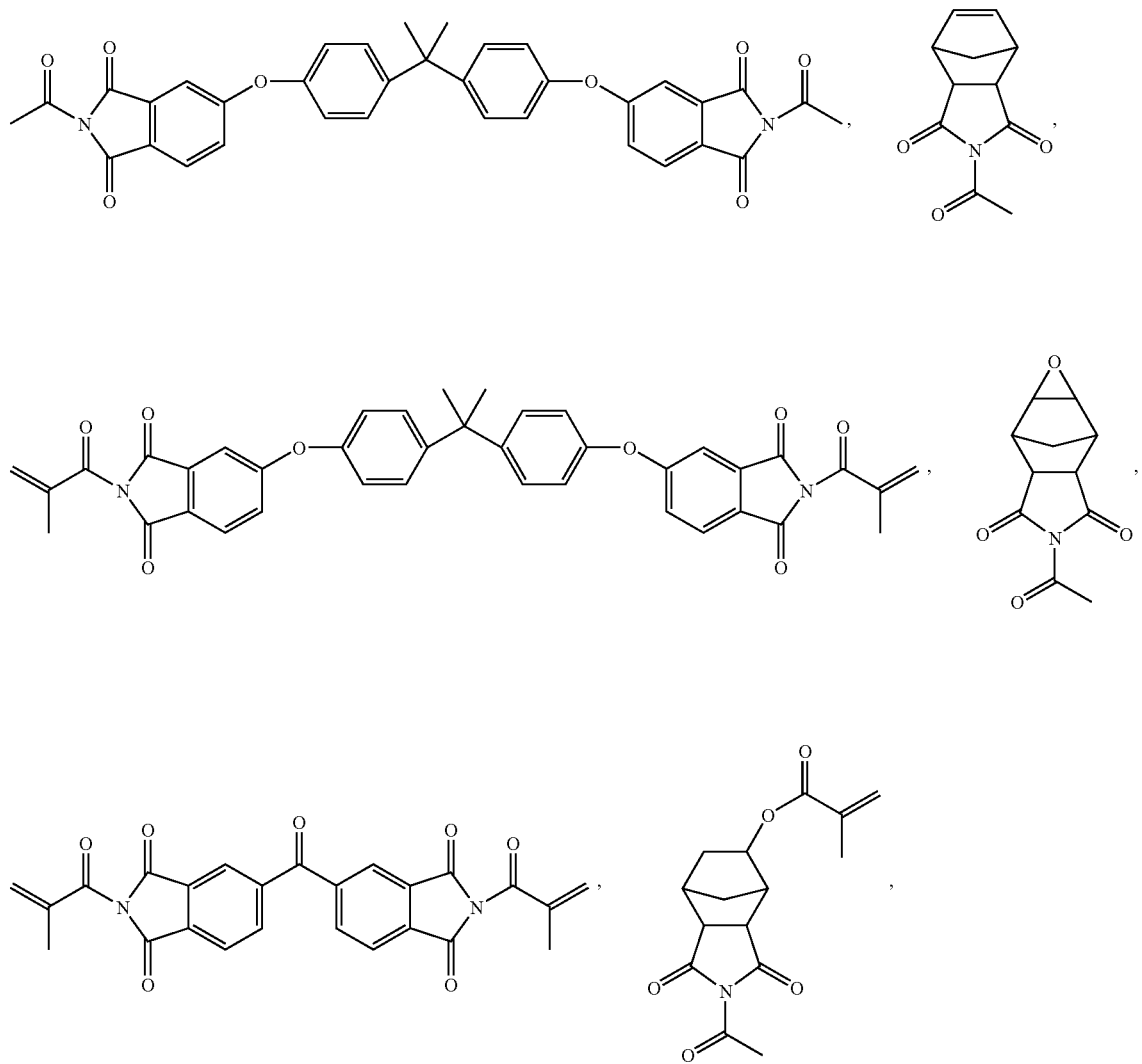

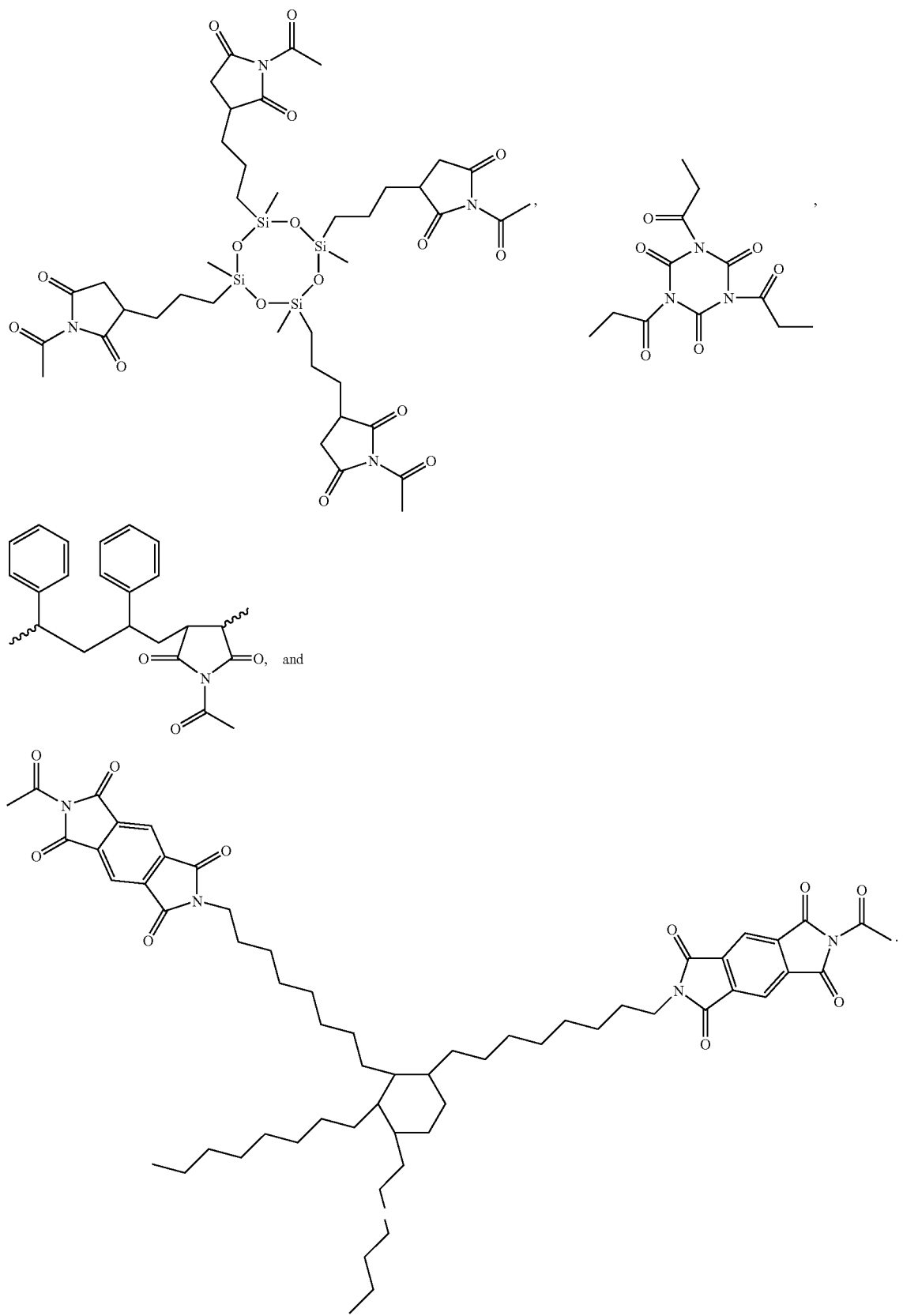

Additional exemplary invention curing agents are set forth below:
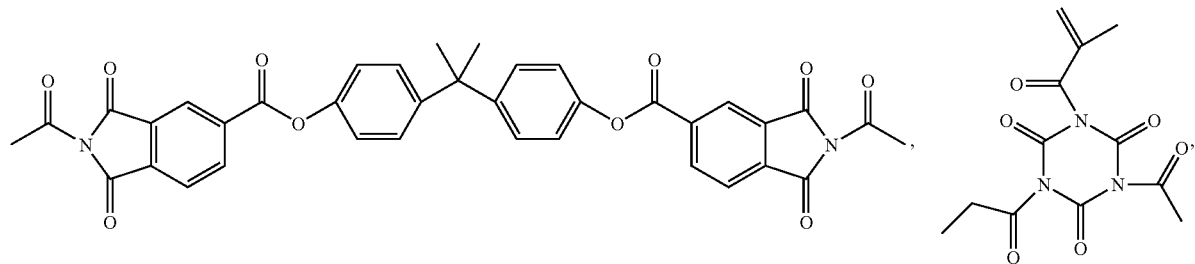
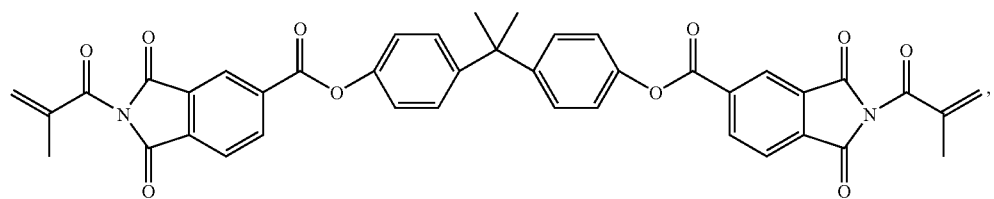
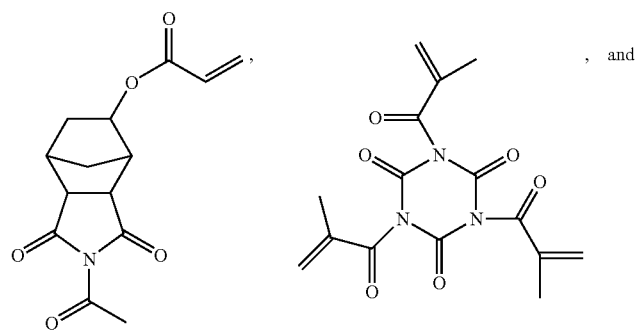, and
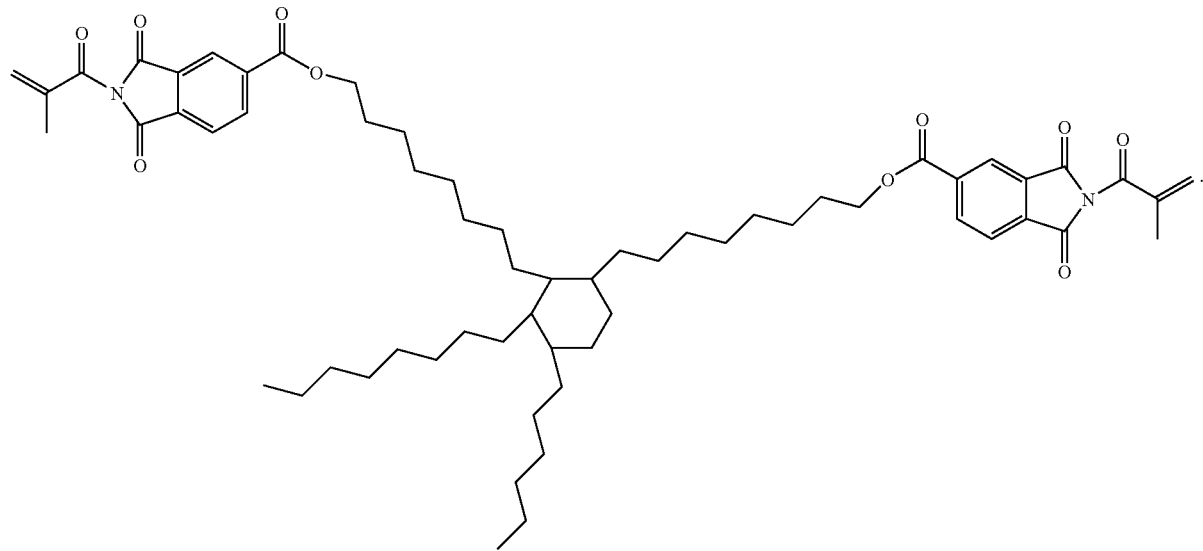

Poly-N-acyl curatives are also contemplated for use in the practice of the invention. These are especially suited for pre-applied and/or film applications. Indeed, any polymer containing anhydride residues in the main-chain or grafted to the backbone can be converted to a poly-N-acyl compound, and therefore a vast array of poly-N-acyl curatives are contemplated, including, but not limited to those illustrated below.

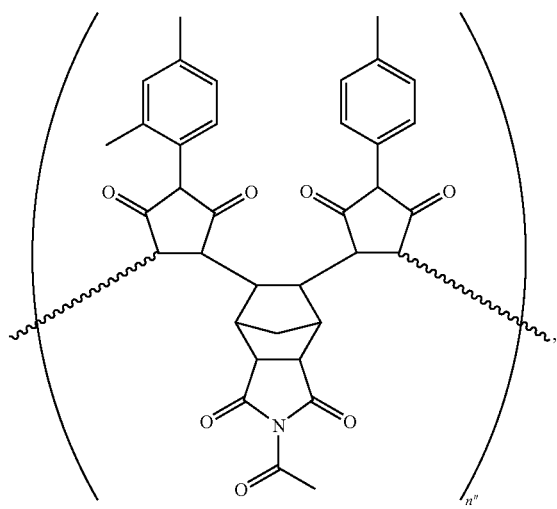

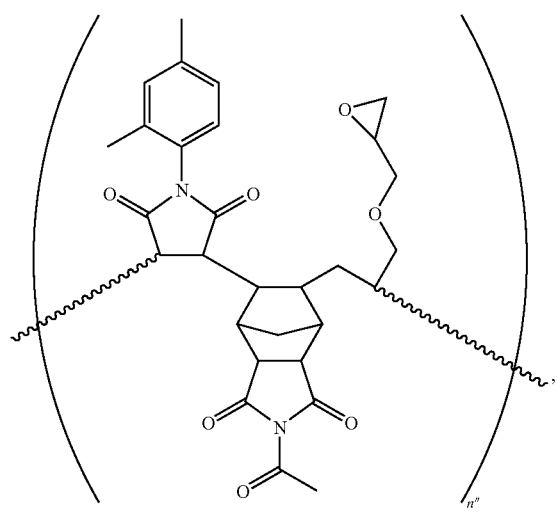

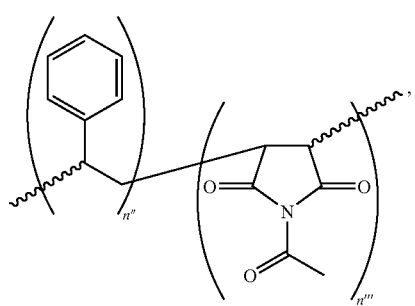

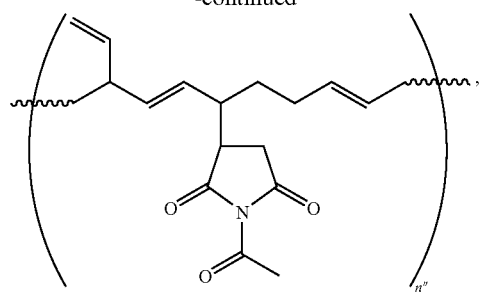

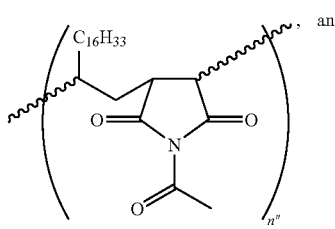

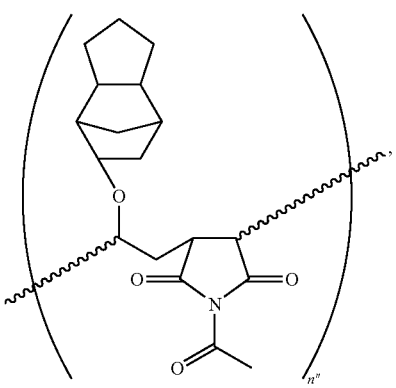

wherein each n'' and n''' is an integer independently having the value between 1 and about 10.

The compounds set forth below provide representative, non-limiting examples of phenyl acyloxy derivatives that have additional useful functionality. In some cases these compounds can be used to make high $T_g$, linear, segments within a thermoset (i.e. where the molecule bears both epoxy and acyloxy functionality). The maleimide functional compounds can be used to make polymaleimides in situ, which would be available to participate in the rich cure chemistry of polymaleimides (ene/Diels-Alder, Michael addition, free-radical, etc.). It should be noted that most of these compounds are shown as their phenyl acetates, however any of the previous acyloxy moieties are contemplated for use in this embodiment of the invention. In some embodiments, the isopropenyl compounds could be used for ene/Diels-Alder cures of BMIs.

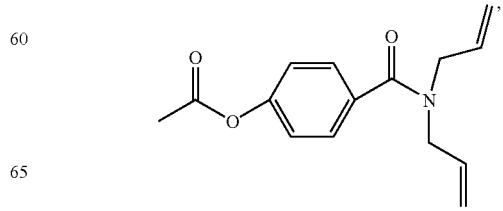

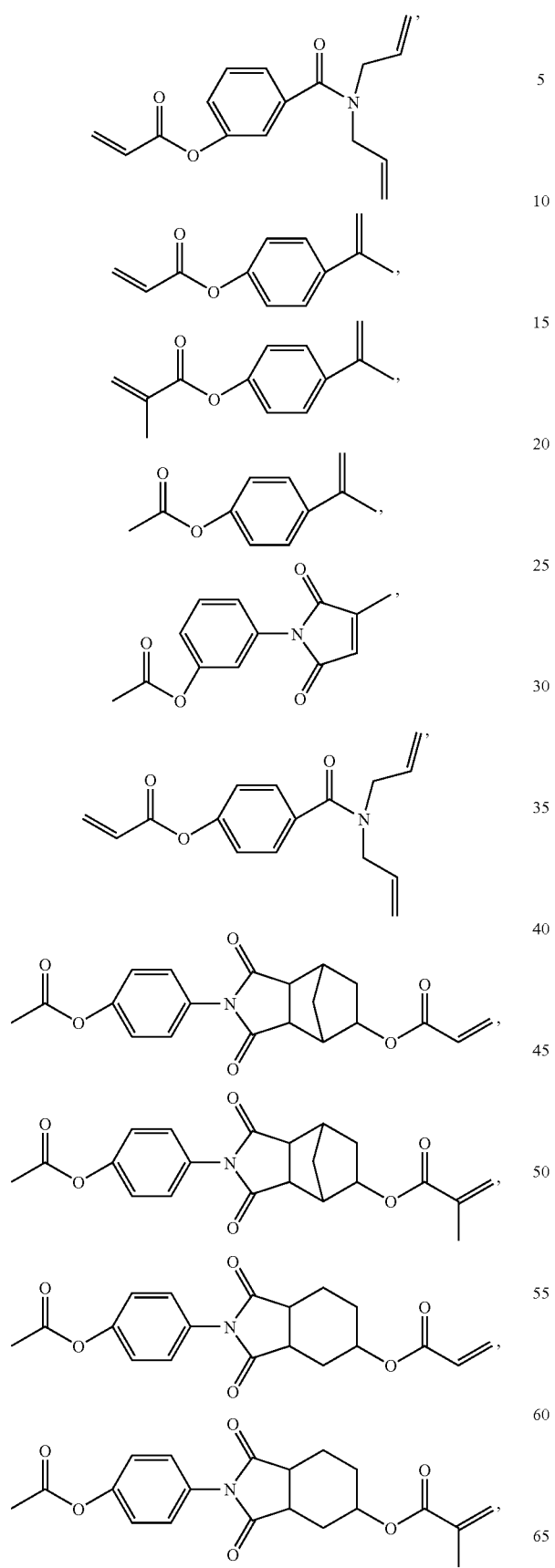
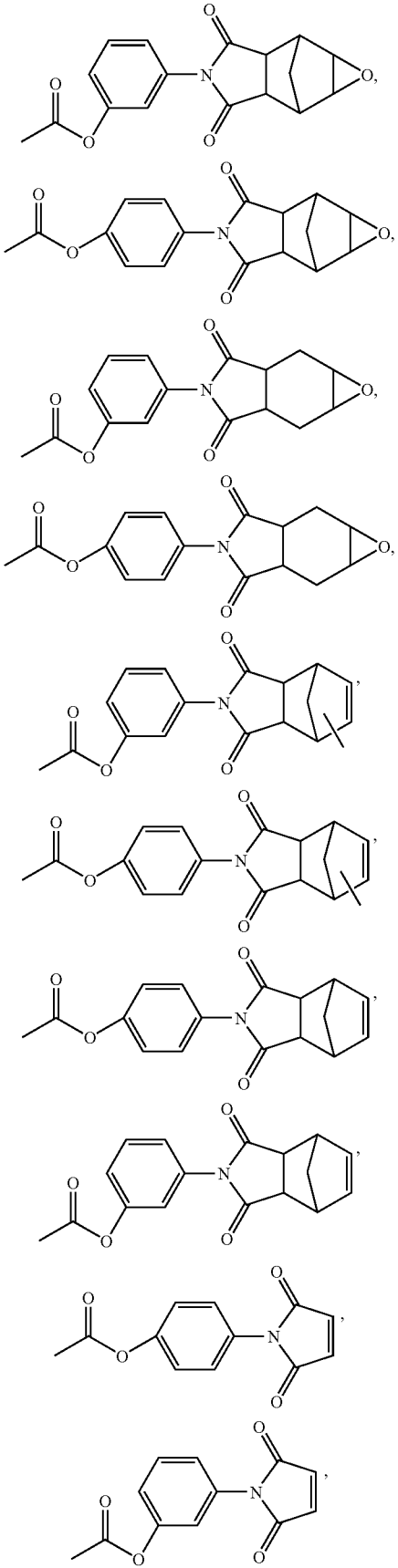

47
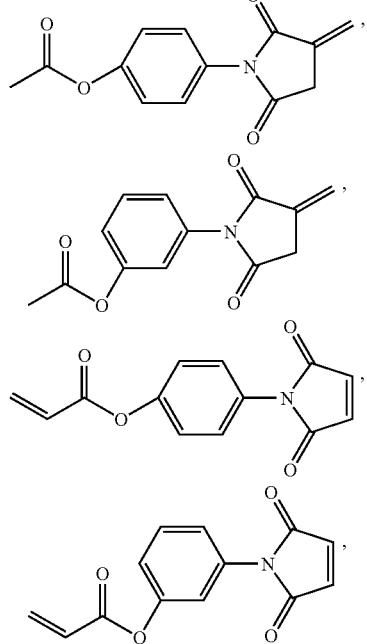
48
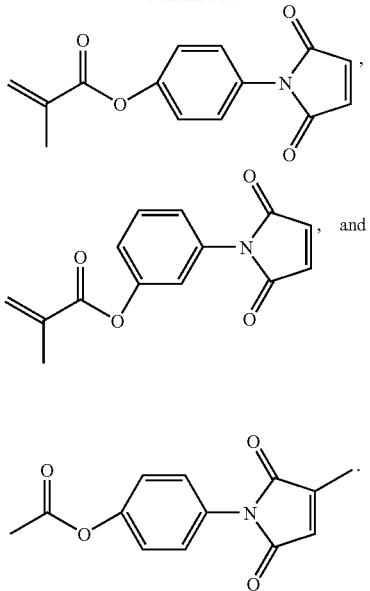
The compounds set forth below are liquids and would therefore be suited for use in paste based adhesives.
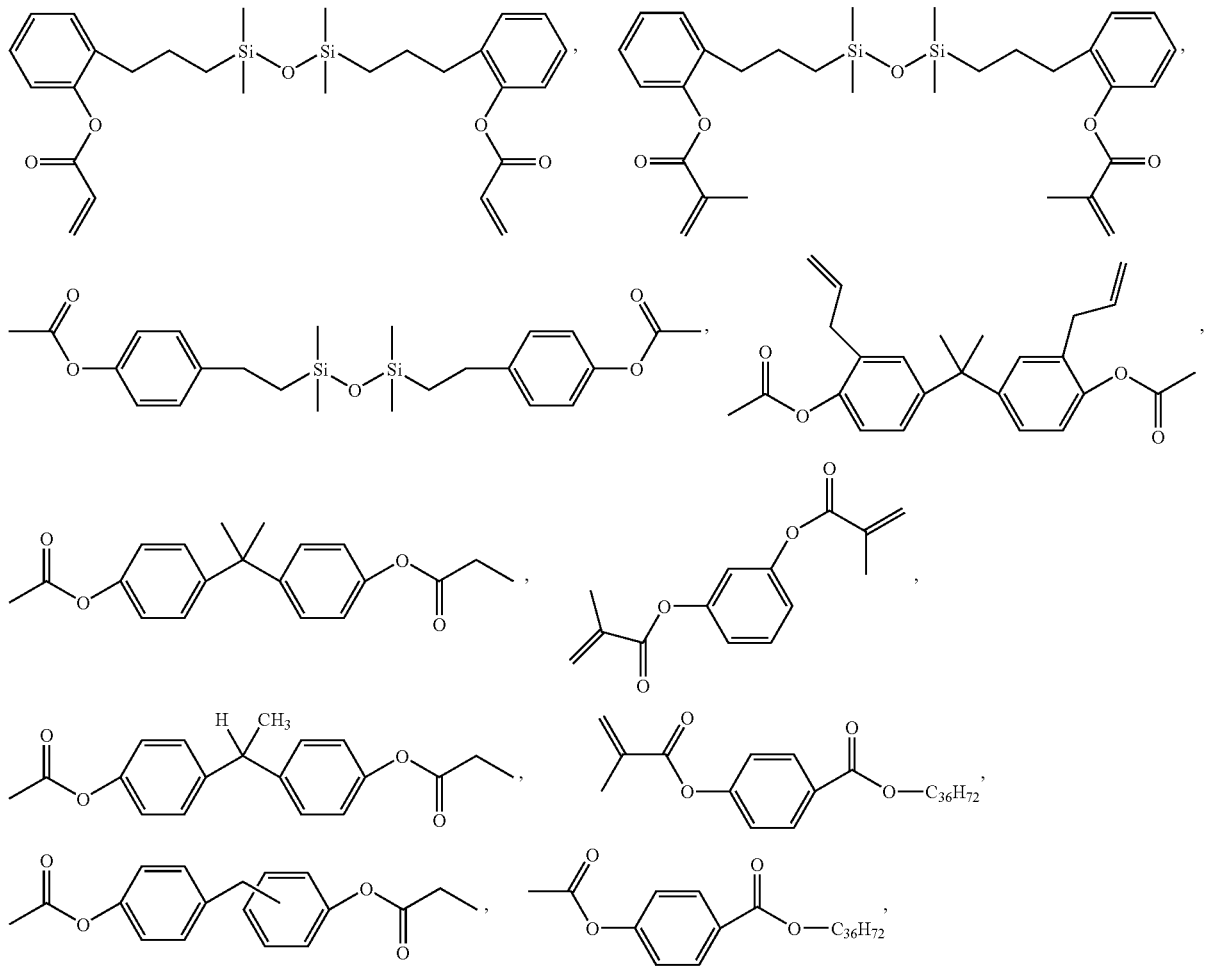

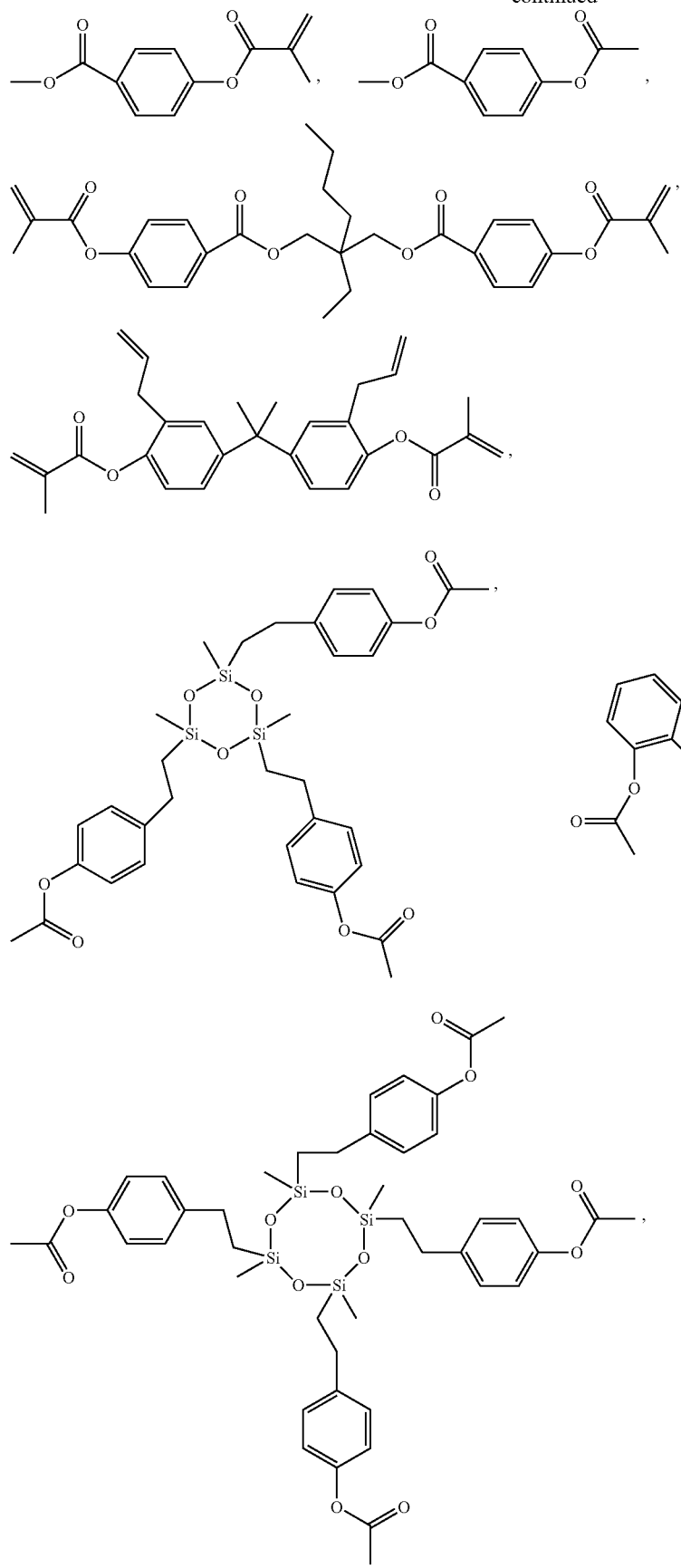

51
52
-continued
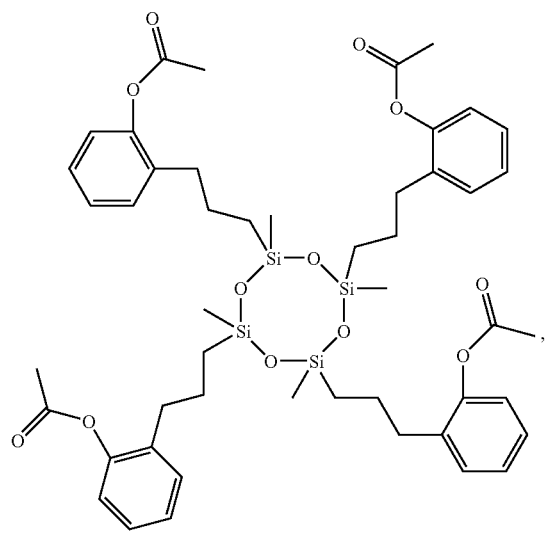
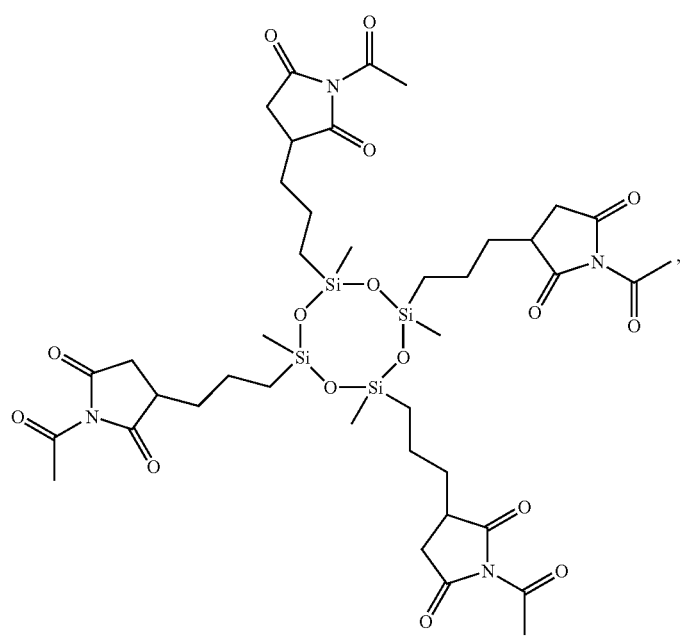
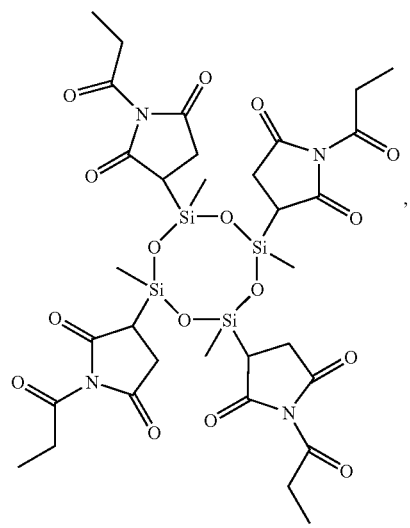

-continued
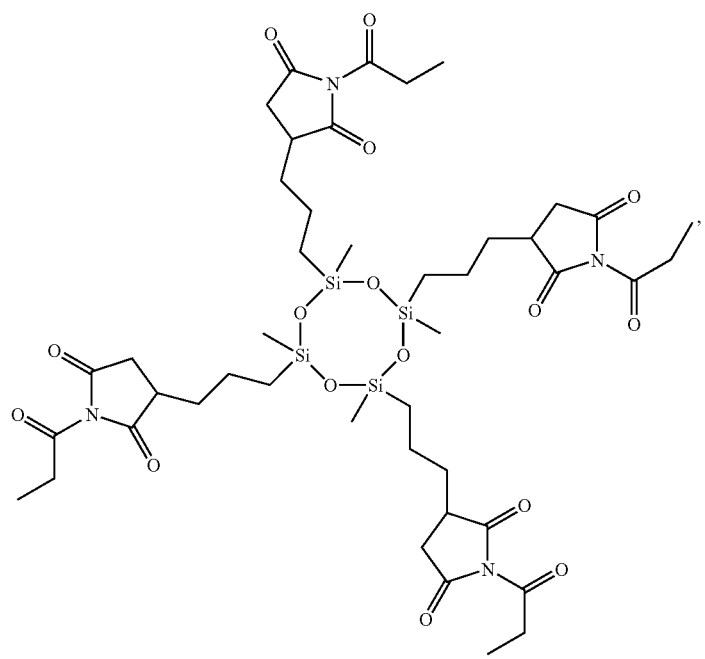
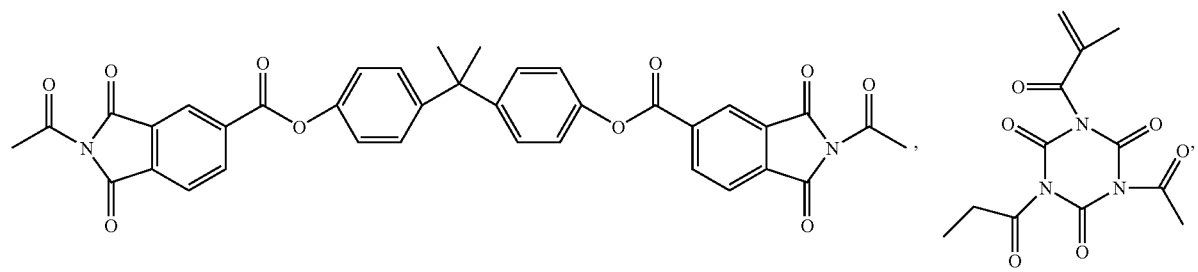
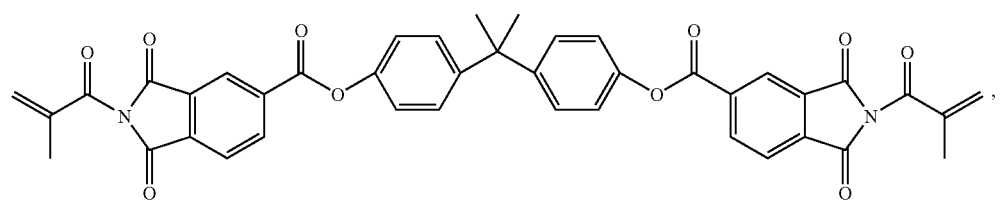
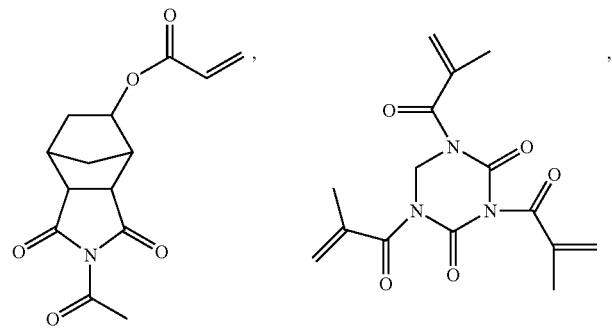

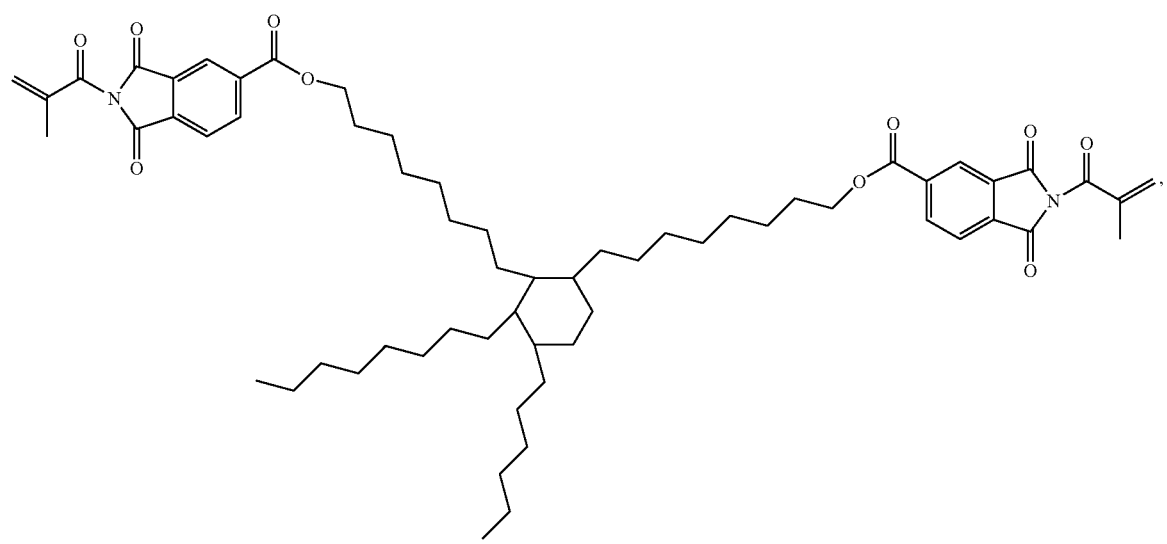
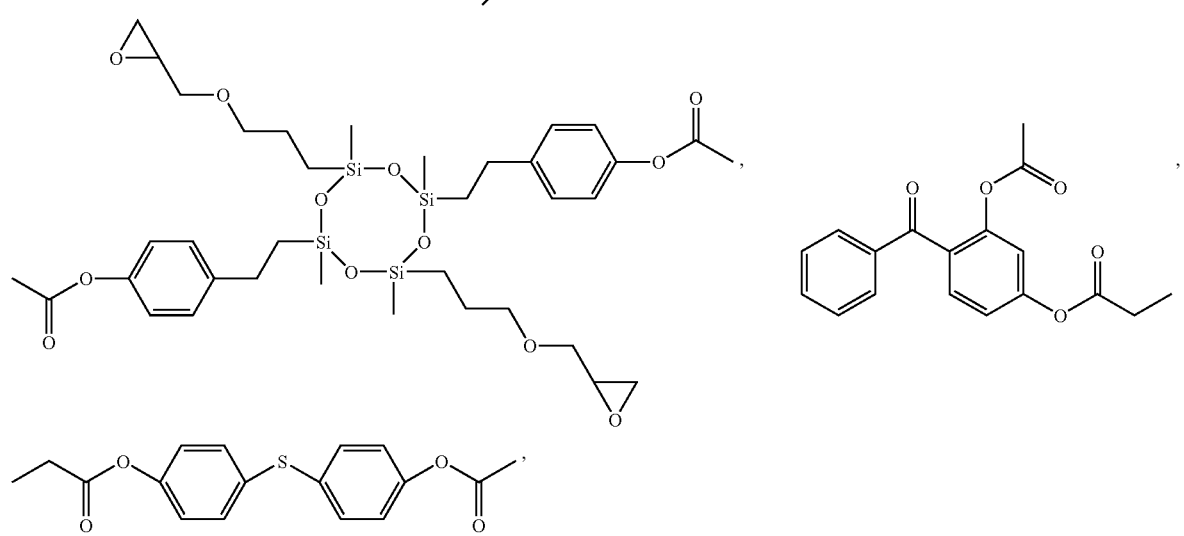
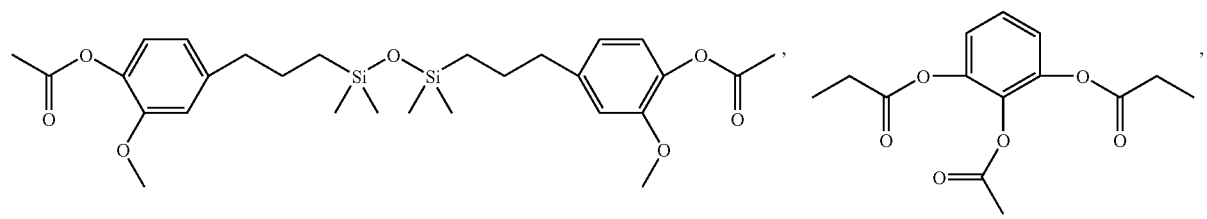
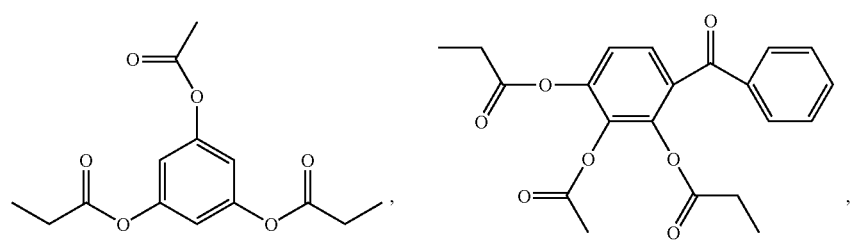

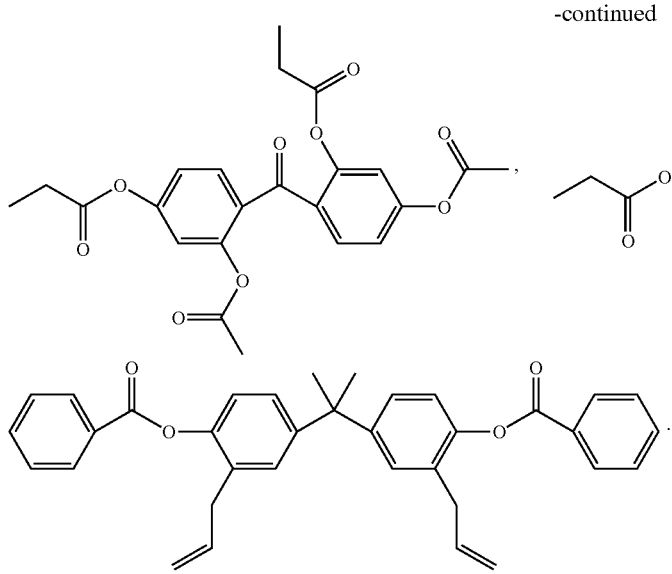

Epoxy resins contemplated for use in the practice of the invention include, but are not limited to, aliphatic, cycloaliphatic, glycidyl ether, glycidyl ester, glycidyl amine epoxies.

Glycidyl ether epoxy resins contemplated for use in the practice of the invention include, but are not limited to, a glycidyl ether of a phenol, an amine, an alcohol, or an isocyanurate, such as a phenyl glycidyl ether, a cresol glycidyl ether, a nonylphenyl glycidyl ether, and a p-tert-butylphenyl glycidyl ether; a diglycidyl ether or a trisglycidyl ether of a phenolic compound such as bisphenol A, bisphenol F, ethylidinebisphenol, dihydroxydiphenyl ether, N,N'-disalicylal-ethylenediamine, triglycidyl-p-aminophenol, N,N,N',N'-tetraglycidyl-4,4'-diphenylmethane, triglycidyl isocyanurate, bis(4-hydroxyphenyl)sulfone, bis(hydroxyphenyl)sulfide, 1,1-bis(hydroxyphenyl)cyclohexane, 9,19-bis(4-hydroxyphenyl)fluorene, 1,1,1-tris(hydroxyphenyl)ethane, trihydroxytritylmethane, 4,4'-(1-alpha-methylbenzylidene)bisphenol, 4,4'-(1,2ethylene)diphenol, stilbesterol, 4,4'-dihyroxybenzophenone, resorcinol, catechol, and tetrahydroxydiphenyl sulfide; a glycidyl ether of a cresol formaldehyde condensate; a glycidyl ether of a phenol formaldehyde condensate; a glycidyl ether of a cresol dicyclopentadiene addition compound; a glycidyl ether of a phenol dicyclopentadiene addition compound; a glycidyl ether of a fused ring polyaromatic phenol such as dihydroxy naphthalene, 2,2'-dihydroxy-6,6'-dinaphthyl disulfide, and 1,8,9-trihydroxyanthracene; a glycidyl ether of an aliphatic alcohol such as a diglycidyl ether of 1,4 butanediol, a diglycidyl ether of diethylene glycol, a diglycidyl ether of neopentyl glycol, a diglycidyl ether of cyclohexane dimethanol, a diglycidyl ether of tricyclodecane dimethanol, a trimethyolethane triglycidyl ether, and a trimethyol propane triglycidyl ether; Heloxy 84™, Heloxy 32™, a polyglycidyl ether of castor oil, and a polyoxypropylene diglycidyl ether; a glycidyl derivative of an aromatic amine; ester linked epoxies, such as Heloxy 71™ and glycidyl methacrylate. Other glycidyl ether epoxies contemplated herein include homo- and co-polymers based on allyl glycidyl ether.

Cycloaliphatic epoxy compounds contemplated for use in the practice of the invention include, but are not limited to, cyclohexene oxide; 3-vinylcyclohexene oxide; vinylcyclohexene dioxide; dicylcopentadiene dioxide; tricyclopentadiene dioxide; tetracyclopentadiene dioxide; norbornadiene dioxide; bis(2,3-epoxycyclopentyl)ether; limonene dioxide; 3',4'-epoxycyclohexamethyl-3,4-epoxycyclohexanecarboxylate; 3,4-epoxycyclohexyloxirane; 2(3',4'-epoxycyclohexyl)-5,1"-spiro-3",4"-epoxycyclohexane-1,3-dioxane; bis (3,4-epoxycyclohexamethyl) adipate; and the like.

Aliphatic epoxy compounds contemplated for use in the practice of the invention include, but are not limited to, epoxidized polybutadiene; epoxidized polyisoprene; epoxidized poly(1,3-butadiene-acrylonitrile); epoxized soybean oil; epoxidized castor oil; dimethylpentane dioxide; divinylbenzene dioxide; butadiene dioxide; and 1,7-octadiene dioxide.

As used herein, "b-stageable" means that the adhesive has a first solid phase followed by a tacky rubbery stage at elevated temperature, followed by yet another solid phase at an even higher temperature. The transition from the tacky rubbery stage to the second solid phase is thermosetting. However, prior to that, the material behaves similarly to a thermoplastic material. Thus, such adhesives allow for low lamination temperatures while providing high thermal stability.

The b-stageable adhesive can be dispensed onto a die or a substrate by a variety of methods well known to those skilled in the art. In some embodiments, the adhesive is cast from solution using techniques such as spin coating, spray coating, stencil printing, screen printing, dispensing, and the like.

In certain embodiments, a solvent may be employed in the practice of the invention. For example, when the b-stageable adhesive is spin coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a thixotropic slope of 1.0. In certain embodiments, the solvent or solvent systems used to dispense the b-stageable adhesive have thixotropic slopes ranging from 1.0 to about 5.

In some instances, the b-stageable adhesive is dispensed onto the backside of a die that has been optionally coated with a polyimide. To achieve this goal, in certain embodiments, the solvent system will include a polar solvent in combination with a non-polar solvent. In addition, the polar solvent typically has a lower boiling point than the non-polar solvent. Without wishing to be limited to a particular theory, it is believed that when the adhesive is dispensed and then b-staged, the lower boiling polar solvent escapes first, leaving behind only the non-polar solvent, essentially precipitating the polymer uniformly.

In some embodiments, the solvent or solvent system has a boiling point ranging between about 150° C. up and about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds, which act primarily to modify rheology, include polysiloxanes, silica, fumed silica, fumed alumina, fumed titanium dioxide, calcium carbonate, and the like.

The acyloxy curatives described in this invention can be prepared through a variety of methods known in the art. These synthetic methods include, but are not limited to, the reaction of phenolic compounds with carboxylic acid anhydrides, optionally in the presence of a catalyst. They can be prepared through the reaction of phenols with carboxylic acid chlorides. They may also be prepared via the condensation of phenols and carboxylic acids in the presence of a dehydrating agent, such as N,N'-dicyclohexylcarbodiimide.

The N-acyl curatives of this invention can also be prepared via a number of methods from the corresponding imides. These methods include all of those previously described for the preparation of acyloxy compounds. Thus, the N-acyl compounds may be prepared via the reaction of imides with carboxylic acid anhydrides, optionally in the presence of a catalyst. They can be prepared through the reaction of imides with carboxylic acid chlorides, optionally in the presence of a basic acid acceptor. They can also be made via the direct condensation of an imide and a carboxylic acid in the presence of a dehydrating agent.

The invention will now be further described with reference to the following non-limiting examples.

EXAMPLES

It should be noted that for each of the following exemplary compounds, where the substitution on the backbone is asymmetric or where the molecule has been extended with another bi-functional reactant, that only a single representative structure is shown. That is to say, such compounds are in fact composed of statistical distributions of several molecules. Only the most predominant species in these distributions are shown.

Example 1

Preparation of a Phenol Functional Curative

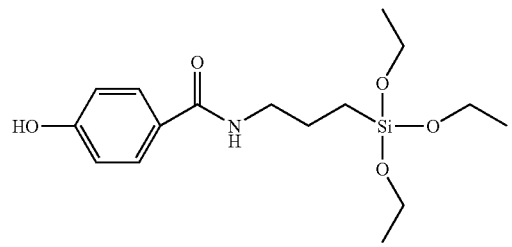 [SMILES: CCO[Si](CCCNC(=O)c1ccc(O)cc1)(OCC)OCC]

A 500 mL, 2-neck flask was charged with 44.27 g (0.2 mole) 3-aminopropyl triethoxysilane, and 20.79 g (0.21 mole) butyl-4-hydroxybenzoate. The flask was equipped with a Dean-Stark trap condenser and bubbler. The mix was then stirred magnetically and heated at 170° C. under an argon blanket for 41.25 hours. Approximately 18.0 mL of butanol was collected in the trap (theoretical yield=18.3 mL). The mix was sparged with argon at 170° C. for 45 min. The product was poured out of the container while still hot. It was a very viscous amber liquid at room temperature. A total of 65.6 g of product was recovered (96.0% of theoretical yield). An FTIR run on this compound had a broad —OH absorbance as well as strong absorptions at 2930, 1688, 1605, 1531, 1270, 1162, 1073, 953, 848, and 769 wavenumbers.

Example 2

Preparation of a Phenyl Acetate Curative/Coupling Agent

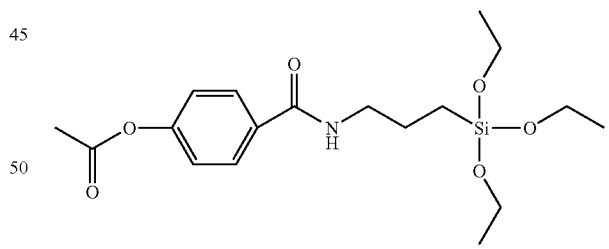

A portion of the compound obtained as described in EXAMPLE 1 was converted to the phenyl acetate shown above. A 250 mL flask was charged with 37.15 g (0.11 mole) of the compound from EXAMPLE 1, 11.02 g (0.11 mole) acetic anhydride, and 0.1 g of dimethylaminopyridine. This mix was heated and stirred at 90° C. for 2 hours. The acetic acid side product was then removed via rotary evaporation and sparge. The final product weighted 40.5 g (97% of theoretical yield). An FTIR spectrum of this material revealed a small amide N—H stretch at 3318 along with prominent absorptions at 2934, 1760, 1639, 1501, 1268, 1198, 1073, 913, and 762 wavenumbers.

Example 3

Comparison of Epoxy Formulations Containing Phenol Functional Curative to the Corresponding Phenyl Acetate The following example demonstrates the remarkably improved adhesion for an epoxy resin cured using an acyloxy coupling agent from EXAMPLE 2, versus the analogous phenol-functional coupling agent from EXAMPLE 1, which does not contain the acyloxy moiety.

TABLE 1

Properties of Epoxy Formulations Containing a Phenol Functional Curative and Corresponding Phenyl Acetate

| Composition | Formulation 1 | Formulation 2 |
| --- | --- | --- |
| Tactix 756 epoxy | 31.6% | 31.6% |
| Ricon | 15.2% | 15.2% |
| Terpineol | 36.7% | 36.7% |
| Curezol 2MA | 1.1% | 1.1% |
| Silica | 1.1% | 1.1% |
| EXAMPLE 1 compound | 2.1% | 0.0% |
| EXAMPLE 2 compound | 0.0% | 2.1% |
| Adhesion*, kg force | | |
| (300 × 300 Si on ceramic @ 260° C.-175° C. 60 min ramp cure + 4 hour PMC) | 11.1 | 31.5 |

*The die-shear adhesion was measured as kg force on a Dage Series 4000.

The phenyl acetate functional coupling agent had almost three times the 260° C. adhesion of its phenol functional counterpart. Even at a relatively low percentage of the entire composition, the acyloxy compound is a superior epoxy curative compared to the free phenol.

Example 4

Preparation of Acrylic Acid 2-(4-Hydroxy-Phenyl)-Ethyl Ester Curative for Hybrid Epoxy and Free-Radical Cure Adhesives

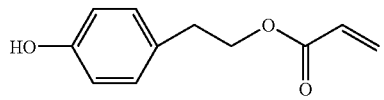

The compound shown above was designed for use as a possible hybrid monomer for adhesive compositions comprising epoxies and free-radical cure monomers. A 500 mL, two-neck flask was charged with 27.63 g (0.2 mole) 2-(4-hydroxyphenyl)ethyl alcohol, 150 mL toluene, 18.02 g (0.25 mole) acrylic acid, 40 mg hydroquinone, and 1.5 g methanesulfonic acid. The flask was equipped with a trap and condenser. The mixture was then refluxed under a mild air sparge for 1.5 hours. A total of 3.7 mL water (theoretical yield=3.6 mL) was collected in the trap. The mixture was then cooled and treated with 12 g sodium bicarbonate plus 3 g water until carbon dioxide evolution ceased. The mix was dried with 8 g magnesium sulfate and then passed over 15 g silica gel. The toluene was removed to yield 38.33 g (99.7% of theoretical yield) of a yellow liquid. The compound had prominent absorptions at 3394, 1699, 1635, 1614, 1514, 1408, 1264, 1196, 1059, 981, and 811 wavenumbers.

Example 5

Preparation of Acrylic Acid 2-(4-Acetoxy-Phenyl)-Ethyl Ester Curative for Hybrid Epoxy and Free-Radical Cure Adhesives

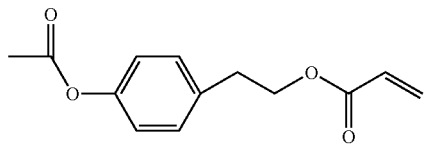 [SMILES: C=CC(=O)OCCc1ccc(OC(C)=O)cc1]

The phenyl acetate cousin of the compound described in EXAMPLE 4 was prepared according to an identical procedure except that 20.42 g (0.2 mole) acetic anhydride was added after the initial acrylate esterification was complete. This mixture was stirred overnight at 60° C. Work-up afforded 46.44 g (99.1% of theoretical yield) of a light yellow, low viscosity liquid. The compound had prominent absorptions at 1755, 1724, 1635, 1509, 1497, 1369, 1181, 1058, 984, 909, and 809 wavenumbers.

Example 6

Comparison of Epoxy Formulations Containing Hydroxy and Acetoxy Curatives

Two weight percent dicumyl peroxide was added to each of the compounds from Examples 4 and 5. These mixtures were evaluated by DSC and TGA. The results of these tests are shown in the following table:

TABLE 2

Properties of Epoxy Formulations Containing Acrylic Acid 2-(4-Hydroxy-Phenyl)-Ethyl Ester Curative or Corresponding Phenyl Acetate

| Example (w/2% Dicup) | Retained Weight @ 300° C. | Cure Energy (J/g) |
| --- | --- | --- |
| 4 | 40.1% | 6.6 |
| 5 | 89.7% | 223.8 |

The results in Table 2 indicate that the cure of the acrylate function for the EXAMPLE 4 compound was practically non-existent. This was also evident from the high weight loss for this example. The phenyl ester compound from EXAMPLE 5, by contrast, had a strong exotherm and almost 90% retained weight at 300° C. Capping the phenol with an ester function thus overcomes the inherent free-radical cure inhibition demonstrated by the free-phenol original compound.

Example 7

Preparation of a Mixed Acetate Propionate of Bisphenol A

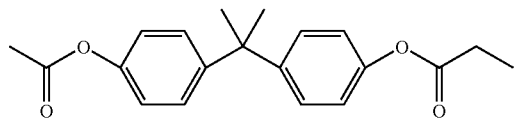 [SMILES: CCC(=O)Oc1ccc(C(C)(C)c2ccc(OC(C)=O)cc2)cc1]

A 250 mL flask was charged with 45.66 g (0.2 mole) bisphenol A, 20.42 g (0.1 mole) acetic anhydride, 26.04 g (0.1 mole) propionic anhydride, and 0.1 g DMAP catalyst). This mixture was stirred in a bath maintained at 90° C. for 1.5 hours. The residual acetic and propionic acids were then stripped off to yield a colorless liquid that weighed 64.5 g (99% of theoretical yield). It should be noted that the above representation of the example compound constitutes about 50% of the total product distribution, while the remainder is approximately a one to one mix of the diacetate and dipropionate. An advantage of this mixed product is that it has a lower melting point than any of the individual components. The mixed compound can remain as a stable supercooled liquid at room temperature for several days. It eventually crystallizes to a low melting solid. The bisacyloxy compound as a supercooled liquid had a 25° C., viscosity of 1,873 centipoise. An FTIR on this liquid showed prominent absorptions at 2971, 1756, 1504, 1367, 1166, 1015, 909, and 846 wavenumbers.

Example 8

Epoxy Generated from Mixed Acetate Propionate of Bisphenol A

A one to one equivalent mix of the diglycidyl ether of Bisphenol A (DER 332) and the bisacyloxy compound from EXAMPLE 7 was prepared. This mixture was catalyzed with two weight percent of DMAP (N,N-dimethylaminopyridine). The cure of this mixture was analyzed via DSC and TGA. The cure (via DSC) was found to give a single symmetrical peak with an onset of 123° C., a peak maximum of 143° C. and a cure energy of 182 joules per gram. The mix had 98.82% retained weight at 300° C. and a decomposition onset (TGA, 10° C./min., air purge) of 420° C. These results indicated that the DMAP catalyzed cure of the bisacyloxy compound from EXAMPLE 7 was a very synergistic co-cure, where both the acyloxy and epoxy functions fully participated.

Example 9

Preparation of Diacetate of 2,2'-Diallylbisphenol A

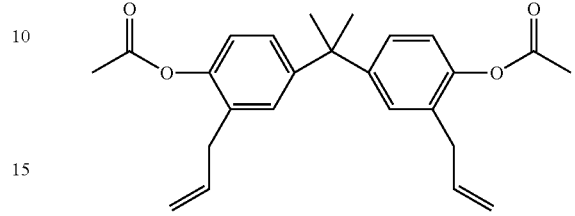

A 250 mL, single-neck flask was charged with 30.84 g (0.1 mole) o,o'-diallylbisphenol A, 20.42 g (0.2 mole) acetic anhydride, and 0.5 g DMAP. This mixture was stirred at 85° C. for one hour and the residual acetic acid was then removed to give 39.3 g (100% of theoretical yield) of a light orange liquid. The compound had prominent absorptions at 1759, 1495, 1367, 1197, 1117, 1008, 911, and 828 wavenumbers. The viscosity of this liquid was 2600 centipoise at 25° C. The viscosity of the o,o'-diallylbisphenol A starting material, by contrast, was 15,400 centipoise at the same temperature.

Example 10

Comparison of Acyloxy Curative with Corresponding Phenolic Curative

The following table shows the benefits of the acyloxy curative over a phenolic curative. The synthesis of the diacetate of o,o'-diallyl bisphenol A phenol was described in Example 9. Compositions containing the o,o'-diallyl bisphenol A phenol starting material and the corresponding diacetate were use to compare the properties of both materials when cured with bisphenol A epoxy (DER 332 from Dow Chemical). Both materials were formulated as a 1:1 epoxy equivalent and two different catalysts were used for comparison. Anjicure PN-23 is a latent aliphatic amine catalyst and DMAP (N,N-dimethyaminopyridine) is a tertiary amine catalyst. Each catalyst was used at the level of 2% of the total resin.

The data shown in Table 3 below demonstrate the superior properties for the phenyl acetate curative in the terms of moisture absorption, adhesion, weight loss, cure energy, and viscosity. The ortho diallyl bis A phenol either had unacceptable worklife with the DMAP and cured to a thermoplastic under these conditions making it difficult to collect the TMA data.

TABLE 3

Properties of Epoxy Formulations Containing of Acyloxy Curative and Corresponding Phenolic Curative
Phenol Acetate Experiments

|  | 115-51A | 115-51B | 115-51C | 115-51D |
| --- | --- | --- | --- | --- |
| 1:1 equivalents |  |  |  |  |
| DER 332% | 48 | 48 | 54 | 54 |
| ortho diallyl Bis A phenol % | 52 | 52 |  |  |
| ortho diallyl Bis A phenylacetate % |  |  | 46 | 46 |
| Ajicure PN-23 (2% level) | X |  | X |  |
| DMAP (2% level) |  | X |  | X |

TABLE 3-continued

Properties of Epoxy Formulations Containing of
Acyloxy Curative and Corresponding Phenolic Curative
Phenol Acetate Experiments

|  | 115-51A | 115-51B | 115-51C | 115-51D |
|---|---|---|---|---|
| Dynamic TGA (10° C./min) | | | | |
| Weight loss at 300° C. % | 1.1 | 2.1 | 0.5 | 1.2 |
| Onset for decompostion ° C. | 398 | 402 | 391 | 395 |
| DSC (10° C./min) | | | | |
| onset for cure ° C. | 85 | 50 | 75 | 75 |
| Peak cure temperature ° C. | 154 | 124 | 150 | 135 |
| Peak energy J/g | 155 | 107 | 187 | 178 |
| TMA | | | | |
| Alpha 1 | NA* | NA | 62 | 48 |
| Tg | NA | NA | 57 | 53 |
| Alpha 2 | NA | NA | 324 | 315 |
| RT modulus (70% Ag) | 4.5 GPa | NA | 6.5 GPa | 5.8 GPa |
| Viscosity 5 rpm (70% Ag) | 64 Kcps | cured within hours | 18 Kcps | 18 Kcps |
| 260° C. die shear $150^2$ mil dieBare Cu | <1 kgf | | 2.7 kgf | 3.0 kgf |
| Moisture Absorption 96 hours in 85/85% | 1.28 | | 0.78 | 0.60 |

*Comments Thermoplastic, TMA NA

Example 11

Preparation of the Bis-4-Acetoxybenzoate of Dimer Diol

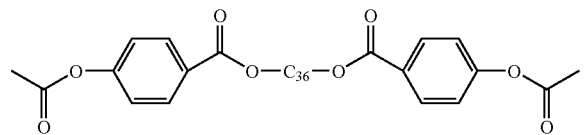

A one liter, single neck flask was charged with 55.25 g (0.4 mole) 4-hydroxybenzoic acid, 107.4 g (0.2 mole) dimer diol, 250 mL toluene, and 20 g of dry Amberlyst 46 resin. A magnetic stir bar was placed in the flask and a trap, condenser, and bubbler were attached. The mix was refluxed under an argon blanket for twenty-eight hours and 7.9 mL water (theoretical yield=7.2 mL) was collected. The Amberlyst catalyst was filtered out using a fritted funnel and the toluene was then removed. The product was then reacted with 40.84 g (0.4 mole) acetic anhydride plus 0.2 g DMAP at 90° C. for 1.5 hours. The acetic acid side product was then removed to yield 168.7 g (98% of theoretical yield) of a light yellow liquid. This compound had prominent infrared absorptions at 2922, 2853, 1763, 1720, 1271, 1190, 1158, 1115, 1016, and 912 wavenumbers.

Example 12

Epoxy Mixtures with Bis-4-Acetoxybenzoate of Dimer Diol

Mixtures were made using the DER 332 epoxy, a combination of two catalysts, and various levels of the curative from EXAMPLE 11. The mixture compositions are shown in Table 4 and the cured properties of those compositions are shown in Table 5.

TABLE 4

Epoxy + EXAMPLE 11 Curative Compositions

| Mixture | DER 332% | Exp. 11% | Anjicure PN23 % | Zn Undecylate % |
|---|---|---|---|---|
| A | 85 | 5 | 5 | 5 |
| B | 80 | 10 | 5 | 5 |
| C | 75 | 15 | 5 | 5 |
| D | 70 | 20 | 5 | 5 |

TABLE 5

Thermoset Cured Properties From Table 4 Mixtures

| Mixture | Alpha 1 (ppm/° C.) | Alpha 2 (ppm/° C.) | $T_g$ (° C.) | Moisture Uptake[a] |
|---|---|---|---|---|
| A | 63.2 | 210 | 106.5 | 1.55 |
| B | 66.4 | 212 | 105.9 | 1.02 |
| C | 69.5 | 221 | 90.3 | 0.87 |
| D | 76.5 | 231 | 72.5 | 0.74 |

[a] Percent weight gain at 85° C./85 RH over 168 hours

It is apparent from the results given in Table 5 that small additions of the curative from EXAMPLE 11 can dramatically reduce the moisture uptake, without significantly reducing the glass transition temperature or increasing the thermal expansion coefficient. Higher addition levels of this curative further reduced moisture uptake, but the thermoset cured property parameters were more severely impacted.

Example 13

Preparation of 2,7-dimethacryloxynapthalene

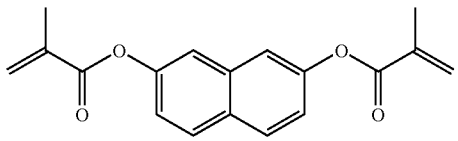 [SMILES: C=C(C)C(=O)Oc1ccc2ccc(OC(=O)C(=C)C)cc2c1]

A 500 mL, single-neck flask was charged with 16.02 g (0.1 mole) 2,7-dihydroxynaphthalene, 150 mL toluene, 30.8 g (0.2 mole) methacrylic anhydride, 30 mg of BHT, and 0.5 g DMAP. This mixture was stirred on an oil bath set at 65° C. for 72 hours. The residual methacrylic acid was neutralized with 30 g sodium bicarbonate plus 5 g water, and then dried over 12 g anhydrous magnesium sulfate. The mixture was passed over 12 g of silica gel and the toluene was removed to yield 25.1 g (84.7% of theoretical yield) of what at first appeared to be a light red colored liquid. The compound converted to a waxy solid upon standing at room temperature. The product had significant infrared absorptions at 1730, 1637, 1316, 1202, 1114, 943, and 806 wavenumbers.

A portion of this compound was catalyzed with two weight percent of dicumyl peroxide. This mixture was found to have a cure onset of 137.4° C., and a cure maxima of 148.5° C. by DSC. The mix was found to have 93.9% retained weight at 300 C, and a decomposition onset of 423° C. (10° C./minute, air purge) via TGA. A cured sample of this compound was found to have a remarkably low alpha 1 value of 41.4 ppm/° C., an alpha 2 of 117 ppm/° C. and a $T_g$ of 78.1° C. by TMA. This compound is a useful acyloxy curative. It can be used as a chain extender for di-functional epoxies. The extended, thermoplastic oligomer can be cross-linked through the pendant methacrylate moieties in a secondary free radical cure.

Example 14

Preparation of Acyloxy-Phenylmaleimide Mixture

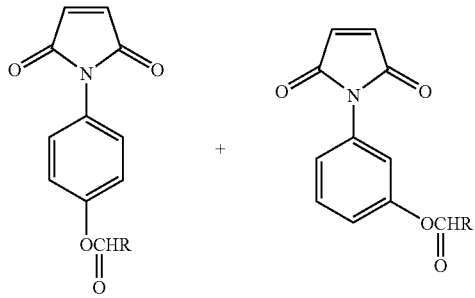

wherein R is $CH_3$ or $CH_2CH_3$

A 125 mL flask was charged with 1.89 g (0.01 mole) of 4-hydroxyphenylmaleimide, 1.89 g (0.01 mole) of 3-hydroxyphenylmaleimide and half an equivalent each of acetic anhydride and propionic anhydride along with about 10 mg of DMAP catalyst. The flask was stirred on a rotovap for two hours at 90° C. and then the residual acetic and propionic acids were removed by sparging. The resulting red liquid set up to an orange solid at room temperature. The product had strong infrared absorptions at 1756, 1717, 1510, 1398, 1196, 1148, 828, and 689 wavenumbers. The mixed compound was found to have a broad melting point via DSC. The melt onset was 93.8° C., with a melt minima at 107.9° C. The acyloxyphenylmaleimide mixture appeared to be readily soluble in other monomers.

Example 15

Preparation of a Mixed N-Acylimide Curative

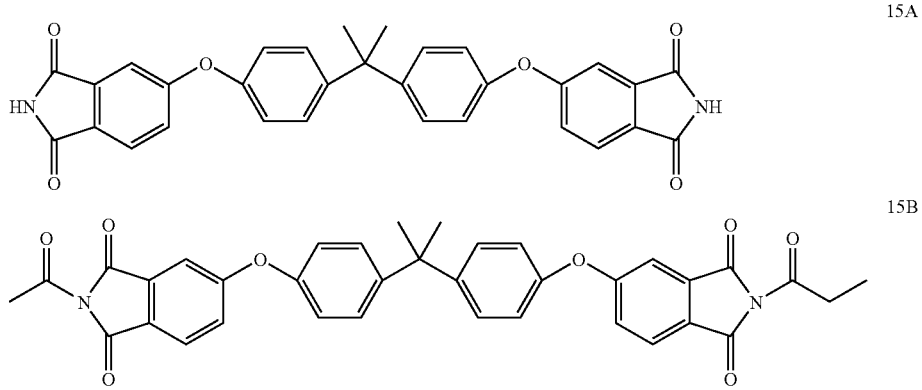

The imide precursor 15A was prepared from the commercially available Ultem BPADA (GE Plastics, Pittsfield, Mass.). Thus, 52.0 g (0.1 mole) of the dianhydride and 6.0 g (0.1 mole) urea were ground together in a mortar and pestle. This mixture was transferred to a single neck, 500 mL flask. The flask was equipped with a condenser and bubbler, and then heated in an oil bath that was controlled at 133° C. The mix foamed up as carbon dioxide and then water were evolved. The contents were occasionally stirred to insure homogeneity. The temperature bath was raised to and held at 165° C. for thirty minutes once $CO_2$ generation had ceased. The mix was cooled to room temperature and then 60 mL of deionized water was added. The slurry was transferred to a Buchner funnel and the solids were rinsed with deionized water. The solid was dried at 100° C. in an oven to yield 49.9 g (96.2% of theoretical yield) of a cream colored powder. An FTIR was run on this compound and it was found to have significant absorptions at 3264, 1766, 1716, 1598, 1476, 1361, 1237, 1041, 835, and 749 wavenumbers.

The mixed N-acyl curative 15B was prepared by charging a 250 mL, one-neck flask with 25.93 g (0.05 mole) compound 15A, 5.3 g (0.052 mole) acetic anhydride, 6.76 g (0.052 mole) propionic anhydride, 0.2 g DMAP catalyst, and 100 mL toluene. A magnetic stir bar was added and a condenser attached to the flask. This mixture was gently refluxed for twenty hours (during which time all of the solids went into solution). A light yellow solid precipitated out when the solution was cooled to room temperature. This solid was transferred to a Buchner funnel and rinsed with toluene. The solid was dried to yield 30.96 g (100% of theoretical yield) of a yellow-white powder. This compound was found to have a melting point of 197-200° C. An FTIR on the compound revealed significant absorptions at 2921, 1795, 1753, 1714, 1598, 1471, 1360, 1280, 1230, 1170, 1079, 840, and 745 wavenumbers.

Example 16

Preparation of an N-Acetylimide Curative Oligomer

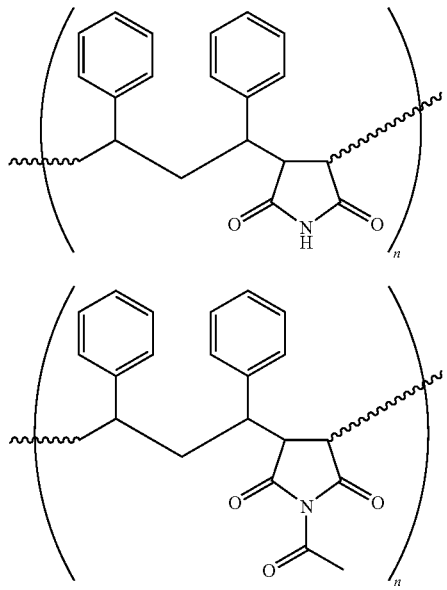

The imide precursor 16A was prepared from the commercially available poly(styrene-co-maleic anhydride) compound SMA-2000P (Sartomer Company, Inc. Exton Pa., USA). Thus, 30.8 g (0.1 equivalent) of the polyanhydride and 6.0 g (0.1 mole) urea were ground together in a mortar and pestle. This mixture was transferred to a single neck, 500 mL flask and 15 mL of NMP was added. The flask was equipped with a condenser and bubbler, and then heated in an oil bath that was controlled at 135° C. The mix foamed up as carbon dioxide and then water were evolved. The contents were occasionally stirred to insure homogeneity. The temperature bath was raised to and held at 165° C. for three hours once $CO_2$ generation had ceased. The mix was cooled to room temperature and then dissolved in 60 mL of acetone. The solution was dripped into 500 mL of vigorously stirred deionized water. The solid was collected and dried at 80° C. in an oven to yield 29.86 g (97.1% of theoretical yield) of a cream colored powder. An FTIR was run on this compound and it was found to have significant absorptions at 3207, 1771, 1711, 1453, 1381, 1181, 760, and 701 wavenumbers.

The N-acetyl curative oligomer 16B was prepared by slowly dripping 6.3 g (0.08 mole) acetyl chloride into a magnetically stirred solution containing 23.1 g (0.075 equivalents) 16A, 9.1 g (0.09 mole) triethylamine and 50 mL acetone. There was an immediate exotherm and a solid precipitate of triethylamine hydrochloride was observed to form. This mixture was stirred for another forty-five minutes and was then dripped into a one-liter beaker containing 500 mL of vigorously stirred deionized water. The solid was collected and then re-dissolved in 75 mL fresh acetone and the product was once again precipitated into 500 mL of deionized water.

The solid was recovered via filtration and dried in an oven at 75° C. The product was an off-white fine powdered solid that weighed 24.57 g (93.7% of theoretical yield). An FTIR on the compound revealed significant absorptions at 3028, 2925, 1801, 1751, 1708, 1601, 1494, 1453, 1384, 1295, 1195, 759, and 704 wavenumbers.

Example 17

Epoxy Blends with the N-Acetylimide Curative Oligomer

A mixture was made that contained 70% by weight compound 16B, 30% limonene dioxide and one part per hundred of DMAP catalyst. A DSC was run on this composition and an exotherm was observed to occur with an onset of 153° C., a cure maximum of 170.7° C. and with a cure energy of 68 J/g.

Another mix was made consisting of 75% by weight compound 16B, 25% ERL-4221 (Dow Chemical) and one part per hundred DMAP catalyst. A DSC was run on this composition and an exotherm was observed with an onset of 121.6° C., a maximum at 169.2° C. and a cure energy of 48.2 J/g.

The limonene dioxide is a mixed cycloaliphatic and aliphatic epoxy compound while the ERL-4221 is a bi-functional cycloaliphatic epoxy. The 16B was shown to be an active curative for both of these epoxy compounds.

Example 18

Cyclic Siloxane Phenyl Ester Epoxy Curative

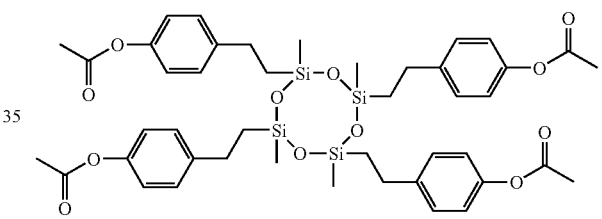

Methylhydrocyclosiloxane (30.1 g, 125 mmol) was dissolved in toluene (50 ml) in a 2-neck, 500 ml flask. Dihydrogen hexachloroplatinate (20 mg) and a stir bar were added to the flask. A temperature probe was attached to one of the necks. A condenser was attached to the other. 4-acetoxystyrene (81.1 g, 500 mmol) was diluted with toluene (100 ml) and placed into an addition funnel. The addition funnel was placed on top of the condenser. The toluene solution containing methylhydrocyclosiloxane and catalyst was stirred and controlled at 80° C. One-third of the solution in the addition funnel was dripped in. The addition did not initially show evidence of an exotherm. The pot temperature was increased to 90° C. and the remaining solution in the addition funnel was allowed to drip in. An exotherm occurred during this addition that caused the temperature to increase the temperature to over a 100° C. The temperature was reset to 100° C. and the solution was left to stir at this temperature overnight. When the reaction was complete, the flask was equipped with a trap and sparge tube.

The solution was air sparged at 100° C. for 6 hours to remove the toluene. A total of 95.7 g (86.1% theory) of a very viscous, light yellow, clear liquid was recovered. The compound was subjected to thermogravimetric analysis (TGA). The retained weight at 300° C. (TGA ramp rate=10° C./min., air purge) was 95.43%. Infrared spectrum included absorptions at 2961, 1759, 1504, 1369, 1260, 1193, 1059, 909, and 782 wavenumbers. The 40° C. viscosity of this compound was found to be 23,863 cps at 5 RPM.

Example 19

Hybrid Epoxy-Phenyl Ester Thermoset Monomer

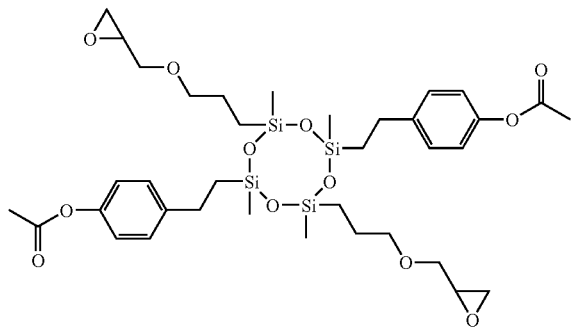 [SMILES: CC(=O)Oc1ccc(CC[Si]2(C)O[Si](C)(CCCOCC3CO3)O[Si](C)(CCc3ccc(OC(C)=O)cc3)O[Si](C)(CCCOCC3CO3)O2)cc1]

Methylhydrocyclosiloxane (30.1 g, 125 mmol) was dissolved with toluene (50 ml) in a 2-neck, 500 ml flask. Dihydrogen hexachloroplatinate (20 mg) and a stir bar were added to the flask. A temperature probe was attached to one of the necks. A condenser was attached to the other neck. 4-Acetoxystyrene (40.6 g, 250 mmol) and allyl glycidyl ether were diluted with toluene (100 ml) and transferred to an addition funnel. The addition funnel was placed on top of the condenser. The initial pot temperature was set to 80° C. The solution in the addition funnel was then added dropwise. The addition caused the temperature to increase the temperature to a 100° C. The addition was paused until the temperature cooled down to 80° C. The addition was continued, but no additional exotherm was observed. Once all of the contents of the addition funnel had been added, the temperature was increased to 90° C. and then to 100° C. The temperature was maintained at 100° C. for 30 minutes. The temperature was then increased to 110° C. for 2 hours. FTIR on the solution showed the complete disappearance of the Si—H peak.

The solution was air sparged at 95° C. for 5 hours to remove the toluene. 73.6 g (74.3% theory) of a viscous, tan colored liquid was recovered. The compound was subjected to thermogravimetric analysis (TGA). The retained weight at 300° C. (TGA ramp rate=10° C./min., air purge) was 96.4%. Infrared spectrum included absorptions at 2932, 1764, 1505, 1369, 1259, 1192, 1050, 908, and 793 wavenumbers.

Example 20

Hybrid Allyl-Phenyl Ester Epoxy Curative

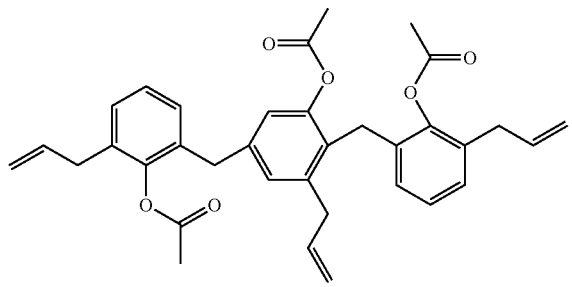 [SMILES: C=CCc1cc(Cc2cccc(CC=C)c2OC(C)=O)cc(OC(C)=O)c1Cc1cccc(CC=C)c1OC(C)=O]

2-Allyphenyl novolac (42.7 g, 300 meq, "Rezicure 3700" available from SI Group), acetic anhydride (30.6 g, 300 mmol), and 4-dimethylaminopyridine (0.2 g) were added to a 250 ml flask. The mixture was stirred at 80° C. for 2 hours. The acid was removed via air sparge for 6 hours at 85° C. The product was recovered as a dark red liquid with a yield of 54.5 g (98.5% theory). The compound was subjected to thermogravimetric analysis (TGA). The retained weight at 200° C. (TGA ramp rate=10° C./min., air purge) was 99.6% and the decomposition onset was at 267° C. Infrared spectrum included absorptions at 1758, 1639, 1495, 1433, 1368, 1192, 1120, 1009, 909, 827, and 768 wavenumbers. The 25° C. viscosity for this product was found to be 2538 cps at 5 RPM.

Example 21

2,4-Diacyloxybenzophenone Phenyl Ester Epoxy Curative

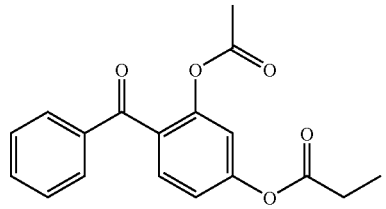 [SMILES: CCC(=O)Oc1ccc(C(=O)c2ccccc2)c(OC(C)=O)c1]

2,4-Dihydroxybenzophenone (43.9 g, 205 mmol), acetic anhydride (20.9 g, 205 mmol), propionic anhydride (26.7 g, 205 mmol), and 4-dimethylaminopyridine (0.2 g) were added to a 250 ml flask. The flask was immersed into a heated bath and rotated at 80° C. for 5 hours. An FTIR on the mixture indicated that the anhydrides had reacted completely. The residual acids were removed via air sparge at 80° C. The product was a moderately viscous liquid that weighed 63.3 g (98.9% theory). The compound was subjected to thermogravimetric analysis (TGA). The retained weight at 200° C. (TGA ramp rate=10° C./min., air purge) was 96.8% and the decomposition onset was at 232° C. Infrared spectrum included absorptions at 1763, 1662, 1605, 1448, 1368, 1255, 1188, 1120, 1010, 898, 799, and 701 wavenumbers. The 25° C. viscosity for this compound was 5540 cps at 10 RPM.

Example 22

Sulfide Bridged Phenyl Ester Epoxy Curative

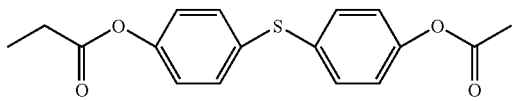 [SMILES: CCC(=O)Oc1ccc(Sc2ccc(OC(C)=O)cc2)cc1]

Bis(4-hydroxyphenyl)sulfide (21.8 g, 100 mmol), acetic anhydride (10.2 g, 100 mmol), propionic anhydride (13.0 g, 100 mmol), and 4-dimethylaminopyridine (50 mg) were added to a 250 ml flask. The mixture was rotated on a rotovap at 85° C. for 4.5 hours. FTIR indicated that the anhydrides had reacted completely. The residual acids were removed via air sparge at 85° C. The product was an almost colorless liquid that solidified on standing. It weighed 31.5 g (99.6% theory). The compound was subjected to thermogravimetric analysis (TGA). The retained weight at 200° C. (TGA ramp rate=10° C./min., air purge) was 99.3% and the decomposition onset was at 266° C. A DSC was conducted (ramp rate=10° C./min., air purge) on a sample of this material. The melting point onset was 37.7° C. and the peak was 42.3° C. Infrared spectrum included absorptions at 2982, 1757, 1588, 1485, 1368, 1192, 1075, 1011, 899, 840, 797, and 717 wavenumbers.

Example 23

Siloxane Extended Phenyl Ester Epoxy Curative

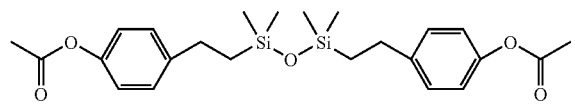 [SMILES: CC(=O)Oc1ccc(CC[Si](C)(C)O[Si](C)(C)CCc2ccc(OC(C)=O)cc2)cc1]

Tetramethyldisiloxane (134.4 g, 1.00 mol) was dissolved in toluene (100 ml) in a 2-neck, 2 L flask. 5% Platinum on carbon (100 mg) and a stir bar were added to the solution. A temperature controller probe was attached to one of the necks. A condenser attached to the other. 4-Acetoxystyrene (324.4 g, 2.00 mol) and toluene (200 ml) were added to an addition funnel. The addition funnel was attached to the top of the condenser. A bubbler was attached to the top of the addition funnel. A chiller for the condenser cooling fluid was turned on and controlled at 10-15° C. The solution in the pot was heated to 95° C. The solution in the addition funnel was dripped in. The combined solution was then stirred at 95° C. for sixty hours. An FTIR on the solution following this period showed the complete absence of the Si—H peak. The solution was passed over silica gel (50 g).

The toluene was removed via rotary evaporation followed by an air sparge in a 130° C. oil bath. The product was free of solvent after 3.0 hours of sparging. The product was a fairly low viscosity, almost colorless liquid that weighed 446.5 g (97.3% theory). The compound was subjected to thermogravimetric analysis (TGA). The retained weight at 200° C. (TGA ramp rate=10° C./min., air purge) was 99.1% and the decomposition onset was at 260° C. Infrared spectrum included absorptions at 2953, 1762, 1505, 1368, 1252, 1196, 1048, 907, 834, 782, and 701 wavenumbers. The 25° C. viscosity was 97 cps at 10 RPM.

Example 24

Siloxane Extended Diphenol Epoxy Curative

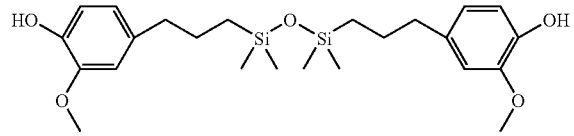 [SMILES: COc1cc(CCC[Si](C)(C)O[Si](C)(C)CCCc2ccc(O)c(OC)c2)ccc1O]

Tetramethyldisiloxane (33.6 g, 250 mmol) was dissolved in toluene (50 ml) in a 2-neck, 500 ml flask. 5% Platinum on carbon (50 mg) and a stir bar were added to the solution. A temperature controller probe was attached to one of the necks. A condenser attached to the other. Eugenol (82.1 g, 500 mmol) and toluene (100 ml) were added to an addition funnel. The addition funnel was attached to the top of the condenser. A bubbler was attached to the top of the addition funnel. A chiller for the condenser cooling fluid was turned on and controlled at 10-15° C. The solution in the pot was heated to 95° C. The solution in the addition funnel was dripped in. The combined solution was then stirred at 95° C. overnight. An FTIR on the solution the next morning showed the complete disappearance of the Si—H peak. The solution was passed over silica gel (15 g). The toluene was removed via rotary evaporation followed by an air sparge in a 130° C. oil bath. The product was free of solvent after 2.5 hours of sparging.

The product was a moderately viscous, yellow liquid that weighed 111.7 g (96.6% theory). The compound was subjected to thermogravimetric analysis (TGA). The retained weight at 200° C. (TGA ramp rate=10° C./min., air purge) was 98.0% and the decomposition onset was at 280° C. Infrared spectrum included absorptions at 3545, 2925, 1606, 1513, 1429, 1367, 1250, 1206, 1150, 1034, 839, 792, and 703 wavenumbers. The 25° C. viscosity was 437 cps at 10 RPM.

Example 25

Siloxane Extended Phenyl Ester Epoxy Curative

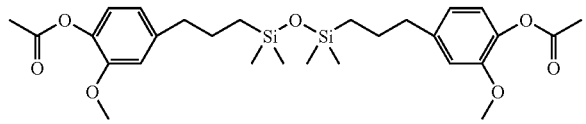 [SMILES: COc1cc(CCC[Si](C)(C)O[Si](C)(C)CCCc2ccc(OC(C)=O)c(OC)c2)ccc1OC(C)=O]

The product (SD23-22B) obtained from the previous reaction (46.3 g, 100 mmol), acetic anhydride (20.4 g, 200 mmol), and 4-dimethylaminopyridine (50 mg) were charged into a 1-neck, 500 ml flask. The mixture was rotated in an 80° C. water bath for 10 hours. The residual acetic acid was removed via air sparge at 80° C. for 2 hours. The product was a moderately viscous, light amber liquid. The compound was subjected to thermogravimetric analysis (TGA). The retained weight at 200° C. (TGA ramp rate=10° C./min., air purge) was 99.3% and the decomposition onset was at 292° C. Infrared spectrum included absorptions at 2928, 1762, 1604, 1510, 1455, 1368, 1252, 1186, 1149, 1125, 1031, 903, 836, and 789 wavenumbers. The 25° C. viscosity was 1667 cps at 10 RPM.

Example 26

1,2,3-Triacyloxy Phenyl Ester Epoxy Curative

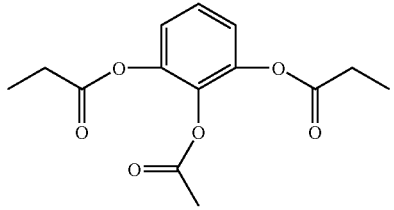 [SMILES: CCC(=O)Oc1cccc(OC(=O)CC)c1OC(C)=O]

1,2,3-Trihydroxybenzene (25.2 g, 200 mmol), acetic anhydride (20.4 g, 200 mmol), propionic anhydride (52.0 g, 400 mmol), and 4-dimethylaminopyridine (200 mg) were added to a 500 ml flask. The mixture was rotated on a rotovap at 80° C. for 4 hours. FTIR indicated that the anhydrides had reacted completely. The residual acids were removed via rotary evaporation followed by air sparge at 80° C. The product was a tan colored solid that weighed 54.9 g (98% theory). The compound was subjected to thermogravimetric analysis (TGA). The retained weight at 100° C. (TGA ramp rate=10° C./min., air purge) was 99.3% and the decomposition onset was at 197° C. A DSC was conducted (ramp rate=10° C./min., air purge) on a sample of this material. The product had a broad melt between 52 and 80° C. Infrared spectrum included absorptions at 2986, 2885, 1761, 1605, 1472, 1370, 1270, 1122, 1033, and 874 wavenumbers.

Example 27

1,3,5-Triacyloxy Phenyl Ester Epoxy Curative

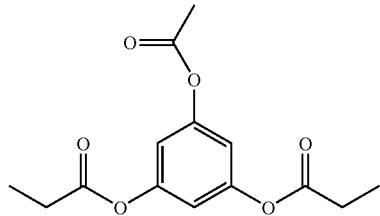 [SMILES: CCC(=O)Oc1cc(OC(C)=O)cc(OC(=O)CC)c1]

1,3,5-Trihydroxybenzene (25.2 g, 200 mmol), acetic anhydride (20.4 g, 200 mmol), propionic anhydride (52.0 g, 400 mmol), and 4-dimethylaminopyridine (200 mg) were added to a 2-neck, 500 ml flask. A stir bar was added to the flask. A temperature probe was attached to one neck. A condenser was attached to the other. The temperature was set to 80° C. An initial exotherm caused the temperature to overshoot to 131° C. The reaction was complete after 8.25 hours. The residual acids were removed by air sparge at 85-90° C. 55.6 g (99.2%) of a fairly low viscosity, amber liquid was recovered. The compound was subjected to thermogravimetric analysis (TGA). The retained weight at 200° C. (TGA ramp rate=10° C./min., air purge) was 94.5%. Infrared spectrum included absorptions at 2982, 1758, 1605, 1454, 1353, 1188, 1113, 1077, 1018, 900, 805, and 665 wavenumbers.

Example 28

2,3,4-Triacyloxybenzophenone Phenyl Ester Epoxy Curative

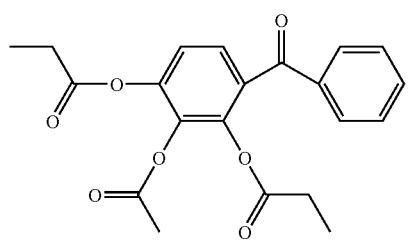 [SMILES: CCC(=O)Oc1ccc(C(=O)c2ccccc2)c(OC(=O)CC)c1OC(C)=O]

2,3,4-Trihydroxybenzophenone (23.0 g, 100 mmol), acetic anhydride (10.2 g, 100 mmol), propionic anhydride (26.0 g, 200 mmol), and 4-dimethylaminopyridine (200 mg) were added to a 500 ml flask. The mixture was rotated in a water bath at 80-90° C. for 2.25 hours. FTIR indicated that the anhydrides had reacted completely. The residual acids were removed by sparging with clean dry air at 95° C. The product was a very, viscous, tacky, dark amber liquid that weighted 35.2 g (91.6% theory). The compound was subjected to thermogravimetric analysis (TGA). The retained weight at 200° C. (TGA ramp rate=10° C./min., air purge) was 98.5% and the decomposition onset was at 272° C. Infrared spectrum included absorptions at 2987, 1789, 1667, 1598, 1447, 1261, 1161, 1118, 1050, 864, 800, and 702 wavenumbers.

Example 29

2,2',4,4'-Tetraacyloxybenzophenone Phenyl Ester Epoxy Curative

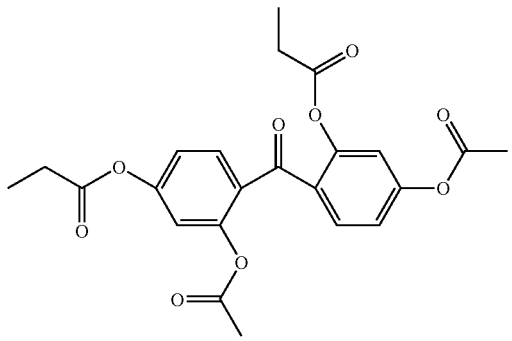 [SMILES: CCC(=O)Oc1ccc(C(=O)c2ccc(OC(C)=O)cc2OC(=O)CC)c(OC(C)=O)c1]

2,2',4,4'-Tetrahydroxybenzophenone (24.6 g, 100 mmol), acetic anhydride (20.4 g, 200 mmol), propionic anhydride (26.0 g, 200 mmol), and 4-dimethylaminopyridine (200 mg) were added to a 250 ml flask. The mixture rotated in a water bath at 80-90° C. for 5.25 hours. FTIR indicated that the anhydrides had reacted completely. The residual acids were removed by sparging with clean dry air at 80° C. for 9 hours. The product did not seem to be free of acid after the 80° C. sparge, so it was sparged in a 120° C. oil bath for 8 hours. The final product was an amber, viscous almost gel-like liquid that weighted 42.0 g (97.9% theory). The compound was subjected to thermogravimetric analysis (TGA). The retained weight at 200° C. (TGA ramp rate=10° C./min., air purge) was 98.1% and the decomposition onset was at 251.6° C. Infrared spectrum included absorptions at 2987, 1766, 1668, 1604, 1493, 1417, 1370, 1253, 1198, 1143, 1013, 906, and 832 wavenumbers.

Example 30

Sulfone Bridged Phenyl Ester Epoxy Curative

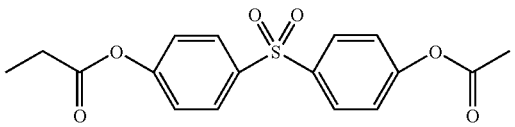

Bis(4-hydroxyphenyl)sulfone (225.2 g, 900 mmol), acetic anhydride (91.9 g, 900 mmol), propionic anhydride (117.1 g, 900 mmol), and 4-dimethylaminopyridine (450 mg) were added to a 1 L flask. The mixture rotated in a 115° C. oil bath for 7.75 hours. FTIR indicated that the reaction was complete. The residual acids were removed via rotary evaporation followed by air sparge at 115° C. The product was an off-white solid that weighed 308.9 g (98.5% theory). The compound was subjected to thermogravimetric analysis (TGA). The retained weight at 200° C. (TGA ramp rate=10° C./min., air purge) was 99.6% and the decomposition onset was at 320° C. A DSC was conducted (ramp rate=10° C./min., air purge) on a sample of this material. The onset of the melting point was 99.5° C. and the peak was 100.8° C. Infrared spectrum included absorptions at 1754, 1585, 1487, 1319, 1098, 1013, 847, and 736 wavenumbers.

Example 31

Novolac Polybenzoate Epoxy Curative

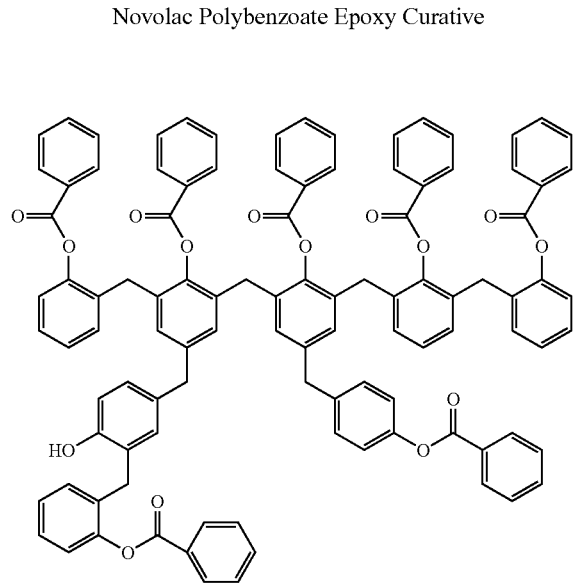

Rezicure 3000 (53.0 g, 500 meq, available from SI Group), triethylamine (53.1 g, 525 meq), toluene (100 ml), and a stir bar were added to a 2-neck, 500 ml flask. Benzoyl chloride (66.8 g, 475 meq) was added dropwise into the mixture. When completely added, the mixture was allowed to stir at room temperature overnight. The next day, the temperature was turned up to 100° C. for 1.5 hours. The mixture was transferred to a separation funnel and diluted with toluene (300 ml). Water extractions (3×100 ml) were used to remove the salt from the mixture. The organic phase was also rinsed with brine (100 ml). The mixture was dried with magnesium sulfate (25 g) then passed over silica (25 g). The toluene was removed via rotary evaporation followed by air sparge. The product was a clear, light yellow, glassy solid that weighed 83.7 g (82.6% theory). The compound was subjected to thermogravimetric analysis (TGA). The retained weight at 300° C. (TGA ramp rate=10° C./min., air purge) was 98.5% and the decomposition onset was at 366° C. The infrared spectrum included absorptions at 3481, 3059, 1735, 1600, 1505, 1265, 1058, 870, and 701 wavenumbers.

Example 32

Novolac Polyacetate Epoxy Curative

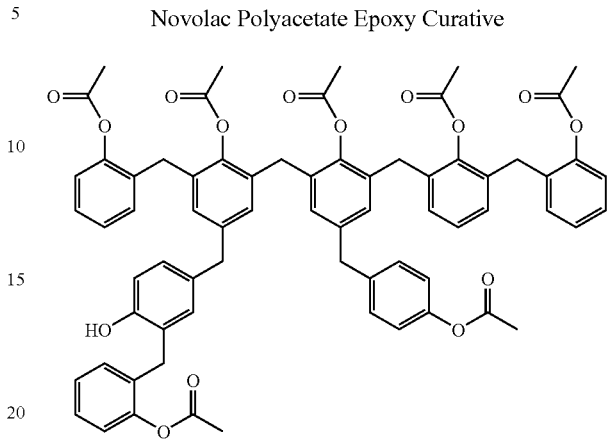

Rezicure 3000 (424 g, 4000 meq, available from SI Group), acetic anhydride (408.4 g, 4000 mmol), 4-dimethylaminopyridine (1.0 g), and a stir bar were charged into a 2 L, 1-neck flask. A Claisen head was attached. A temperature probe was added to one neck and a condenser was attached to the other. The temperature was set to 85° C., but an initial overshoot allowed the temperature to get as high as 129° C. The reaction was complete after 20.5 hours at 80° C. The stir bar was removed and the flask was place onto a rotovap. The acid was removed via air sparge in a 115° C. oil bath. 590 g of a reddish-brown, glassy solid was recovered. The compound was subjected to thermogravimetric analysis (TGA). The retained weight at 200° C. (TGA ramp rate=10° C./min., air purge) was 99.9% and the decomposition onset was at 258° C. The infrared spectrum included absorptions at 3484, 3039, 2925, 1750, 1608, 1505, 1369, 1206, 1013, 911, 830, and 752 wavenumbers.

Example 33

Comparison of Novolac and Novolac Polyacyloxy Epoxy Curatives

Test compositions were made using the curatives from Examples 31, 32, and the Rezicure 3000 novolac starting material. All test mixtures were made using one to one equivalents of each of the curatives with the diglycidyl ether of Bisphenol F. All mixtures were catalyzed with two weight percent Curezol 2P4MZ azine. These compositions were compared in terms of their performance in terms of TGA, DSC and TMA analysis. The results of that testing is summarized in Table 6.

TABLE 6

Thermoset Cure Performance and Thermoset Properties Comparison Between Two Novolac Phenyl Ester Curatives and Corresponding Novolac Starting Compound

| Curative | Onset (° C.) | Cure Max (° C.) | Δ H (J/g) | Reside @ 300° C. | Decomp. Onset (° C.) | Glass Transition (° C.) |
|---|---|---|---|---|---|---|
| Rezicure 3000 | 133 | 157 | 217 | 98.3% | 423 | 105 |
| Example 32 | 151 | 175 | 261 | 98.8% | 416 | 62 |
| Example 31 | 160 | 182 | 188 | 99.9% | 431 | 83 |

The Rezicure 3000 (free-phenol) starting material had the lowest onset, cure peak maximum, 300° C. residual weight, and glass transition temperature. Both of the acyloxy curatives were more latent. The composition containing Example 32 had 0.5% less weight loss at 300° C. than the control, while the resin mix containing the Example 31 curative had 1.6% less weight loss than the control. The Example 32 curative reduced the glass transition temperature by 43° C. versus the control, while the Example 31 curative had a $T_g$ that was 22° C. lower than the control. The exemplary curatives present advantages in terms of latency and reduced volatility. The elimination of hydroxy functionality, furthermore, makes these curatives desirable in terms of the inherent hydrophobicity.

Example 34

Bisphenol F Phenyl Ester Epoxy Curative

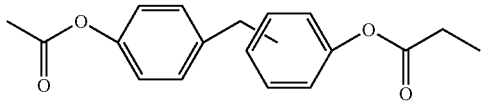

Bisphenol F (100.10 g, 500 mmol), acetic anhydride (65.05 g, 500 mmol), propionic anhydride (51.05 g, 500 mmol), and 4-dimethylaminopyridine (0.25 g) were charged into a 500 ml flask. The mixture was rotated in a water bath set at 65° C. for 5.25 hours. The temperature of the bath was then increased to 85° C. for another 2.75 hours. The residual acids were removed via vacuum followed by a sparge with clean dry air at 85° C. Toluene (200 ml) was added to the flask and the solution was filtered over a bed of silica gel (30 g). The toluene was then removed via rotary evaporation followed by an air sparge in a 55° C. water bath. The product was an odorless, clear, yellow, moderately viscous liquid that weighed 144.4 g (96.8% theory). The compound was subjected to thermogravimetric analysis (TGA). The decomposition onset (TGA ramp rate=10° C./min., air purge) was at 252° C. Infrared spectrum included prominent absorptions at 1757, 1505, 1369, 1193, 1017, 910, 806, and 752 wavenumbers. The viscosity of this liquid at 25° C. was 509 centipoise.

Example 35

2,3-Acyloxy Substituted Naphthalene Epoxy Curative

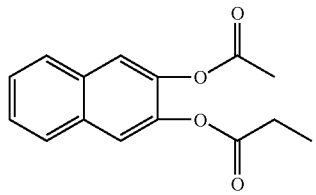 [SMILES: CCC(=O)Oc1cc2ccccc2cc1OC(C)=O]

2,3-Dihydroxynaphthalene (32.0 g, 200 mmol), acetic anhydride (20.4 g, 200 mmol), propionic anhydride (26.0 g, 200 mmol), and 4-dimethylaminopyridine (0.1 g) were added to a 250 ml flask. The flask was rotated for one hour in a heated bath that was controlled at approximately 85° C. An FTIR run on this mixture showed the complete disappearance of the anhydride carbonyl absorption, indicating the reaction was finished. The acids were removed under vacuum in a rotary evaporator followed by a sparge at 85° C. with clean, dry air. The reaction product recovered weighed 50.9 g (98.5% theory). It was a reddish brown, moderately viscous liquid. The compound was subjected to thermogravimetric analysis (TGA). The decomposition onset (TGA ramp rate=10° C./min., air purge) was at 233° C. Infrared spectrum included absorptions at 1766, 1603, 1508, 1468, 1363, 1248, 1189, 1095, 1009, 900, and 749 wavenumbers. The 25° C. viscosity for this compound was 805 cps at 5 RPM.

Example 36

1,6-Acyloxy Substituted Naphthalene Epoxy Curative

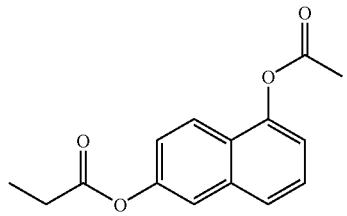

1,6-Dihydroxynaphthalene (16.0 g, 100 mmol), acetic anhydride (10.2 g, 100 mmol), propionic anhydride (13.0 g, 100 mmol), and 4-dimethylaminopyridine (50 mg) were charged into a 250 ml flask. The flask was rotated for 4.5 hours in a heated bath that was controlled at approximately 85° C. An FTIR on the crude product indicated the complete disappearance of the anhydride carbonyl absorptions. The acids were removed via a combination of vacuum and air sparge at 85° C. The product was initially a black-brown liquid. The product solidified into a milky brown solid after standing for several hours at room temperature. The recovered product weighed 24.6 g (95.3% theory). The compound was subjected to thermogravimetric analysis (TGA). The retained weight at 200° C. (TGA ramp rate=10° C./min., air purge) was 96.9% and the decomposition onset was at 216° C. The infrared spectrum of this compound included absorptions at 2948, 1755, 1603, 1431, 1367, 1192, 1139, 1037, 899, and 788 wavenumbers.

Example 37

Preparation of Dibenzoate of 2,2'-Diallylbisphenol A

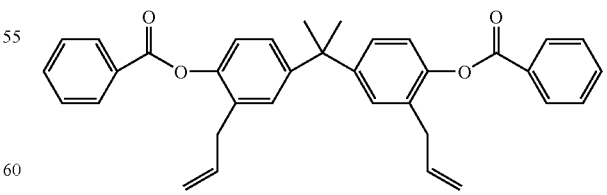

A 500 ml, single-neck flask was charged with 30.84 g (0.1 mole) o,o'-diallylbisphenol A, 200 ml toluene, and 25.3 g (0.25 mole) triethylamine. This mixture was stirred at room temperature and 28.1 g (0.20 mole) benzoyl chloride dissolved in 100 ml toluene was dripped in. The mixture was stirred for another three hours at room temperature and then one hour at 100° C. The mixture was cooled to room temperature and then extracted with four 50 ml portions of deionized water, followed by 50 ml of brine. The solution was dried with ten grams of MgSO$_4$ and then passed over 20 g of silica gel. The toluene was removed to yield 50.72 g (98.2% of theory) of a clear, light yellow, very viscous tacky liquid. The compound had prominent absorptions at 2970, 1638, 1495, 1450, 1251, 1168, 1057, 1023, 994, 914, 873, 812, and 704 wavenumbers. The viscosity of this liquid was 71,760 centipoise at 40° C. A TGA was run on this compound revealed 97.82% residue remained at 300° C. while the decomposition onset was at 351.3° C.

Example 38

Mixed Acetate-Propionates Versus All-Acetate Compounds

Phenyl esters containing a mixture of acyloxy functional groups were found to have significantly lower melting points than the corresponding acetate-only counterparts. The value of this approach for melting point suppression is demonstrated in Table 7.

TABLE 7

Melting Point Comparison Between Mixed Acetate-Propionates and All-Acetate Comparative Compounds

| Example Compound | Example Melting Point (° C.) | Melting Point of Corresponding All Acetate Compound (° C.) |
| --- | --- | --- |
| 7 | 41-43 | 91-94 |
| 21 | liquid at RT | 78 |
| 22 | 38-42 | 92-94 |
| 26 | liquid at RT | 165-167 |
| 27 | liquid at RT | 105-106 |
| 28 | liquid at RT | 117-118 |
| 30 | 100-101 | 163-165 |

The presence of the mixed acetate-propionate functionality significantly reduced the melting point for the invention phenyl ester compounds compared to the all-acetate comparative compounds. Several of the invention compounds were stable liquids at room temperature, while all of the acetate-only compounds were crystalline solids. Even where the mixed acetate-propionates were solids at room temperature, they were still significantly lower in melting point than the comparative all-acetate compounds. Low melting solids, as a rule are much more soluble in, and therefore compatible with other reactive formulation components.

While this invention has been described with respect to these specific examples, it should be clear that other modifications and variations would be possible without departing from the spirit of this invention.

What is claimed is:

1. A curative for epoxy or oxetane resins, wherein the curative is selected from the group of compounds consisting of:

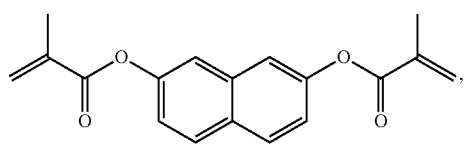

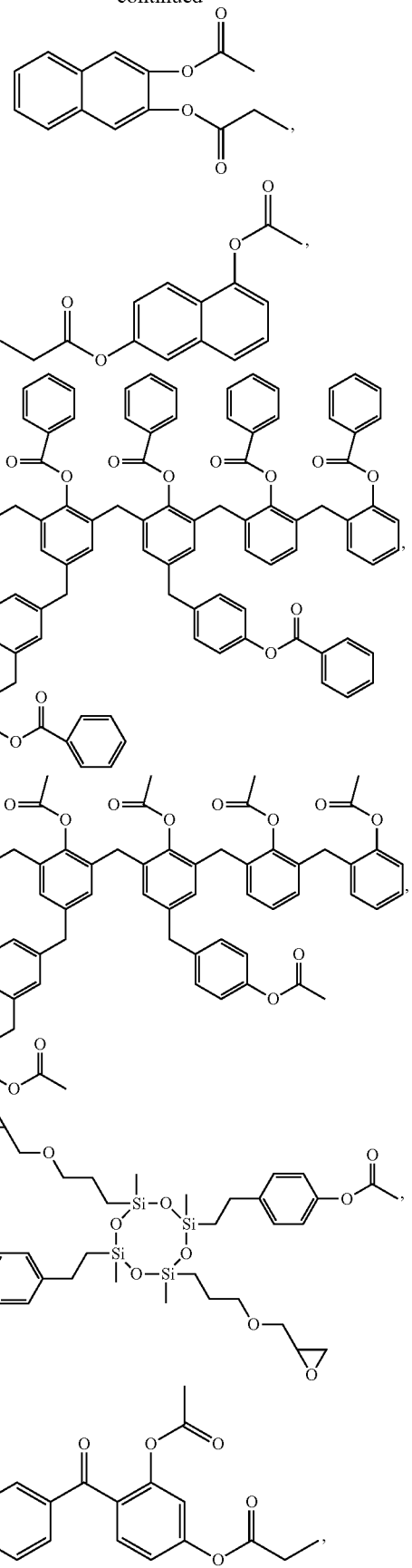

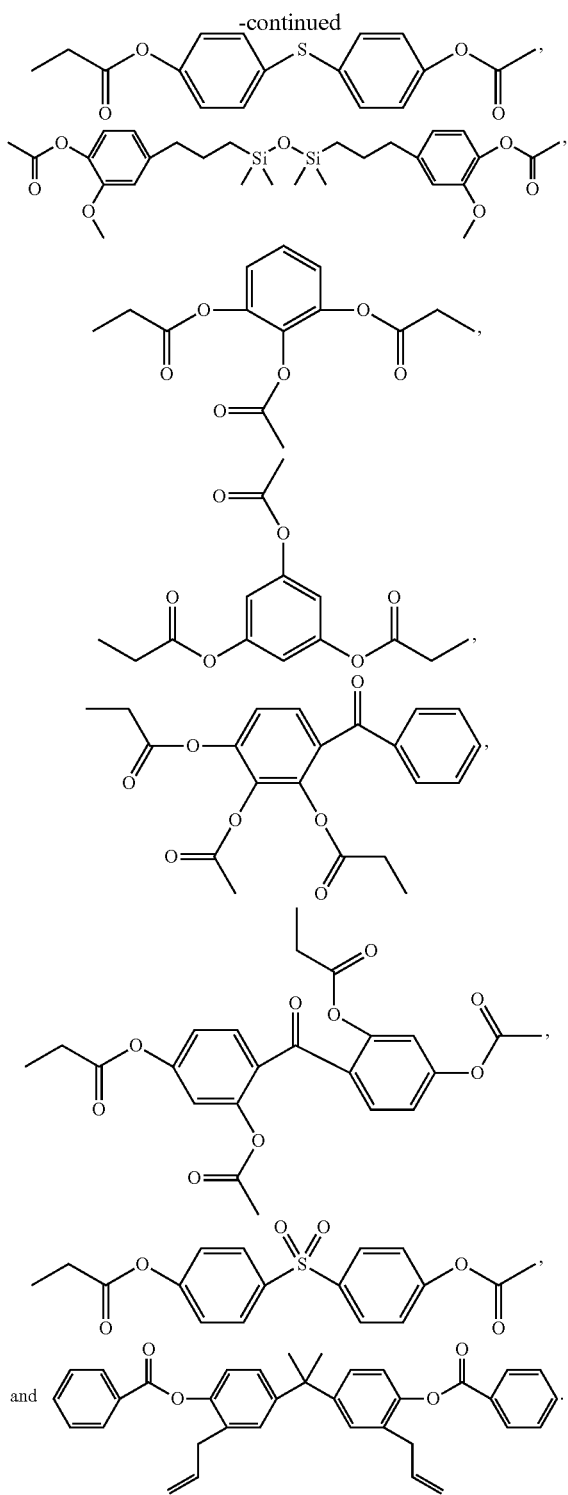

2. The curative of claim 1, wherein the curative is a liquid at room temperature.

3. A composition, comprising:
an epoxy resin or oxetane resin; and
a curative of claim 1.

4. The composition of claim 3, wherein the epoxy comprises at least one of a glycidyl ether epoxy compound, a cycloaliphatic epoxy compound, or an aliphatic epoxy compound.

5. The composition of claim 4, wherein the glycidyl ether epoxy compound is selected from the group consisting of:
   (a) a glycidyl ether of a phenol, an amine, an alcohol, or an isocyanurate;
   (b) a trisglycidyl ether of a phenolic compound;
   (c) a glycidyl ether of a cresol formaldehyde condensate;
   (d) a glycidyl ether of a phenol formaldehyde condensate;
   (e) a glycidyl ether of a cresol dicyclopentadiene addition compound;
   (f) a glycidyl ether of a phenol dicyclopentadiene addition compound;
   (g) a glycidyl ether of a fused ring polyaromatic phenol;
   (h) diglycidyl ether;
   (i) a glycidyl ether of an aliphatic alcohol;
   (j) a glycidyl ether of a polyglycol;
   (k) a glycidyl derivative of an aromatic amine; and
   (l) an ester linked epoxy compound.

6. The composition of claim 4, wherein the glycidyl ether epoxy compound is selected from the group consisting of:
   (a) a phenyl glycidyl ether;
   (b) a cresyl glycidyl ether;
   (c) a nonylphenyl glycidyl ether;
   (d) a p-tert-butylphenyl glycidyl ether;
   (e) a diglycidyl ether;
   (f) a diglycidyl ether of bisphenol A, a diglycidyl ether of bisphenol F, a diglycidyl ether of ethylidinebisphenol, a diglycidyl ether of dihydroxydiphenyl ether, a diglycidyl ether of N,N'-disalicylal-ethylenediamine, triglycidyl-p-aminophenol, N,N,N',N'-tetraglycidyl-4,4'-diphenylmethane, triglycidyl isocyanurate, bis(4-hydroxyphenyl)sulfone, a diglycidyl ether of bis(hydroxyphenyl)sulfide, a diglycidyl ether of 1,1-bis(hydroxyphenyl)cyclohexane, a diglycidyl ether of 9,19-bis(4-hydroxyphenyl)fluorene, a trisglycidyl ether of 1,1,1-tris(hydroxyphenyl)ethane, a trisglycidyl ether of trihydroxytritylmethane, a diglycidyl ether of 4,4'-(1-alpha-methylbenzylidene)bisphenol, a diglycidyl ether of 4,4'-(1,2ethylene)diphenol, a diglycidyl ether of stilbesterol, a diglycidyl ether of 4,4'-dihyroxybenzophenone, a diglycidyl ether of resorcinol, or a diglycidyl ether of catechol;
   (g) a glycidyl ether of a dihydroxy naphthalene, 2,2'-dihydroxy-6,6'-dinaphthyl disulfide, or 1,8,9-trihydroxyanthracene;
   (h) a diglycidyl ether of 1,4 butanediol;
   (i) a diglycidyl ether of diethylene glycol;
   (j) a diglycidyl ether of neopentyl glycol; a diglycidyl ether of cyclohexane dimethanol;
   (k) a diglycidyl ether of tricyclodecane dimethanol;
   (l) a trimethyolethane triglycidyl ether;
   (m) a glycidyl ether a trimethyol propane triglycidyl ether;
   (n) a polyglycidyl ether of castor oil;
   (o) polyoxypropylene diglycidyl ether; and
   (p) glycidyl methacrylate.

7. The composition of claim 4, wherein the cycloaliphatic epoxy compound is selected from the group consisting of a cyclohexene oxide, a 3-vinylcyclohexene oxide, vinylcyclohexene dioxide, a dicylcopentadiene dioxide, a tricyclopentadiene dioxide, a tetracyclopentadiene dioxide, a norbornadiene dioxide, a bis(2,3-epoxycyclopentyl) ether, a limonene dioxide, a 3',4'-epoxycyclohexamethyl-3,4-epoxycyclohexanecarboxylate, a 3',4'-epoxycyclohexyloxirane, a 2(3',4'-epoxycyclohexyl)-5,1"-spiro-3",4"-epoxycyclohexane-1,3-dioxane, and a bis(3,4-epoxycyclohexamethyl) adipate; or the aliphatic epoxy compound is selected from the group consisting of an epoxidized polybutadiene, an epoxidized polyisoprene, an epoxidized poly(1,3-butadiene-acrylonitrile), an epoxized soybean oil, an epoxidized castor oil, a dimethylpentane dioxide, a divinylbenzene dioxide, a butadiene dioxide, and a 1,7-octadiene dioxide.

8. The composition of claim 4, wherein the composition is an adhesive, a coating, a matrix resin or a composite resin.

9. The composition of claim 8, wherein the matrix resin is an encapsulant, industrial, marine, automotive, airline, aerospace, sporting goods, medical or dental matrix resin.

10. The composition of claim 8, wherein the composite resin further comprises at least one of carbon fiber, fiberglass or silica.

11. The composition of claim 8, wherein the adhesive further comprises at least one compound selected from the group consisting of an acrylate, a methacrylate, a maleimide, a vinyl ether, a vinyl ester, a styrenic compound, an allyl functional compound, a phenol, an anhydride, a benzoxazine, and an oxazoline.

12. A method for decreasing the hydrophilicity of an epoxy resin or an oxetane resin, comprising combining a curative of claim 1 with the epoxy resin or the oxetane resin.

\* \* \* \* \*